US007858626B2

(12) United States Patent
Boloor et al.

(10) Patent No.: US 7,858,626 B2
(45) Date of Patent: Dec. 28, 2010

(54) PYRIMIDINEAMINES AS ANGIOGENESIS MODULATORS

(75) Inventors: Amogh Boloor, La Jolla, CA (US); Mui Cheung, Wayne, PA (US); Ronda Gayle Davis-Ward, North Little Rock, AR (US); Philip Anthony Harris, Wayne, PA (US); Kevin Hinkle, Phoenixville, PA (US); Christopher P. Lauderman, Durham, NC (US); Robert Anthony Mook, Jr., Chapel Hill, NC (US); Jeffery Alan Stafford, San Diego, CA (US); James Marvin Veal, Apex, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 11/830,024

(22) Filed: Jul. 30, 2007

(65) Prior Publication Data
US 2007/0270427 A1    Nov. 22, 2007

Related U.S. Application Data

(60) Division of application No. 11/383,229, filed on May 15, 2006, now Pat. No. 7,262,203, which is a continuation of application No. 10/451,305, filed as application No. PCT/US01/49367 on Dec. 19, 2001, now Pat. No. 7,105,530.

(60) Provisional application No. 60/262,403, filed on Jan. 16, 2001, provisional application No. 60/257,526, filed on Dec. 21, 2000.

(51) Int. Cl.
C07D 403/04  (2006.01)
A61K 31/53   (2006.01)
A61P 35/00   (2006.01)

(52) U.S. Cl. .................. 514/245; 544/207; 544/209
(58) Field of Classification Search ............ 544/207, 544/209, 245; 514/245
See application file for complete search history.

(56) References Cited

U.S. PATENT DOCUMENTS

| 6,022,307 | A | 2/2000 | Salvati et al. | |
|---|---|---|---|---|
| 6,265,411 | B1 | 7/2001 | Thomas et al. | |
| 6,294,532 | B1 | 9/2001 | Thomas et al. | |
| 6,316,603 | B1 | 11/2001 | McTigue et al. | |
| 7,074,789 | B2 * | 7/2006 | Armistead et al. | 514/241 |
| 7,105,530 | B2 | 9/2006 | Boloor et al. | |
| 7,262,203 | B2 | 8/2007 | Boloor et al. | |
| 7,282,504 | B2 | 10/2007 | Armistead et al. | |
| 2003/0004174 | A9 | 1/2003 | Armistead et al. | |
| 2004/0116388 | A1 * | 6/2004 | Armistead et al. | 514/84 |

FOREIGN PATENT DOCUMENTS

| EP | 0 002 341 | 11/1978 |
|---|---|---|
| EP | 0 945 443 | 9/1999 |
| EP | 0 787 742 | 12/2001 |
| WO | 93/11106 | 6/1993 |
| WO | 96/05177 | 2/1996 |
| WO | 97/19065 | 5/1997 |
| WO | 97/22596 | 6/1997 |
| WO | 97/30035 | 8/1997 |
| WO | 97/32856 | 9/1997 |
| WO | 97/34786 | 9/1997 |
| WO | 98/18782 | 5/1998 |
| WO | 98/54093 | 12/1998 |
| WO | 99/16755 | 4/1999 |
| WO | 99/60630 | 11/1999 |
| WO | 99/62890 | 12/1999 |
| WO | 00/02871 | 1/2000 |
| WO | 00/12089 | 3/2000 |
| WO | 00/12485 | 3/2000 |
| WO | 00/14105 | 3/2000 |
| WO | 00/21955 | 4/2000 |
| WO | 00/39101 | 7/2000 |
| WO | 00/43373 | 7/2000 |
| WO | 00/47212 | 8/2000 |
| WO | 00/52470 | 9/2000 |
| WO | 00/53595 | 9/2000 |
| WO | 00/53605 | 9/2000 |
| WO | 00/59892 | 10/2000 |
| WO | 00/63204 | 10/2000 |
| WO | 00/73264 | 12/2000 |
| WO | 01/00213 | 1/2001 |
| WO | 01/09134 | 2/2001 |
| WO | 01/14375 | 3/2001 |
| WO | 01/17995 | 3/2001 |
| WO | 01/25220 | 4/2001 |
| WO | 01/40218 | 6/2001 |
| WO | 01/47921 | 7/2001 |

(Continued)

OTHER PUBLICATIONS

Arasteh et al., "The Role of Vascular Endothelial Growth Factor (VEGF) in AIDS-Related Kaposi's Sarcoma," *The Oncologist*, 2000, vol. 5 (Supp. 1), pp. 28-31.

(Continued)

Primary Examiner—Venkataraman Balasubramanian
(74) Attorney, Agent, or Firm—J. Michael Strickland

(57) ABSTRACT

Pyrimidine derivatives, which are useful as VEGFR2 inhibitors are described herein. The described invention also includes methods of making such pyrimidine derivatives as well as methods of using the same in the treatment of hyperproliferative diseases.

20 Claims, No Drawings

FOREIGN PATENT DOCUMENTS

| WO | 01/60816 | 8/2001 |
|---|---|---|
| WO | 01/64654 | 9/2001 |
| WO | 01/64655 | 9/2001 |
| WO | 01/64656 | 9/2001 |
| WO | 01/74296 | 10/2001 |
| WO | 02/22601 | 3/2002 |
| WO | 02/50045 | 6/2002 |

OTHER PUBLICATIONS

Arutyunyan et al., "Certain Peculiarities in the Reaction of Uracils with Phosphoric Acid Amides," N.D. Zelinskii Institute of Organic Chemistry, Academy of Sciences of the USSR, pp. 848-853.

Banker et al., "Modern Pharaceutices, 3 ed.," Marcel Dekker, New York, 1996, pp. 451 and 596.

Carter, "Clinical Strategy for the Development of Angiogenesis Inhibitors," The Oncologist, vol. 5 (Supp. 1), 2000, pp. 51-54.

Cecil Textbook of Medicine, eds. Bennet and Plum, 20th ed., 1996, vol. 1, pp. 1004-1010.

Connell et al., "Patent Focus on Cancer Chemotherapies. II Angiogenesis Agents: Apr. 2000-Sep. 2000," Exp. Opinion Ther. Patients, 2001, vol. 11, No. 1, pp. 77-114.

Ellis et al., "Vascular Endothelial Growth Factor in Human Colon Cancer: Biology and Therapeutic Implications," The Oncologist, 2000, vol. 5 (Supp. 1), pp. 11-15.

Gasparini, "Prognostic Value of Vascular Endothelial Growth Factor in Breast Cancer," The Oncologist, 2000, vol. 5 (Supp. 1), pp. 37-44.

Ghosh, "2,4-Bis(Arylamino)-6-Methyl Pyrimidines as Antimicrobial Agents," J. Indian Chem. Soc., vol. LVIII, May 1981, pp. 512-513.

Ghosh et al., "2,4 BIS(p-Chloroanilino)-Pyrimidine, an Uncoupler of Oxidative Phosphorylation," FEBS Letters, vol. 4, No. 3, Aug. 1969, pp. 157-159.

Harris, "von Hippel-Lindau Syndrome: Target for Anti-Vascular Endothelial Growth Factor (VEGF) Receptor Therapy," The Oncologist, 2000, vol. 5 (Supp. 1), pp. 32-36.

Kerbel, "A Cancer Therapy Resistant to Resistance," Nature, Nov. 1997, vol. 390, pp. 335-336.

Kerdawy et al., "Synthesis of Certain Esters of Pteroyl Glutamic Acid Analogues Structurally Related to Antimetabolite Anticancer Compounds," J. Pharm. Sci. U.A.R., 1968, vol. 9, pp. 1-6.

Klement et al., "Continuous Low-Dose Therapy with Vinblastine and VEGF Receptor-2 Antibody Induces Sustained Tumor & Regression without Over Toxicity," Journal of Clinical Investigation, Apr. 2000, vol. 105, No. 8, pp. 15-24.

McMahon, "VEGF Receptor Signaling in Tumor Angiogenesis," The Oncologist, 2000, vol. 5 (Supp. 1), pp. 3-10.

Pinedo et al., "Translational Research: The Role of VEGF in Tumor Angiogenesis," The Oncologist, 2000, vol. 5 (Supp. 1), pp. 1-2.

Rose, "Antiangiogenic Strategies and Agents in Clincial Trials," The Oncologist, 2000, vol. 5 (Supp. 1), pp. 20-27.

Russian Article #1, pp. 7-18, 1983.

Russian Article #2, pp. 1304-1307.

Sennlaub et al., The Journal of Clinical Investigation, 2001, vol. 107, No. 6, pp. 717-725.

Shawyer et al., "Receptor Tyrosine Kinases as Targets for Inhibition of Angiogenesis," DDT, vol. 2, No. 2, Feb. 1997, pp. 50-63.

Vajkoczy et al., "Measuring VEGF-Flk-1 Activity and Consequences of VEGF-Flk-1 Targeting In Vivo Using Intravital Microscopy: Clinical Applications," The Oncologist, 2000, vol. 5 (Supp. 1), pp. 16-19.

Verheul et al., "Targeting Vascular Endothelial Growth Factor Blockade: Ascites and Pleural Effusion Formation," The Oncologist, 2000, vol. 5 (Supp. 1), pp. 45-50.

Vippagunta et al., Advanced Drug Delivery Reviews, 2001, vol. 48, pp. 3-26.

West, "Solid State Chemistry and Its Applications," Wiley, New York, 1988, pp. 358 and 365.

Wolft, "Burger's Medicinal Chemistry, 5 ed., Part 1," John Wiley & Sons, 1995, pp. 975-977.

Toledo et al., "The Structure-Based Design of ATP-Site Directed Protein Kinase Inhibitors," Current Medicinal Chemistry, 1999, vol. 6, No. 9, pp. 775-805.

* cited by examiner

PYRIMIDINEAMINES AS ANGIOGENESIS MODULATORS

CROSS-REFERENCE TO RELATED APPLICATIONS

This application is a Divisional of Ser. No. 11/383,229 filed May 15, 2006, now U.S. Pat. No. 7,262,203; which is a Continuation of Ser. No. 10/451,305 filed Jun. 9, 2004 now U.S. Pat. No. 7,105,530; which is a 371 of PCT/US01/49367 filed Dec. 19, 2001; which claims priority to U.S. Provisional Patent Application Ser. No. 60/257,526 filed Dec. 21, 2000 and U.S. Provisional Patent Application Ser. No. 60/262,403 filed Jan. 16, 2001. All five applications are incorporated herein by reference in their entirety.

BACKGROUND OF THE INVENTION

The present invention relates to pyrimidine derivatives, compositions and medicaments containing the same, as well as processes for the preparation and use of such compounds, compositions and medicaments. Such pyrimidine derivatives are useful in the treatment of diseases associated with inappropriate or pathological angiogenesis.

The process of angiogenesis is the development of new blood vessels from the pre-existing vasculature. Angiogenesis is defined herein as involving: (i) activation of endothelial cells; (ii) increased vascular permeability; (iii) subsequent dissolution of the basement membrane and extravasation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vi) deposition of basement membrane and recruitment of perivascular cells to newly formed vessels. Normal angiogenesis is active during tissue growth from embryonic development through maturity and then enters a period of relative quiescence during adulthood. Normal angiogenesis is also activated during wound healing, and at certain stages of the female reproductive cycle. Inappropriate or pathological angiogenesis has been associated with several disease states including various retinopathies, ischemic disease, atherosclerosis, chronic inflammatory disorders, and cancer. The role of angiogenesis in disease states is discussed, for instance, in Fan et al., Trends in Pharmacol Sci. 16:54-66; Shawver et al., DDT Vol. 2, No. 2 February 1997; Folkmann, 1995, Nature Medicine 1:27-31.

In cancer the growth of solid tumors has been shown to be dependent on angiogenesis. The progression of leukemias as well as the accumulation of fluid associated with malignant ascites and pleural effusions also involve pro-angiogenic factors. (See Folkmann, J., J. Nat'l. Cancer Inst., 1990, 82, 4-6.) Consequently, the targeting of pro-angiogenic pathways is a strategy being widely pursued in order to provide new therapeutics in these areas of great, unmet medical need.

Central to the process of angiogenesis are vascular endothelial growth factor (VEGF) and its receptors, termed vascular endothelial growth factor receptor(s) (VEGFRs). The roles VEGF and VEGFRs play in the vascularization of solid tumors, progression of hematopoietic cancers and modulation of vascular permeability have drawn great interest in the scientific community. VEGF is a polypeptide, which has been linked to inappropriate or pathological angiogenesis (Pinedo, H. M. et al. The Oncologist, Vol. 5, No. 90001, 1-2, April 2000). VEGFR(s) are protein tyrosine kinases (PTKs) that catalyze the phosphorylation of specific tyrosine residues in proteins that are involved in the regulation of cell growth, differentiation, and survival. (A. F. Wilks, Progress in Growth Factor Research, 1990, 2, 97-111; S. A. Courtneidge, Dev. Suppl., 1993, 57-64; J. A. Cooper, Semin. Cell Biol., 1994, 5(6), 377-387; R. F. Paulson, Semin. Immunol., 1995, 7(4), 267-277; A. C. Chan, Curr. Opin. Immunol., 1996, 8(3), 394-401).

Three PTK receptors for VEGF have been identified: VEGFR1 (Flt-1); VEGFR2 (Flk-1 and KDR) and VEGFR3 (Flt-4). These receptors are involved in angiogenesis and participate in signal transduction. (Mustonen, T. et al. J. Cell Biol. 1995:129:895-898; Ferrara and Davis-Smyth, Endocrine Reviews, 18(1):4-25, 1997; McMahon, G., The Oncologist, Vol. 5, No 90001, 3-10, April 2000).

Of particular interest is VEGFR2, which is a transmembrane receptor PTK expressed primarily in endothelial cells. Activation of VEGFR-2 by VEGF is a critical step in the signal transduction pathway that initiates tumor angiogenesis. VEGF expression may be constitutive to tumor cells and can also be upregulated in response to certain stimuli. One such stimulus is hypoxia, where VEGF expression is upregulated in both tumor and associated host tissues. The VEGF ligand activates VEGFR2 by binding to its extracellular VEGF binding site. This leads to receptor dimerization of VEGFRs and autophosphorylation of tyrosine residues at the intracellular kinase domain of VEGFR2. The kinase domain operates to transfer a phosphate from ATP to the tyrosine residues, thus providing binding sites for signaling proteins downstream of VEGFR-2 leading ultimately to angiogenesis. (Ferrara and Davis-Smyth, Endocrine Reviews, 18(1):4-25, 1997; McMahon, G., The Oncologist, Vol. 5, No. 90001, 3-10, April 2000.)

Consequently, antagonism of the VEGFR2 kinase domain would block phosphorylation of tyrosine residues and serve to disrupt initiation of angiogenesis. Specifically, inhibition at the ATP binding site of the VEGFR2 kinase domain would prevent binding of ATP and prevent phosphorylation of tyrosine residues. Such disruption of the pro-angiogenesis signal transduction pathway associated with VEGFR2 should therefore inhibit tumor angiogenesis and thereby provide a potent treatment for cancer or other disorders associated with inappropriate angiogenesis.

The present inventors have discovered novel pyrimidine derivative compounds, which are inhibitors of VEGFR-2 kinase activity. Such pyrimidine derivatives are useful in the treatment of disorders, including cancer, associated with inappropriate angiogenesis.

BRIEF SUMMARY OF THE INVENTION

In one aspect of the present invention, there is provided a compound of Formula (I):

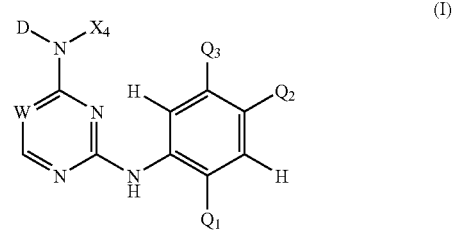

or a salt, solvate, or physiologically functional derivative thereof:

wherein:

D is

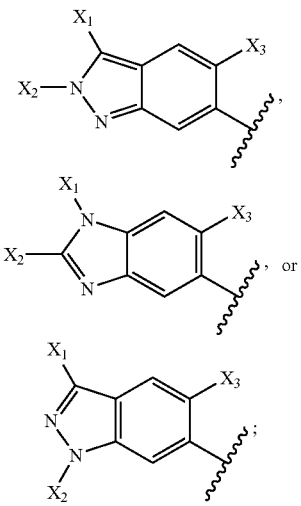

$X_1$ is hydrogen, $C_1$-$C_4$ alkyl, $C_1$-$C_4$ haloalkyl, or $C_1$-$C_4$ hydroxyalkyl;

$X_2$ is hydrogen, $C_1$-$C_4$ alkyl, $C_1$-$C_4$ haloalkyl, $C(O)R^1$, or aralkyl;

$X_3$ is hydrogen or halogen;

$X_4$ is hydrogen, $C_1$-$C_4$ alkyl, $C_1$-$C_4$ haloalkyl, heteroaralkyl, cyanoalkyl, $-(CH_2)_pC=CH(CH_2)_tH$, $-(CH_2)_pC\equiv C(CH_2)_tH$, or $C_3$-$C_7$ cycloalkyl;

p is 1, 2, or 3;

t is 0 or 1;

W is N or C—R, wherein R is hydrogen, halogen, or cyano;

$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;

$Q_2$ is $A^1$ or $A^2$;

$Q_3$ is $A^1$ when $Q_2$ is $A^2$ and $Q_3$ is $A^2$ when $Q_2$ is $A^1$;

wherein $A^1$ is hydrogen, halogen, $C_1$-$C_3$ alkyl, $C_1$-$C_3$ haloalkyl, —$OR^1$, and $A^2$ is the group defined by $-(Z)_m-(Z^1)-(Z^2)$, wherein Z is $CH_2$ and m is 0, 1, 2, or 3, or Z is $NR^2$ and m is 0 or 1, or Z is oxygen and m is 0 or 1, or Z is $CH_2NR^2$ and m is 0 or 1;

$Z^1$ is $S(O)_2$, $S(O)$, or $C(O)$; and $Z^2$ is $C_1$-$C_4$ alkyl, $NR^3R^4$, aryl, arylamino, aralkyl, aralkoxy, or heteroaryl, $R^1$ is $C_1$-$C_4$ alkyl;

$R^2$, $R^3$, and $R^4$ are each independently selected from hydrogen, $C_1$-$C_4$ alkyl, $C_3$-$C_7$ cycloalkyl, —$S(O)_2R^5$, and —$C(O)R^5$;

$R^5$ is $C_1$-$C_4$ alkyl, or $C_3$-$C_7$ cycloalkyl; and when Z is oxygen then $Z^1$ is $S(O)_2$ and when D is

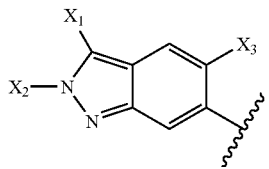

then $X_2$ is $C_1$-$C_4$ alkyl, $C_1$-$C_4$ haloalkyl, $C(O)R^1$, or aralkyl.

In a second aspect of the present invention, there is provided a compound of Formula (II):

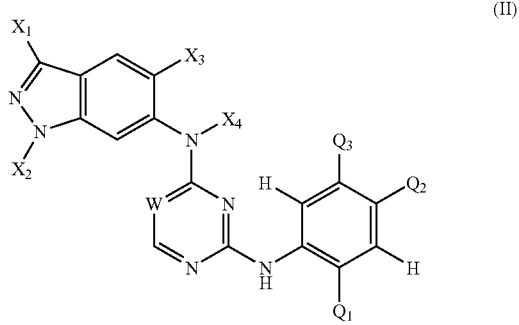

(II)

or a salt, solvate, or physiologically functional derivative thereof:

wherein:

$X_1$ is hydrogen, $C_1$-$C_4$ alkyl, $C_1$-$C_4$ haloalkyl, or $C_1$-$C_4$ hydroxyalkyl;

$X_2$ is hydrogen, $C_1$-$C_4$ alkyl, $C_1$-$C_4$ haloalkyl, $C(O)R^1$, or aralkyl;

$X_3$ is hydrogen or halogen;

$X_4$ is hydrogen, $C_1$-$C_4$ alkyl, $C_1$-$C_4$ haloalkyl, heteroaralkyl, cyanoalkyl, $-(CH_2)_pC=CH(CH_2)_tH$, $-(CH_2)_pC\equiv C(CH_2)_tH$, or $C_3$-$C_7$ cycloalkyl;

p is 1, 2, or 3;

t is 0 or 1;

W is N or C—R, wherein R is hydrogen, halogen, or cyano;

$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;

$Q_2$ is $A^1$ or $A^2$;

$Q_3$ is $A^1$ when $Q_2$ is $A^2$ and $Q_3$ is $A^2$ when $Q_2$ is $A^1$;

wherein $A^1$ is hydrogen, halogen, $C_1$-$C_3$ alkyl, $C_1$-$C_3$ haloalkyl, —$OR^1$, and $A^2$ is the group defined by $-(Z)_m-(Z^1)-(Z^2)$, wherein Z is $CH_2$ and m is 0, 1, 2, or 3, or Z is $NR^2$ and m is 0 or 1, or Z is oxygen and m is 0 or 1, or Z is $CH_2NR^2$ and m is 0 or 1;

$Z^1$ is $S(O)_2$, $S(O)$, or $C(O)$; and $Z^2$ is $C_1$-$C_4$ alkyl, $NR^3R^4$, aryl, arylamino, aralkyl, aralkoxy, or heteroaryl, $R^1$ is $C_1$-$C_4$ alkyl;

$R^2$, $R^3$, and $R^4$ are each independently selected from hydrogen, $C_1$-$C_4$ alkyl, $C_3$-$C_7$ cycloalkyl,
—$S(O)_2R^5$, and —$C(O)R^5$;

$R^5$ is $C_1$-$C_4$ alkyl, or $C_3$-$C_7$ cycloalkyl; and when Z is oxygen then $Z^1$ is $S(O)_2$.

In a third aspect of the present invention, there is provided a compound of Formula (III):

(III)

or a salt, solvate, or physiologically functional derivative thereof:

wherein:

$X_1$ is hydrogen, $C_1$-$C_4$ alkyl, $C_1$-$C_4$ haloalkyl, or $C_1$-$C_4$ hydroxyalkyl;

$X_2$ is $C_1$-$C_4$ alkyl, $C_1$-$C_4$ haloalkyl, or $C(O)R^1$;

$X_3$ is hydrogen or halogen;

$X_4$ is hydrogen, $C_1$-$C_4$ alkyl, $C_1$-$C_4$ haloalkyl, heteroaralkyl, cyanoalkyl, —$(CH_2)_pC$=$CH(CH_2)_tH$, —$(CH_2)_pC$≡$C(CH_2)_tH$, or $C_3$-$C_7$ cycloalkyl;

p is 1, 2, or 3;

t is 0 or 1;

W is N or C—R, wherein R is hydrogen, halogen, or cyano;

$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;

$Q_2$ is $A^1$ or $A^2$;

$Q_3$ is $A^1$ when $Q_2$ is $A^2$ and $Q_3$ is $A^2$ when $Q_2$ is $A^1$;

wherein
  $A^1$ is hydrogen, halogen, $C_1$-$C_3$ alkyl, $C_1$-$C_3$ haloalkyl, —$OR^1$, and
  $A^2$ is the group defined by -$(Z)_m$-$(Z^1)$-$(Z^2)$, wherein
  Z is $CH_2$ and m is 0, 1, 2, or 3, or
  Z is $NR^2$ and m is 0 or 1, or
  Z is oxygen and m is 0 or 1, or
  Z is $CH_2NR^2$ and m is 0 or 1;
  $Z^1$ is $S(O)_2$, $S(O)$, or $C(O)$; and
  $Z^2$ is $C_1$-$C_4$ alkyl, $NR^3R^4$, aryl, arylamino, aralkyl, aralkoxy, or heteroaryl, $R^1$ is $C_1$-$C_4$ alkyl;

$R^2$, $R^3$, and $R^4$ are each independently selected from hydrogen, $C_1$-$C_4$ alkyl, $C_3$-$C_7$ cycloalkyl,
—$S(O)_2R^5$, and —$C(O)R^5$;

$R^5$ is $C_1$-$C_4$ alkyl, or $C_3$-$C_7$ cycloalkyl; and when Z is oxygen then $Z^1$ is $S(O)_2$.

In a fourth aspect of the present invention, there is provided a compound of Formula (IV):

(IV)

or a salt, solvate, or physiologically functional derivative thereof:

wherein:

$X_1$ is hydrogen, $C_1$-$C_4$ alkyl, $C_1$-$C_4$ haloalkyl, or $C_1$-$C_4$ hydroxyalkyl;

$X_2$ is hydrogen, $C_1$-$C_4$ alkyl, $C_1$-$C_4$ haloalkyl, or $C(O)R^1$, or aralkyl;

$X_3$ is hydrogen or halogen;

$X_4$ is hydrogen, $C_1$-$C_4$ alkyl, $C_1$-$C_4$ haloalkyl, heteroaralkyl, cyanoalkyl, —$(CH_2)_pC$=$CH(CH_2)_tH$, —$(CH_2)_pC$≡$C(CH_2)_tH$, or $C_3$-$C_7$ cycloalkyl;

p is 1, 2, or 3;

t is 0 or 1;

W is N or C—R, wherein R is hydrogen, halogen, or cyano;

$Q_1$ is hydrogen, halogen, $C_1$-$C_2$ haloalkyl, $C_1$-$C_2$ alkyl, $C_1$-$C_2$ alkoxy, or $C_1$-$C_2$ haloalkoxy;

$Q_2$ is $A^1$ or $A^2$;

$Q_3$ is $A^1$ when $Q_2$ is $A^2$ and $Q_3$ is $A^2$ when $Q_2$ is $A^1$;

wherein
  $A^1$ is hydrogen, halogen, $C_1$-$C_3$ alkyl, $C_1$-$C_3$ haloalkyl, —$OR^1$, and
  $A^2$ is the group defined by -$(Z)_m$-$(Z^1)$-$(Z^2)$, wherein
  Z is $CH_2$ and m is 0, 1, 2, or 3, or
  Z is $NR^2$ and m is 0 or 1, or
  Z is oxygen and m is 0 or 1, or
  Z is $CH_2NR^2$ and m is 0 or 1;
  $Z^1$ is $S(O)_2$, $S(O)$, or $C(O)$; and
  $Z^2$ is $C_1$-$C_4$ alkyl, $NR^3R^4$, aryl, arylamino, aralkyl, aralkoxy, or heteroaryl, $R^1$ is $C_1$-$C_4$ alkyl;

$R^2$, $R^3$, and $R^4$ are each independently selected from hydrogen, $C_1$-$C_4$ alkyl, $C_3$-$C_7$ cycloalkyl, —$S(O)_2R^5$, and —$C(O)R^5$;

$R^5$ is $C_1$-$C_4$ alkyl, or $C_3$-$C_7$ cycloalkyl; and when Z is oxygen then $Z^1$ is $S(O)_2$.

In a fifth aspect of the present invention, there is provided a pharmaceutical composition including a therapeutically effective amount of a compound of formula (I) or a salt, solvate, or a physiologically functional derivative thereof and one or more of pharmaceutically acceptable carriers, diluents and excipients.

In a sixth aspect of the present invention, there is provided a method of treating a disorder in a mammal, said disorder being mediated by inappropriate VEGFR2 activity, including: administering to said mammal a therapeutically effective amount of a compound of formula (I) or a salt, solvate or a physiologically functional derivative thereof.

In a seventh aspect of the present invention, there is provided a compound of formula (I), or a salt, solvate, or a physiologically functional derivative thereof for use in therapy.

In an eighth aspect of the present invention, there is provided the use of a compound of formula (I), or a salt, solvate, or a physiologically functional derivative thereof in the preparation of a medicament for use in the treatment of a disorder mediated by inappropriate VEGFR2 activity.

In a ninth aspect of the present invention, there is provided a method of treating a disorder in a mammal, said disorder being mediated by inappropriate VEGFR2 activity, including: administering to said mammal therapeutically effective amounts of (i) a compound of formula (I), or a salt, solvate or physiologically functional derivative thereof and (ii) an agent to inhibit growth factor receptor function.

In an tenth aspect of the present invention, there is provided a method of treating a disorder in a mammal, said disorder being characterized by inappropriate angiogenisis, including: administering to said mammal a therapeutically effective amount of a compound of formula (I), or a salt, solvate or physiologically functional derivative thereof.

In an eleventh aspect of the present invention, there is provided a method of treating cancer in a mammal, including administering to said mammal a therapeutically effective amount of a compound of formula (I), or salt, solvate or physiologically functional derivative thereof.

In a twelfth aspect of the present invention, there is provided a method of treating cancer in a mammal, including administering to said mammal therapeutically effective amounts of (i) a compound of formula (I), or salt, solvate or physiologically functional derivative thereof and (ii) at least one additional anti-cancer therapy.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "lower" refers to a group having between one and six carbons.

As used herein, the term "alkyl" refers to a straight or branched chain hydrocarbon having from one to twelve carbon atoms, optionally substituted with substituents selected from the group consisting of lower alkyl, lower alkoxy, lower alkylsulfanyl, lower alkylsulfenyl, lower alkylsulfonyl, oxo, mercapto, amino optionally substituted by alkyl, carboxy, carbamoyl optionally substituted by alkyl, aminosulfonyl optionally substituted by alkyl, nitro, or lower perfluoroalkyl, multiple degrees of substitution being allowed. Examples of "alkyl" as used herein include, but are not limited to, n-butyl, n-pentyl, isobutyl, and isopropyl, and the like.

As used herein, the term "$C_1$-$C_4$ alkyl" refers to an alkyl group, as defined above, which contains at least 1, and at most 4, carbon atoms. Examples of "$C_1$-$C_4$ alkyl" groups useful in the present invention include, but are not limited to, methyl, ethyl, propyl, isopropyl, isobutyl and n-butyl.

In a like manner, the terms "$C_1$-$C_2$ alkyl" and "$C_1$-$C_3$ alkyl" refer to an alkyl group, as defined above, which contains at least 1, and at most 2 and 3, carbon atoms respectively. Examples of "$C_1$-$C_2$ alkyl" and "$C_1$-$C_3$ alkyl" groups useful in the present invention include, methyl, ethyl, n-propyl and isopropyl.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene, and the like.

As used herein, the terms "$C_1$-$C_3$ alkylene" and "$C_1$-$C_4$ alkylene" refer to an alkylene group, as defined above, which contains at least 1, and at most 3 or 4, carbon atoms respectively. Examples of "$C_1$-$C_3$ alkylene" groups useful in the present invention include, but are not limited to, methylene, ethylene, and n-propylene.

As used herein, the terms "halogen" or "halo" refer to fluoro (—F), chloro (—Cl), bromo (—Br), or iodo (—I).

As used herein, the term "$C_1$-$C_4$ haloalkyl" refers to a straight or branched chain hydrocarbon containing at least 1, and at most 4, carbon atoms substituted with at least one halogen, halogen being as defined herein. Examples of branched or straight chained "$C_1$-$C_4$ haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

In a like manner, the terms "$C_1$-$C_2$ haloalkyl" and "$C_1$-$C_3$ haloalkyl" refer to a straight or branched chain hydrocarbon containing at least 1, and at most 2 and 3, carbon atoms respectively substituted with at least one halogen, halogen being as defined herein. Examples of branched or straight chained "$C_1$-$C_2$ haloalkyl" and "$C_1$-$C_3$ haloalkyl" groups useful in the present invention include, but are not limited to, methyl, ethyl, n-propyl, and isopropyl substituted independently with one or more halogens, e.g., fluoro, chloro, bromo and iodo.

As used herein, the term "hydroxy" refers to the group —OH.

As used herein, the term "$C_1$-$C_4$ hydroxyalkyl" refers to a straight or branched chain hydrocarbon containing at least 1, and at most 4, carbon atoms substituted with at least one hydroxy, hydroxy being as defined herein. Examples of branched or straight chained "$C_1$-$C_4$ hydroxyalkyl" groups useful in the present invention include, but are not limited to, methyl, ethyl, propyl, isopropyl, isobutyl and n-butyl substituted independently with one or more hydroxy groups.

As used herein, the term "$C_3$-$C_7$ cycloalkyl" refers to a non-aromatic cyclic hydrocarbon ring having from three to seven carbon atoms, which optionally includes a $C_1$-$C_4$ alkylene linker through which it may be attached. Exemplary "$C_3$-$C_7$ cycloalkyl" groups include, but are not limited to, cyclopropyl, cyclobutyl, cyclopentyl, cyclohexyl and cycloheptyl.

As used herein, the term "heterocyclic" or the term "heterocyclyl" refers to a three to twelve-membered non-aromatic ring being unsaturated or having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "aryl" groups include, but are not limited to, phenyl, 2-naphthyl, 1-naphthyl, biphenyl, as well as substituted derivatives thereof. As used herein, the term "aralkyl" refers to an aryl or heteroaryl group, as defined herein including both unsubstituted and substituted versions thereof, attached through a lower alkylene linker, wherein lower alkylene is as defined herein. As used herein, the term "heteroaralkyl" is included within the scope of the term "aralkyl". The term heteroaralkyl is defined as a heteroaryl group, as defined herein, attached through a lower alkylene linker, lower alkylene is as defined herein. Examples of "aralkyl", including "heteroaralkyl", include, but are not limited to, benzyl, phenylpropyl, 2-pyridinylmethyl, 4-pyridinylmethyl, 3-isoxazolylmethyl, 5-methyl-3-isoxazolylmethyl, and 2-imidazoyly ethyl.

As used herein, the term "arylamino" refers to an aryl or heteroaryl group, as defined herein, attached through an amino group —$NR^2$—, wherein $R^2$ is as defined herein.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "alkoxy" refers to the group $R_aO$—, where $R_a$ is alkyl as defined above and the term "$C_1$-$C_2$ alkoxy" refers to the group $R_aO$—, where $R_a$ is $C_1$-$C_2$ alkyl as defined above.

As used herein, the term "haloalkoxy" refers to the group $R_aO$—, where $R_a$ is haloalkyl as defined above and the term "$C_1$-$C_2$ haloalkoxy" refers to the group $R_aO$—, where $R_a$ is $C_1$-$C_2$ haloalkyl as defined above.

As used herein the term "aralkoxy" refers to the group $R_bR_aO$—, where $R_a$ is alkylene and $R_b$ is aryl, both as defined above.

As used herein, the term "alkylsulfanyl" refers to the group $R_aS$—, where $R_a$ is alkyl as defined above.

As used herein, the term "alkylsulfenyl" refers to the group $R_aS(O)$—, where $R_a$ is alkyl as defined above.

As used herein, the term "alkylsulfonyl" refers to the group $R_aSO_2$—, where $R_a$ is alkyl as defined above.

As used herein, the term "oxo" refers to the group =O.

As used herein, the term "mercapto" refers to the group —SH.

As used herein, the term "carboxy" refers to the group —COOH.

As used herein, the term "cyano" refers to the group —CN.

As used herein the term "cyanoalkyl" refers to the group —$R_a$CN wherein $R_a$ is $C_1$-$C_3$ alkylene as defined above. Exemplary "cyanoalkyl" groups useful in the present invention include, but are not limited to, cyanomethyl, cyanoethyl, and cyanopropyl.

As used herein, the term "aminosulfonyl" refers to the group —$SO_2NH_2$.

As used herein, the term "carbamoyl" refers to the group —$C(O)NH_2$.

As used herein, the term "sulfanyl" shall refer to the group —S—.

As used herein, the term "sulfenyl" shall refer to the group —S(O)—.

As used herein, the term "sulfonyl" shall refer to the group —$S(O)_2$— or —$SO_2$— or —$S(O_2)$.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry and Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I), (II), (III), or (IV) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

The compounds of formulae (I), (II), (III), or (IV) may have the ability to crystallize in more than one form, a characteristic, which is known as polymorphism, and it is understood that such polymorphic forms ("polymorphs") are within the scope of formulae (I), (II), (III), and (IV). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also included within the scope of the invention are the individual isomers of the compounds represented by formula (I), (II), (III), and (IV) above as well as any wholly or partially equilibrated mixtures thereof. The present invention also covers the individual isomers of the compounds represented by the formulas above as mixtures with isomers thereof in which one or more chiral centers are inverted.

It is also noted that the compounds of Formula (I), (II), (III), or (IV) may form tautomers. It is understood that all tautomers and mixtures of tautomers of the compounds of the present invention, more specifically, the compounds of formula (III) are included within the scope of the compounds of the present invention, including the compounds of formula (III).

It is to be understood that the following embodiments refer to compounds within the scope of all of formula (I), formula (II), formula (III), and formula (IV) as defined above except as specifically limited by the definition of each formula or specifically limited otherwise. It is also understood that the embodiments of the present invention described herein, including uses and compositions, are applicable to all of formula (I), (II), (III), and (IV).

In one embodiment D is:

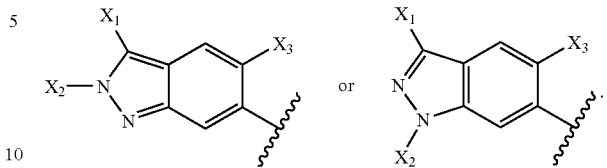

In another embodiment, D is:

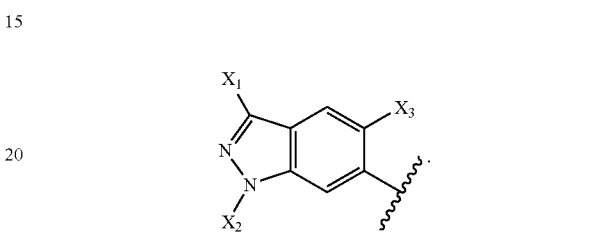

In a further embodiment, D is

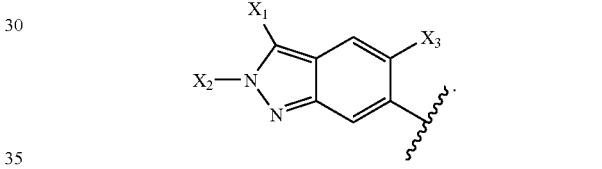

It is understood that D is attached to the indicated nitrogen of Formula (I) through the bond of D having an unfilled valence and being indicated by "\". The appropriate attachment is further illustrated in Formulae (II), (III), or (IV) and in the working examples recited below.

In one embodiment, $X_1$ is hydrogen or $C_{1-4}$ alkyl. In a preferred embodiment, $X_1$ is methyl or ethyl. In a more preferred embodiment, $X_1$ is methyl.

In one embodiment, $X_2$ is hydrogen or $C_{1-4}$ alkyl. In a preferred embodiment, $X_2$ is hydrogen or methyl. In a more preferred embodiment, $X_2$ is hydrogen. In another preferred embodiment, $X_2$ is methyl.

In one embodiment, $X_3$ is halogen. In a preferred embodiment, $X_3$ is hydrogen.

In one embodiment, $X_4$ is hydrogen, $C_1$-$C_4$ alkyl, cyanoalkyl, or $-(CH_2)_pC\equiv C(CH_2)_tH$. In a preferred embodiment, $X_4$ is hydrogen, methyl, ethyl, isopropyl, cyanomethyl, or $-(CH_2)_pC\equiv C(CH_2)_tH$, wherein p is 1 and t is 0. In a more preferred embodiment, $X_4$ is methyl.

In one embodiment, $X_1$ is methyl or ethyl, $X_2$ is hydrogen or methyl, $X_3$ is hydrogen or halogen, and $X_4$ is hydrogen, methyl, ethyl, isopropyl, cyanomethyl, or $-(CH_2)_pC\equiv C(CH_2)_tH$, wherein p is 1 and t is 0. In a preferred embodiment, $X_1$ is methyl, $X_2$ is hydrogen, $X_3$ is hydrogen, and $X_4$ is methyl. In another preferred embodiment, $X_1$ is methyl, $X_2$ is methyl, $X_3$ is hydrogen, and $X_4$ is methyl.

In a preferred embodiment, D is:

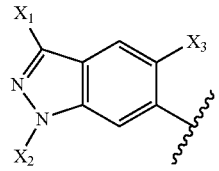

and $X_1$ is methyl, $X_2$ is hydrogen, $X_3$ is hydrogen, and $X_4$ is methyl.

In another preferred embodiment, D is

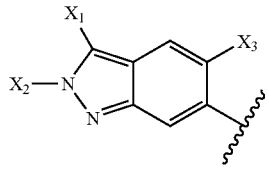

and $X_1$ is methyl, $X_2$ is methyl, $X_3$ is hydrogen, and $X_4$ is methyl.

In one embodiment, W is N. In another embodiment W is C—R wherein R is H, F, or Cl. In a preferred embodiment, W is N, C—H, C—F, or C—CN. In a more preferred embodiment, W is C—F or C—H. In a most preferred embodiment, W is C—H.

In another embodiment, $Q_1$ is hydrogen, halogen, $C_1$-$C_2$ alkyl or $C_1$-$C_2$ alkoxy. In a preferred embodiment, $Q_1$ is hydrogen, chlorine, methyl, or methoxy.

In one embodiment, $Q_2$ is $A^1$ and $Q_3$ is $A^2$. In an alternative embodiment, $Q_2$ is $A^2$ and $Q_3$ is $A^1$.

In one embodiment, $Q_2$ is $A^2$ and $Q_3$ is $A^1$, wherein $A^1$ is hydrogen, halogen, or $C_1$-$C_3$ haloalkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$ and wherein $R^2$, $R^3$, and $R^4$ are each independently selected from H or $C_1$-$C_4$ alkyl. In a preferred embodiment, $Q_2$ is $A^2$ and $Q_3$ is $A^1$, wherein $A^1$ is hydrogen or chlorine and $A^2$ is the group defined by -$(Z)_m$-$(Z^1)$-$(Z^2)$, wherein Z is $CH_2$ and m is 0, 1, 2, or 3; $Z^1$ is $S(O)_2$; and $Z^2$ is $C_1$-$C_4$ alkyl.

In one embodiment, $Q_2$ is $A^1$ and $Q_3$ is $A^2$, wherein $A^1$ is hydrogen, halogen, or $C_1$-$C_3$ alkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from H or $C_1$-$C_4$ alkyl. In a preferred embodiment, $Q_2$ is $A^1$ and $Q_3$ is $A^2$, wherein $A^1$ is hydrogen, methyl, or chlorine and $A^2$ is the group defined by -$(Z)_m$-$(Z^1)$-$(Z^2)$, wherein Z is $CH_2$ and m is 0, 1, 2, or 3; $Z^1$ is $S(O)_2$; and $Z^2$ is $C_1$-$C_4$ alkyl or $NR^3R^4$, wherein $R^3$ and $R^4$ are each independently selected from hydrogen or $C_1$-$C_4$ alkyl.

In one embodiment, $X_1$ is hydrogen or $C_{1-4}$ alkyl; $X_2$ is hydrogen or $C_{1-4}$ alkyl; $X_3$ is hydrogen or halogen; and $X_4$ is hydrogen, $C_1$-$C_4$ alkyl, cyanoalkyl, or —$(CH_2)_p$C≡C$(CH_2)_t$H; W is N; $Q_1$ is hydrogen, halogen, $C_1$-$C_2$ alkyl or $C_1$-$C_2$ alkoxy; and $Q_2$ is $A^2$ and $Q_3$ is $A^1$, wherein $A^1$ is hydrogen, halogen, or $C_1$-$C_3$ haloalkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$ or $C(O)$; and $Z^2$ is $C_1$-$C_4$ alkyl or $NR^3R^4$ and wherein $R^2$, $R^3$, and $R^4$ are each independently selected from hydrogen or $C_1$-$C_4$ alkyl.

In one embodiment, $X_1$ is hydrogen or $C_{1-4}$ alkyl; $X_2$ is hydrogen or $C_{1-4}$ alkyl; $X_3$ is hydrogen or halogen; and $X_4$ is hydrogen, $C_1$-$C_4$ alkyl, cyanoalkyl, or —$(CH_2)_p$C≡C$(CH_2)_t$H; W is C—R wherein R is H, F, Cl, or CN; $Q_1$ is hydrogen, halogen, $C_1$-$C_2$ alkyl or $C_1$-$C_2$ alkoxy; and $Q_2$ is $A^2$ and $Q_3$ is $A^1$, wherein $A^1$ is hydrogen, halogen, or $C_1$-$C_3$ haloalkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$ or $C(O)$; and $Z^2$ is $C_1$-$C_4$ alkyl or $NR^3R^4$ and wherein $R^2$, $R^3$, and $R^4$ are each independently selected from hydrogen or $C_1$-$C_4$ alkyl.

In one embodiment, $X_1$ is hydrogen or $C_{1-4}$ alkyl; $X_2$ is hydrogen or $C_{1-4}$ alkyl; $X_3$ is hydrogen or halogen; and $X_4$ is hydrogen, $C_1$-$C_4$ alkyl, cyanoalkyl, or —$(CH_2)_p$C≡C$(CH_2)_t$H; W is N; $Q_1$ is hydrogen, halogen, $C_1$-$C_2$ alkyl or $C_1$-$C_2$ alkoxy; $Q_2$ is $A^1$ and $Q_3$ is $A^2$, wherein $A^1$ is hydrogen, halogen, or $C_1$-$C_3$ alkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1: $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

In one embodiment, $X_1$ is hydrogen or $C_{1-4}$ alkyl; $X_2$ is hydrogen or $C_{1-4}$ alkyl; $X_3$ is hydrogen or halogen; and $X_4$ is hydrogen, $C_1$-$C_4$ alkyl, cyanoalkyl, or —$(CH_2)_p$C≡C$(CH_2)_t$H; W is C—R wherein R is H, F, Cl, or CN; $Q_1$ is hydrogen, halogen, $C_1$-$C_2$ alkyl or $C_1$-$C_2$ alkoxy; $Q_2$ is $A^1$ and $Q_3$ is $A^2$, wherein $A^1$ is hydrogen, halogen, or $C_1$-$C_3$ alkyl and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

In one embodiment, $X_1$ is methyl or ethyl; $X_2$ is hydrogen or methyl; $X_3$ is hydrogen; and $X_4$ is hydrogen, methyl, ethyl, isopropyl, cyanomethyl, or —$(CH_2)_p$C≡C$(CH_2)_t$H, wherein p is 1 and t is 0.; W is N, C—H, C—F, C—CN; $Q_1$ is hydrogen, chlorine, or methoxy; $Q_2$ is $A^1$ and $Q_3$ is $A^2$, wherein $A^1$ is hydrogen, methyl, or chlorine and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

In one embodiment, $X_1$ is methyl or ethyl; $X_2$ is hydrogen or methyl; $X_3$ is hydrogen; and $X_4$ is hydrogen, methyl, ethyl, isopropyl, cyanomethyl, or —$(CH_2)_p$C≡C$(CH_2)_t$H, wherein p is 1 and t is 0; W is C—H or C—F; $Q_1$ is hydrogen, chlorine, methyl, or methoxy; $Q_2$ is $A^1$ and $Q_3$ is $A^2$, wherein $A^1$ is hydrogen, methyl, or chlorine and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

In one embodiment, $X_1$ is methyl; $X_2$ is hydrogen; $X_3$ is hydrogen; and $X_4$ is methyl; W is C—H; $Q_1$ is hydrogen, methyl, chlorine, or methoxy; $Q_2$ is $A^1$ and $Q_3$ is $A^2$, wherein $A^1$ is hydrogen, methyl, or chlorine and $A^2$ is the group defined by -$(Z)_m$-$(Z^1)$-$(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

In a preferred embodiment, D is:

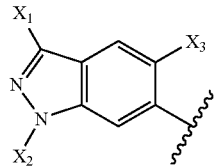

and $X_1$ is methyl; $X_2$ is hydrogen; $X_3$ is hydrogen; and $X_4$ is methyl; W is C—H; $Q_1$ is hydrogen, methyl, chlorine, or methoxy; $Q_2$ is $A^1$ and $Q_3$ is $A^2$, wherein $A^1$ is hydrogen, methyl, or chlorine and $A^2$ is the group defined by $-(Z)_m-(Z^1)-(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

In one embodiment, $X_1$ is methyl; $X_2$ is methyl; $X_3$ is hydrogen; and $X_4$ is methyl; W is C—H; $Q_1$ is hydrogen, chlorine, methyl, or methoxy; $Q_2$ is $A^1$ and $Q_3$ is $A^2$, wherein $A^1$ is hydrogen, methyl, or chlorine and $A^2$ is the group defined by $-(Z)_m-(Z^1)-(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

In another preferred embodiment, D is

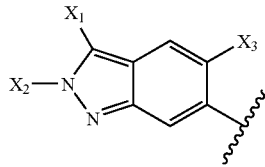

and $X_1$ is methyl; $X_2$ is methyl; $X_3$ is hydrogen; and $X_4$ is methyl; W is C—H; $Q_1$ is hydrogen, chlorine, methyl, or methoxy; $Q_2$ is $A^1$ and $Q_3$ is $A^2$, wherein $A^1$ is hydrogen, methyl, or chlorine and $A^2$ is the group defined by $-(Z)_m-(Z^1)-(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

In one embodiment, $X_1$ is methyl; $X_2$ is hydrogen; $X_3$ is hydrogen; and $X_4$ is methyl; W is C—F; $Q_1$ is hydrogen, chlorine, or methoxy; $Q_2$ is $A^1$ and $Q_3$ is $A^2$, wherein $A^1$ is hydrogen, methyl, or chlorine and $A^2$ is the group defined by $-(Z)_m-(Z^1)-(Z^2)$, wherein Z is $CH_2$ and m is 0, 1, 2, or 3, or Z is $NR^2$ and m is 0 or 1, or Z is $CH_2NR^2$ and m is 0 or 1; $Z^1$ is $S(O)_2$, and $S(O)$, or $C(O)$; and $Z^2$ is $C_1$-$C_4$ alkyl or $NR^3R^4$, and wherein $R^2$, $R^3$, and $R^4$ are each independently selected from hydrogen or $C_1$-$C_4$ alkyl.

Specific examples of compounds of the present invention include the following:

$N^2$-[5-(ethylsulfonyl)-2-methoxyphenyl]-5-fluoro-$N^4$-methyl-$N^4$-(3-methyl-1H-indazol-6-yl)-2,4-pyrimidinediamine;

3-({5-fluoro-4-[methyl(3-methyl-1H-indazol-6-yl)amino]-2-pyrimidinyl}amino)-4-methoxy-N-methylbenzenesulfonamide;

5-fluoro-$N^4$-methyl-$N^4$-(3-methyl-1H-indazol-6-yl)-$N^2$-{3-[(methylsulfonyl)methyl]phenyl}-2,4-pyrimidinediamine;

3-({5-fluoro-4-[methyl(3-methyl-1H-indazol-6-yl)amino]-2-pyrimidinyl}amino)-N-isopropylbenzenesulfonamide;

5-fluoro-$N^2$-[5-(isopropylsulfonyl)-2-methoxyphenyl]-$N^4$-methyl-$N^4$-(3-methyl-1H-indazol-6-yl)-2,4-pyrimidinediamine;

N-[5-({5-fluoro-4-[methyl(3-methyl-1H-indazol-6-yl)amino]-2-pyrimidinyl}amino)-2-methylphenyl]methanesulfonamide;

5-fluoro-$N^4$-methyl-$N^4$-(3-methyl-1H-indazol-6-yl)-$N^2$-[4-(methylsulfonyl)phenyl]-2,4-pyrimidinediamine;

$N^4$-(3-ethyl-1H-indazol-6-yl)-5-fluoro-$N^4$-methyl-$N^2$-{3-[(methylsulfonyl)methyl]phenyl}-2,4-pyrimidinediamine;

4-({5-fluoro-4-[methyl(3-methyl-1H-indazol-6-yl)amino]-2-pyrimidinyl}amino)benzenesulfonamide;

$N^4$-ethyl-5-fluoro-$N^2$-[2-methoxy-5-(methylsulfonyl)phenyl]-$N^4$-(3-methyl-1H-indazol-6-yl)-2,4-pyrimidinediamine;

[4-({5-fluoro-4-[methyl(3-methyl-1H-indazol-6-yl)amino]-2-pyrimidinyl}amino)phenyl]-N-methylmethanesulfonamide;

5-fluoro-$N^2$-{3-[(isopropylsulfonyl)methyl]phenyl}-$N^4$-methyl-$N^4$-(3-methyl-1H-indazol-6-yl)-2,4-pyrimidinediamine;

3-({5-fluoro-4-[methyl(3-methyl-1H-indazol-6-yl)amino]-2-pyrimidinyl}amino)-4-methoxybenzamide;

4-({5-fluoro-4-[methyl(3-methyl-1H-indazol-6-yl)amino]-2-pyrimidinyl}amino)-3-methoxybenzenesulfonamide;

$N^2$-(3-methyl-1H-indazol-6-yl)-$N^4$-{3-[(methylsulfonyl)methyl]phenyl}-1,3,5-triazine-2,4-diamine trifluoroacetate;

$N^2$-methyl-$N^2$-(3-methyl-1H-indazol-6-yl)-$N^4$-{3-[(methylsulfonyl)methyl]phenyl}-1,3,5-triazine-2,4-diamine;

$N^2$-[5-(ethylsulfonyl)-2-methoxyphenyl]-$N^4$-methyl-$N^4$-(3-methyl-1H-indazol-6-yl)-1,3,5-triazine-2,4-diamine;

N-[2-methyl-5-({4-[methyl(3-methyl-1H-indazol-6-yl)amino]-1,3,5-triazin-2-yl}amino)phenyl]methanesulfonamide;

$N^2$-methyl-$N^2$-(3-methyl-1H-indazol-6-yl)-$N^4$-[3-(methylsulfonyl)phenyl]-1,3,5-triazine-2,4-diamine;

N-[4-({4-[methyl(3-methyl-1H-indazol-6-yl)amino]-1,3,5-triazin-2-yl}amino)phenyl]acetamide;

3-({4-[methyl(3-methyl-1H-indazol-6-yl)amino]-2-pyrimidinyl}amino)benzenesulfonamide;

$N^2$-[5-(ethylsulfonyl)-2-methoxyphenyl]-$N^4$-methyl-$N^4$-(3-methyl-1H-indazol-6-yl)-2,4-pyrimidinediamine;

$N^4$-methyl-$N^4$-(3-methyl-1H-indazol-6-yl)-$N^2$-{3-[(methylsulfonyl)methyl]phenyl}-2,4-pyrimidinediamine;

N-isopropyl-3-({4-[methyl(3-methyl-1H-indazol-6-yl)amino]-2-pyrimidinyl}amino)benzenesulfonamide;

N-cyclopropyl-3-({4-[methyl(3-methyl-1H-indazol-6-yl)amino]-2-pyrimidinyl}amino)benzenesulfonamide;

$N^4$-ethyl-$N^2$-[5-(ethylsulfonyl)-2-methoxyphenyl]-$N^4$-(3-methyl-1H-indazol-6-yl)-2,4-pyrimidinediamine;

N-[3-({4-[methyl(3-methyl-1H-indazol-6-yl)amino]-2-pyrimidinyl}amino)phenyl]methanesulfonamide;

$N^2$-{3-[(isopropylsulfonyl)methyl]phenyl}-$N^4$-methyl-$N^4$-(3-methyl-1H-indazol-6-yl)-2,4-pyrimidinediamine;

$N^2$-{4-[(isopropylsulfonyl)methyl]phenyl}-$N^4$-methyl-$N^4$-(3-methyl-1H-indazol-6-yl)-2,4-pyrimidinediamine;

$N^2$-[5-(isobutylsulfonyl)-2-methoxyphenyl]-$N^4$-(3-methyl-1H-indazol-6-yl)-2,4-pyrimidinediamine;

N-[3-({4-[methyl(3-methyl-1H-indazol-6-yl)amino]-2-pyrimidinyl}amino)phenyl]acetamide;

N-[3-({4-[ethyl(3-methyl-1H-indazol-6-yl)amino]-2-pyrimidinyl}amino)phenyl]acetamide;
$N^2$-(2-methoxy-5-{[(5-methyl-3-isoxazolyl)methyl]sulfonyl}phenyl)-$N^4$-(3-methyl-1H-indazol-6-yl)-2,4-pyrimidinediamine;
4-methoxy-3-({4-[(3-methyl-1H-indazol-6-yl)amino]-2-pyrimidinyl}amino)benzenesulfonamide;
$N^2$-[5-(isopropylsulfonyl)-2-methoxyphenyl]-$N^4$-methyl-$N^4$-(3-methyl-1H-indazol-6-yl)-2,4-pyrimidinediamine;
$N^2$-[5-(ethylsulfonyl)-2-methoxyphenyl]-$N^4$-isopropyl-$N^4$-(3-methyl-1H-indazol-6-yl)-2,4-pyrimidinediamine;
$N^4$-(1H-indazol-6-yl)-$N^4$-methyl-$N^2$-{3-[(methylsulfonyl)methyl]phenyl}-2,4-pyrimidinediamine;
$N^4$-(1,3-dimethyl-1H-indazol-6-yl)-$N^4$-methyl-$N^2$-{3-[(methylsulfonyl)methyl]phenyl}-2,4-pyrimidinediamine;
$N^4$-(2,3-dimethyl-2H-indazol-6-yl)-$N^4$-methyl-$N^2$-{3-[(methylsulfonyl)methyl]phenyl}-2,4-pyrimidinediamine;
$N^4$-(2,3-dimethyl-2H-indazol-6-yl)-$N^2$-[5-(ethylsulfonyl)-2-methoxyphenyl]-$N^4$-methyl-2,4-pyrimidinediamine;
1-[4-methoxy-3-({4-[(3-methyl-1H-indazol-6-yl)amino]-2-pyrimidinyl}amino)phenyl]-1-propanone;
4-methoxy-N-[3-({4-[methyl(3-methyl-1H-indazol-6-yl)amino]-2-pyrimidinyl}amino)phenyl]benzenesulfonamide;
4-methoxy-N-methyl-3-({4-[(3-methyl-1H-indazol-6-yl)amino]-2-pyrimidinyl}amino)benzenesulfonamide;
[(3-methyl-1H-indazol-6-yl)(2-{4-[(methylsulfonyl)methyl]anilino}-4-pyrimidinyl)amino]acetonitrile;
[{2-[5-(ethylsulfonyl)-2-methoxyanilino]-4-pyrimidinyl}(3-methyl-1H-indazol-6-yl)amino]acetonitrile;
[(3-methyl-1H-indazol-6-yl)(2-{3-[(methylsulfonyl)methyl]anilino}-4-pyrimidinyl)amino]acetonitrile;
4-methoxy-N-methyl-3-({4-[methyl(3-methyl-1H-indazol-6-yl)amino]-2-pyrimidinyl}amino)benzenesulfonamide;
4-({4-[methyl(3-methyl-1H-indazol-6-yl)amino]-2-pyrimidinyl}amino)benzamide;
3-methoxy-4-({4-[methyl(3-methyl-1H-indazol-6-yl)amino]-2-pyrimidinyl}amino)benzenesulfonamide;
$N^4$-ethynyl-$N^4$-(3-methyl-1H-indazol-6-yl)-$N^2$-{3-[(methylsulfonyl)methyl]phenyl}-2,4-pyrimidinediamine;
3-({4-[(3-methyl-1H-indazol-6-yl)(2-propynyl)amino]-2-pyrimidinyl}amino)benzenesulfonamide;
4-({4-[methyl(3-methyl-1H-indazol-6-yl)amino]-2-pyrimidinyl}amino)benzenesulfonamide;
$N^4$-methyl-$N^4$-(3-methyl-1H-indazol-6-yl)-$N^2$-[3-(methylsulfonyl)phenyl]-2,4-pyrimidinediamine;
4-methoxy-3-({4-[methyl(3-methyl-1H-indazol-6-yl)amino]-2-pyrimidinyl}amino)benzenesulfonamide;
$N^2$-[5-(ethylsulfonyl)-2-methoxyphenyl]-$N^4$-(3-methyl-1H-indazol-6-yl)-2,4-pyrimidinediamine;
3-({4-[methyl(3-methyl-1H-indazol-6-yl)amino]-2-pyrimidinyl}amino)benzamide;
$N^2$-[4-(ethylsulfonyl)phenyl]-$N^4$-methyl-$N^4$-(3-methyl-1H-indazol-6-yl)-2,4-pyrimidinediamine;
N-[4-({4-[methyl(3-methyl-1H-indazol-6-yl)amino]-2-pyrimidinyl}amino)benzyl]ethanesulfonamide;
N-[3-({4-[methyl(3-methyl-1H-indazol-6-yl)amino]-2-pyrimidinly}amino)benzyl]methanesulfonamide;
2-chloro-5-({4-[methyl(3-methyl-1H-indazol-6-yl)amino]-2-pyrimidinyl}amino)benzenesulfonamide;
2-chloro-4-({4-[methyl(3-methyl-1H-indazol-6-yl)amino]-2-pyrimidinyl}amino)benzenesulfonamide;
4-chloro-3-({4-[methyl(3-methyl-1H-indazol-6-yl)amino]-2-pyrimidinyl}amino)benzenesulfonamide;
3-methyl-4-({4-[methyl(3-methyl-1H-indazol-6-yl)amino]-2-pyrimidinyl}amino)benzenesulfonamide;
2-methyl-5-({4-[methyl(3-methyl-1H-indazol-6-yl)amino]-2-pyrimidinyl}amino)benzenesulfonamide;
4-methyl-3-({4-[methyl(3-methyl-1H-indazol-6-yl)amino]-2-pyrimidinyl}amino)benzenesulfonamide;
$N^4$-methyl-$N^4$-(3-methyl-1H-indazol-6-yl)-$N^2$-[3-(methylsulfinyl)phenyl]-2,4-pyrimidinediamine;
$N^2$-[2-fluoro-5-(methylsulfonyl)phenyl]-$N^4$-methyl-$N^4$-(3-methyl-1H-indazol-6-yl)-2,4-pyrimidinediamine;
$N^2$-[2-methoxy-5-(methylsulfonyl)phenyl]-$N^4$-methyl-$N^4$-(3-methyl-1H-indazol-6-yl)-2,4-pyrimidinediamine;
5-({4-[(2,3-dimethyl-2H-indazol-6-yl)(methyl)amino]pyrimidin-2-yl}amino)-2-methylbenzenesulfonamide;
3-({4-[(2,3-dimethyl-2H-indazol-6-yl)(methyl)amino]pyrimidin-2-yl}amino)benzenesulfonamide;
2-[4-({4-[(2,3-dimethyl-2H-indazol-6-yl)(methyl)amino]pyrimidin-2-yl}amino)phenyl]ethanesulfonamide;
$N^4$-(2,3-dimethyl-2H-indazol-6-yl)-$N^4$-methyl-$N^2$-{4-[(methylsulfonyl)methyl]phenyl}pyrimidine-2,4-diamine;
3-({4-[[3-(hydroxymethyl)-2-methyl-2H-indazol-6-yl](methyl)amino]pyrimidin-2-yl}amino)benzenesulfonamide;
3-({4-[(1,2-dimethyl-1H-benzimidazol-5-yl)(methyl)amino]pyrimidin-2-yl}amino)benzenesulfonamide;
3-({4-[(2-benzyl-1-methyl-1H-benzimidazol-5-yl)(methyl)amino]pyrimidin-2-yl}amino)benzenesulfonamide;
3-({4-[(2-ethyl-3-methyl-2H-indazol-6-yl)(methyl)amino]pyrimidin-2-yl}amino)benzenesulfonamide;
3-({4-[[2-(3-chlorobenzyl)-3-methyl-2H-indazol-6-yl](methyl)amino]pyrimidin-2-yl}amino)benzenesulfonamide;
3-({4-[(2,3-dimethyl-2H-indazol-6-yl)(methyl)amino]-1,3,5-triazin-2-yl}amino)benzenesulfonamide; and
5-({4-[(2,3-dimethyl-2H-indazol-6-yl)(methyl)amino]-1,3,5-triazin-2-yl}amino)-2-methylbenzenesulfonamide;

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, of a compound of the formula (I) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable salt or solvate thereof, or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula (I) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula I include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine and thioguanine; and camptothecins such as 9-amino camptothecin, irinotecan, CPT-11 and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; cyclooxygenase type 2 (COX-2) inhibitors such as celecoxib; other angiogenic inhibiting agents such as VEGFR inhibitors other than those described herein and TIE-2 inhibitors; growth factor function inhibitors such as inhibitors of the functions of hepatocyte growth factor; erb-B2, erb-B4, epidermal growth factor receptor (EGFr), platelet derived growth factor receptor (PDGFr), vascular endothelial growth factor receptor (VEGFR) other than those described in the present invention, and TIE-2; and other tyrosine kinase inhibitors such as cyclin dependent inhibitors such as CDK2 and CDK4 inhibitors.

The compounds of formula (I) and salts, solvates and physiological functional derivatives thereof, are believed to have anticancer activity as a result of inhibition of the protein kinase VEGFR2 and its effect on selected cell lines whose growth is dependent on VEGFR2 protein kinase activity.

The present invention thus also provides compounds of formula (I) and pharmaceutically acceptable salts or solvates thereof, or physiologically functional derivatives thereof, for use in medical therapy, and particularly in the treatment of disorders mediated by inappropriate VEGFR2 activity.

The inappropriate VEGFR2 activity referred to herein is any VEGFR2 activity that deviates from the normal VEGFR2 activity expected in a particular mammalian subject. Inappropriate VEGFR2 activity may take the form of, for instance, an abnormal increase in activity, or an aberration in the timing and or control of VEGFR2 activity. Such inappropriate activity may result then, for example, from overexpression or mutation of the protein kinase or ligand leading to inappropriate or uncontrolled activation of the receptor. Furthermore, it is also understood that unwanted VEGFR2 activity may reside in an abnormal source, such as a malignancy. That is, the level of VEGFR2 activity does not have to be abnormal to be considered inappropriate, rather the activity derives from an abnormal source. In a like manner, the inappropriate angiogenesis referred to herein is any angiogenic activity that deviates from the normal angiogenic activity expected in a particular mammalian subject. Inappropriate angiogenesis may take the form of, for instance, an abnormal increase in activity, or an aberration in the timing and or control of angiogenic activity. Such inappropriate activity may result then, for example, from overexpression or mutation of a protein kinase or ligand leading to inappropriate or uncontrolled activation of angiogenesis. Furthermore, it is also understood that unwanted angiogenic activity may reside in an abnormal source, such as a malignancy. That is, the level of angiogenic activity does not have to be abnormal to be considered inappropriate, rather the activity derives from an abnormal source.

The present invention is directed to methods of regulating, modulating, or inhibiting VEGFR2 for the prevention and/or treatment of disorders related to unregulated VEGFR2 activity. In particular, the compounds of the present invention can also be used in the treatment of certain forms of cancer. Furthermore, the compounds of the present invention can be used to provide additive or synergistic effects with certain existing cancer chemotherapies and radiation, and/or be used to restore effectiveness of certain existing cancer chemotherapies and radiation.

The compounds of the present invention are also useful in the treatment of one or more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

A further aspect of the invention provides a method of treatment of a mammal suffering from a disorder mediated by inappropriate VEGFR2 activity, including susceptible malignancies, which includes administering to said subject an effective amount of a compound of formula (I) or a pharmaceutically acceptable salt, solvate, or a physiologically functional derivative thereof. In a preferred embodiment, the disorder is cancer.

A further aspect of the invention provides a method of treatment of a mammal suffering from cancer, which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by inappropriate VEGFR2 activity. In a preferred embodiment, the disorder is cancer.

A further aspect of the present invention provides the use of a compound of formula (I), or a pharmaceutically acceptable salt or solvate thereof, or a physiologically functional derivative thereof, in the preparation of a medicament for the treatment of cancer and malignant tumours.

The mammal requiring treatment with a compound of the present invention is typically a human being.

In another embodiment, therapeutically effective amounts of the compounds of formula (I) or salts, solvates or physiologically derived derivatives thereof and agents which inhibit growth factor receptor function may be administered in combination to a mammal for treatment of a disorder mediated by inappropriate VEGFR2 activity, for instance in the treatment of cancer. Such growth factor receptors include, for example, EGFR, PDGFR, erbB2, erbB4, VEGFR, and/or TIE-2. Growth factor receptors and agents that inhibit growth factor receptor function are described, for instance, in Kath, John C., Exp. Opin. Ther. Patents (2000) 10(6):803-818 and in Shawver et al. DDT Vol 2, No. 2 February 1997.

The compounds of the Formula (I) or salts, solvates, or physiologically functional derivatives thereof and the agent for inhibiting growth factor receptor function may be employed in combination concomitantly or sequentially in any therapeutically appropriate combination. The combination may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

In another aspect of the present invention, there is provided a method of treating a disorder in a mammal, said disorder being mediated by inappropriate angiogenesis, including: administering to said mammal a therapeutically effective amount of a compound of formula (I), or a salt, solvate or physiologically functional derivative thereof. In one embodiment, the inappropriate angiogenic activity is due to at least one of inappropriate VEGFR1, VEGFR2, VEGFR3, or TIE-2 activity. In another embodiment, the inappropriate angiogenesis is due to inappropriate VEGFR2 and TIE-2 activity. In a further embodiment, the method further includes administering a therapeutically effective amount of a TIE-2 inhibitor along with the compounds of formula (I) or salts, solvates or physiologically functional derivatives thereof. Preferably the disorder is cancer.

In another aspect of the present invention, there is provided the use of a compound of formula (I), or a salt, solvate or physiologically functional derivative thereof in the preparation of a medicament for use in treating a disorder in a mammal, said disorder being characterized by inappropriate angiogenesis. In one embodiment, the inappropriate angiogenic activity is due to at least one of inappropriate VEGFR1, VEGFR2, VEGFR3 or TIE-2 activity. In another embodiment, the inappropriate angiogenic activity is due to inappropriate VEGFR2 and TIE-2 activity. In a further embodiment, the use further includes use of a TIE-2 inhibitor to prepare said medicament.

The combination of a compound of formula (I) or salts, solvates, or physiologically functional derivatives with a TIE-2 inhibitor may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Compounds of general formula (I), (II), (III), and (IV) may be prepared by methods known in the art of organic synthesis as set forth in part by the following synthesis schemes. Generally, the following schemes are illustrated using compounds of formula (II), but it is recognized that such schemes are easily adaptable by the skilled artisan to prepare compounds of formula (I), including compounds of formula (III) and (IV). It is also recognized that in all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of formula (II), wherein W is C—H, can be prepared according to the synthetic sequence shown in Scheme 1 and further detailed in the Examples section following. Typically 2,4-Dichloropyrimidine (1) undergoes a displacement reaction at C4 with an appropriate aminoindazole (A) to provide the 2-chloro-4-arylaminopyrimidine derivative (B). For compounds of formula (II), wherein $X_4$ is hydrogen, a further displacement at C2 is carried out with an appropriate arylamine (C) to provide the compound of Formula (II), wherein $X_4$ is hydrogen. Alternatively, for compounds of Formula (II), wherein $X_4$ is not hydrogen, chloropyrimidine B is treated with di-t-butyl-dicarbonate to affect BOC protection at N1 of the indazole (Scheme 2). Subsequent N-alkylation under standard conditions affords the $N^4$-alkyl-2-chloropyrimidine D, which is treated with an arylamine C in a similar fashion as above to provide the compound of Formula (II), wherein $X_4$ is not hydrogen. In exceptional cases, BOC deprotection is not fully facilitated in the displacement reaction and the initial reaction product is further exposed to TFA or HCl to afford the desired product.

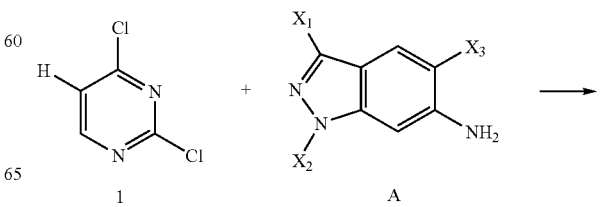

SCHEME 1

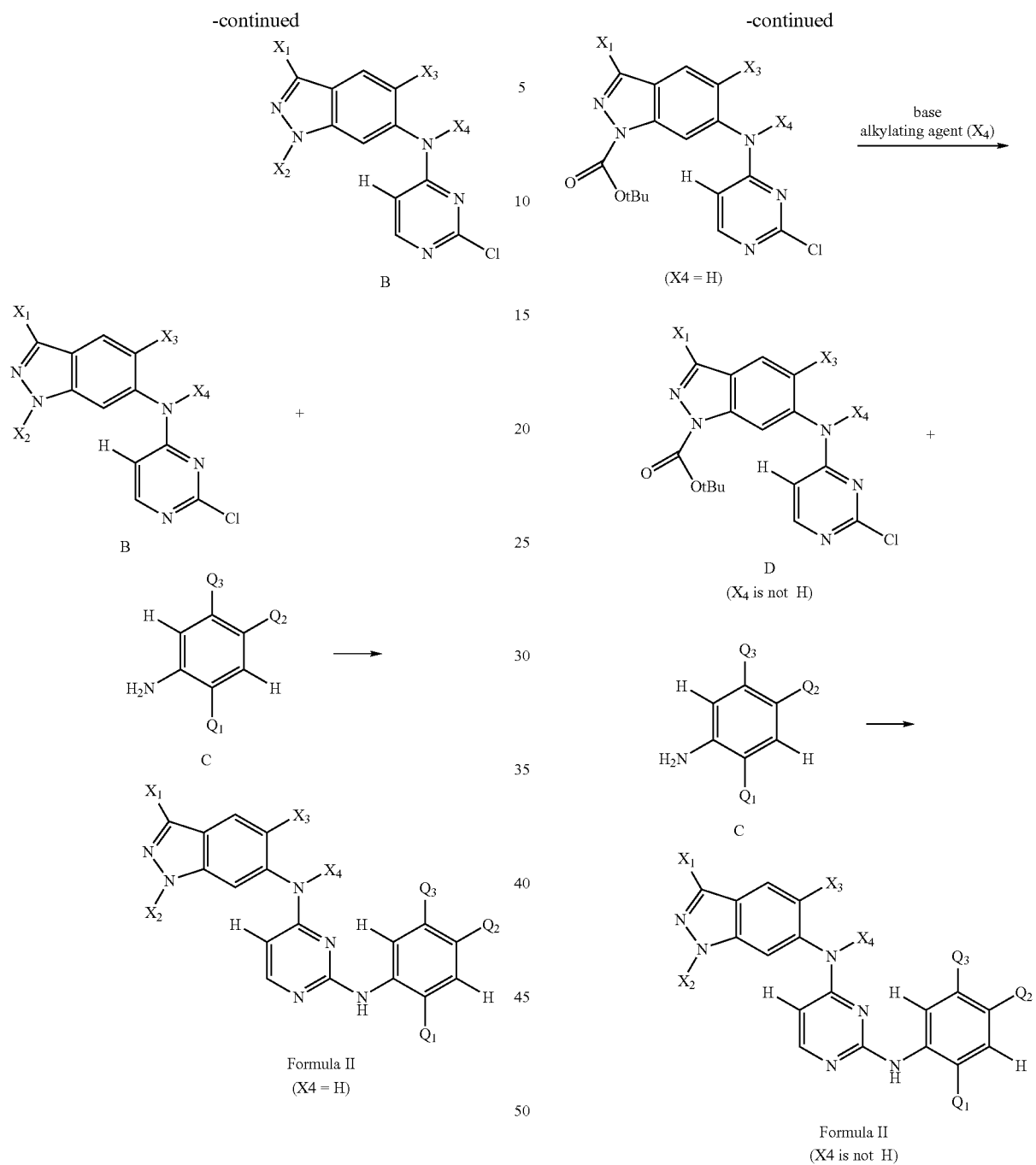

Compounds of Formula (II), wherein W is C—F, can be prepared according to the synthetic sequence shown in Scheme 3 and further detailed in the Examples section following. 5-Fluorouracil (2) is converted to 5-fluoro-2,4-dichloropyrimidine (3) by treatment with $POCl_3$. The remaining steps in the synthesis of compounds of Formula (II), wherein W is C—F, are parallel to those described above in Scheme 1 and/or Scheme 2. Compounds of formula (III), wherein W is C—F, can be prepared by using 5-fluoro-2,4-dichloropyrimidine (3) with appropriate adaptation of Scheme 10 following, such adaptation being within the purview of those skilled in the art.

SCHEME 2

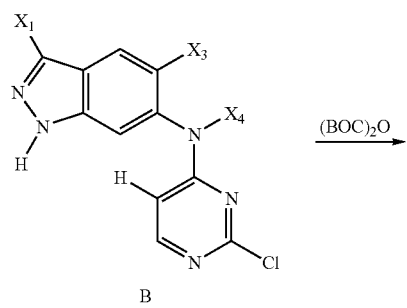

SCHEME 3

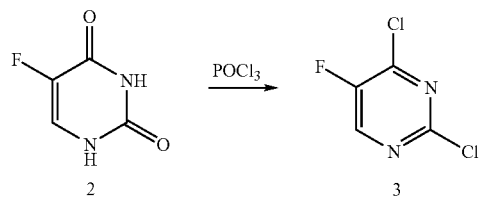

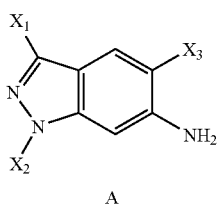

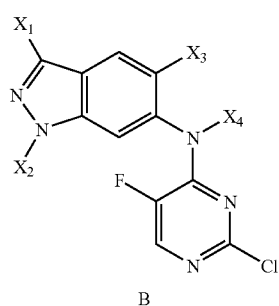

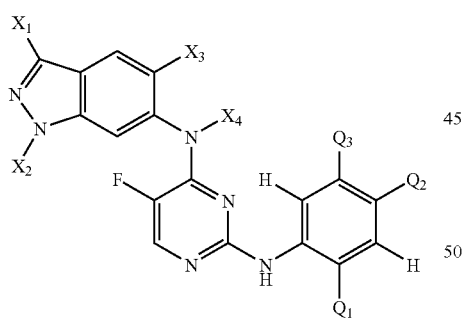

Formula II

Compounds of Formula (II), wherein W is N, can be prepared according to the synthetic sequence shown in Scheme 4 and further detailed in the Examples section following. 2,4-Dichloro-1,3,5-triazine (4) is treated with an arylamine C in a suitable solvent (e.g., $CH_3CN$) to afford the a chlorotriazine E. Compound E is further treated with arylamine A ($X_4$ is H or alkyl) to provide the compound of Formula (II). Compounds of formula (III), wherein W is N, can be prepared by using 2,4-Dichloro-1,3,5-triazine (4) with appropriate adaptation of Scheme 10 following, such adaptation being within the purview of those skilled in the art.

SCHEME 4

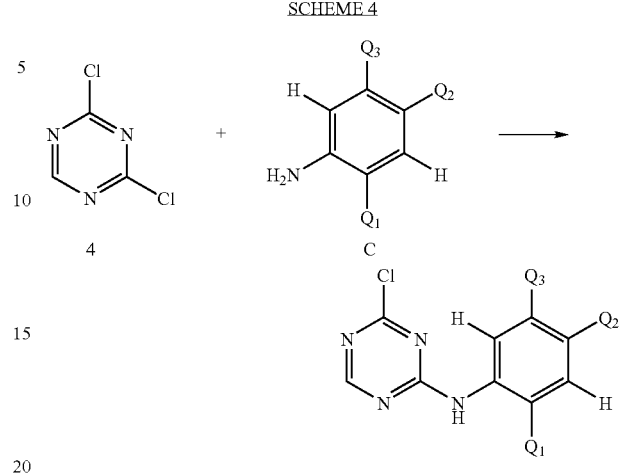

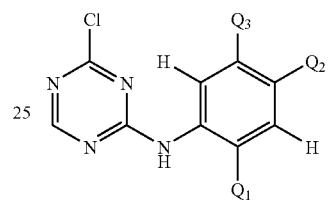

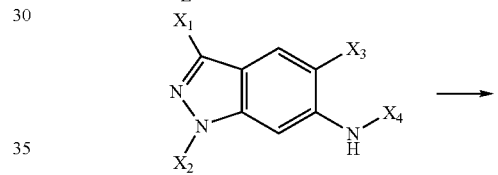

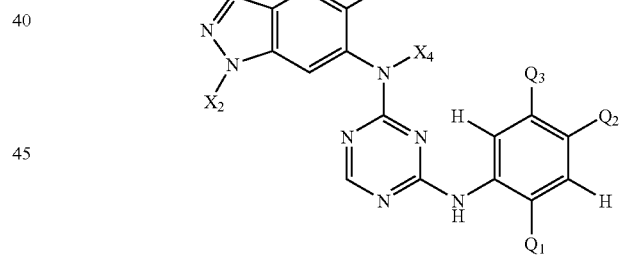

Formula II

The aniline moieties of Formula (I), depicted as structure C in Schemes 1, 2 and 4 above, are available through multi-step organic synthesis familiar to one who is skilled in the art. The following schemes illustrate the methods that can be used to derive the anilines of structure C, which are incorporated into compounds of Formula (I) of the present invention.

As shown in Scheme 5, the appropriately substituted meta- or para-$NO_2$ benzylamine can be condensed with an alkyl- or arylsulfonyl chloride under suitable conditions (e.g., triethylamine, $CH_2Cl_2$) to provide a sulfonamide F. The $NO_2$ moiety of F can be reduced using $SnCl_2$/conc. HCl or by hydrogenation (e.g., 10% Pd/C in methanol) to provide the desired aniline. Other embodiments of the present invention can be derived from anilines that are prepared as shown in Scheme 6. A nitro-substituted benzyl chloride G is converted to a sodium benzylsulfonate salt H by reaction at elevated temperature with Na$_2$SO$_3$ in a H$_2$O/dioxane mixture. Treatment of H with SOCl$_2$ (cat. DMF/CH$_2$Cl$_2$) provides the corresponding sulfonylchloride I, which can be treated with an amine to provide a sulfonamide J. Reduction of the nitro group in J can be accomplished in similar fashion as described above in Scheme 5.

Formula (I). An appropriate thiolate anion undergoes a displacement reaction with a nitro-substituted benzyl chloride G to provide a benzylic sulfide K. Oxidation of the sulfide, for example with mCPBA, provides the corresponding sulfone, which is then reduced by standard methods to the desired aniline C.

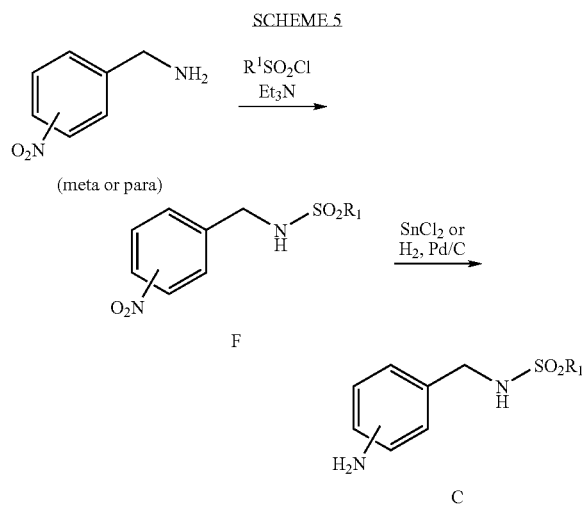

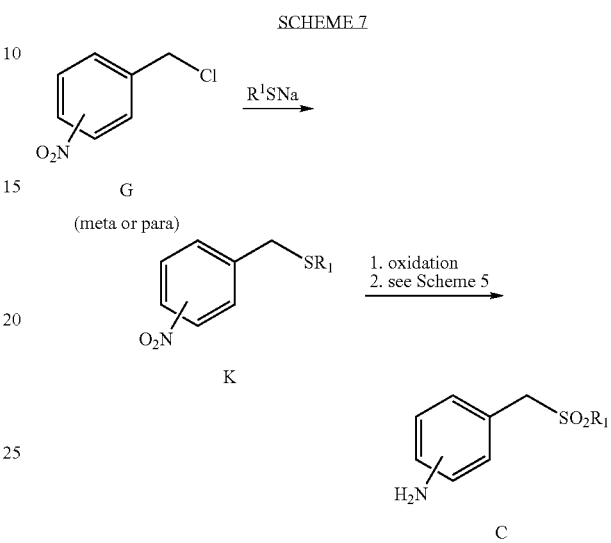

Scheme 8 depicts the synthesis of other anilines of structure C that are useful in the preparation of compounds of Formula (I). The 2-methoxyacetanilide undergoes chlorosulfonylation under standard conditions to provide the expected arylsulfonyl chloride L. Amination of L with an amine affords a sulfonamide, which is hydrolyzed under appropriate conditions to provide the desired aniline C for use in the synthesis of compounds of Formula (I).

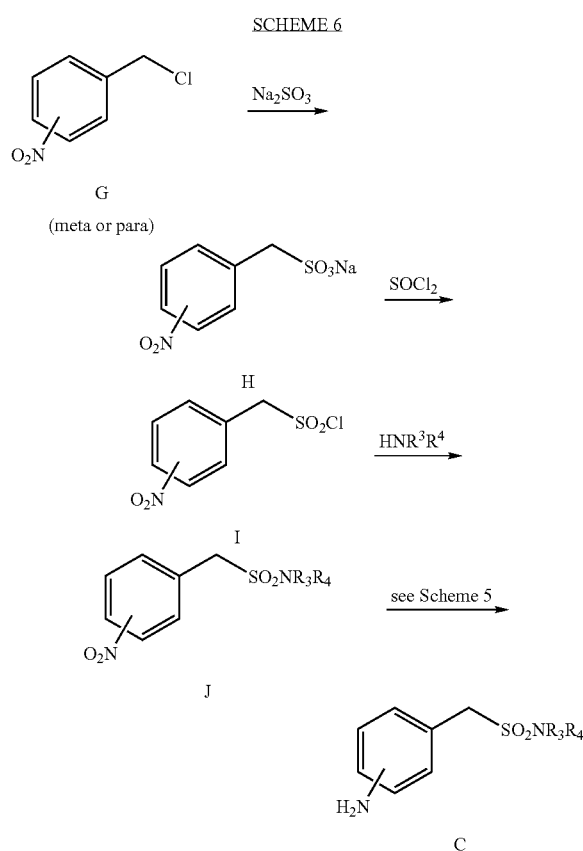

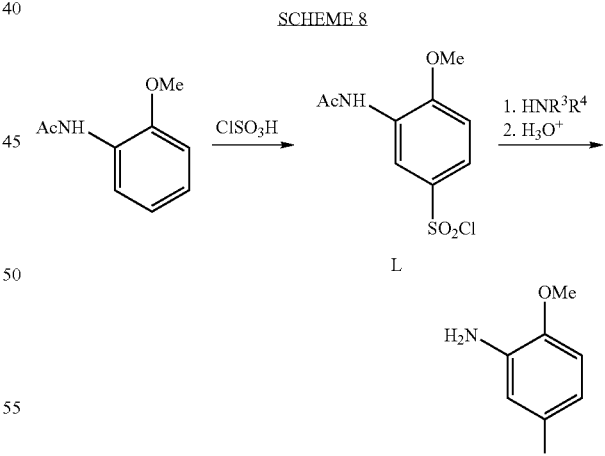

Scheme 7 depicts the synthesis of other anilines of structure C that are useful in the preparation of compounds of Scheme 9 depicts the synthesis of other anilines of structure C that are useful in the preparation of compounds of Formula (I). The para-methoxy sulfenimide M can be prepared as described in the prior art. Mitsunobu-type substitution with an alcohol provides the phenyl sulfide N. (In certain cases, one who is skilled in the art will recognize that the same phenylsulfide N can be derived by alkylation of the para-methoxy thiophenoxide anion with an alkyl halide.) Oxidation of sulfide N affords a sulfone O, which undergoes nitration to provide the methoxynitrosulfone P. Methoxynitrosulfone P is reduced as already described by the earlier scheme to the aniline C.

SCHEME 9

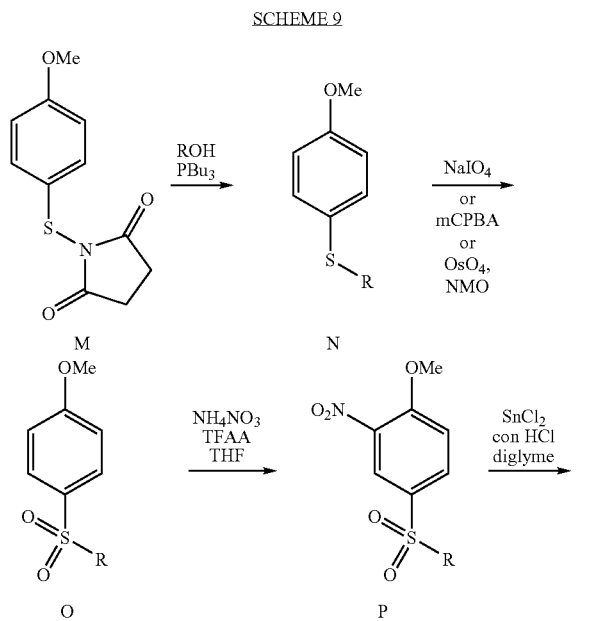

Scheme 10 depicts the synthesis of compounds of Formula (III). A substituted 6-nitroindazole Q undergoes alkylation by an appropriate alkylating agent (e.g., trimethyloxonium tetraflouroborate, triethyloxonium tetrafluoroborate, benzyl halide) to provide the N2-alkylated nitroindazole R. Reduction of the nitro group using standard conditions (e.g., $SnCl_2$, aqueous acid or 10% Pd/C, methanol, ammonium formate) followed by condensation with 2,4-dichloropyrimidine provides the chloropyrimidine S. Alkylation of the bisaryl amine nitrogen under appropriate alkylation conditions (e.g., MeI, $Cs_2CO_3$, DMF) affords intermediate T, which undergoes subsequent condensation with an appropriately substituted aniline to provide the compound of Formula (III).

SCHEME 10

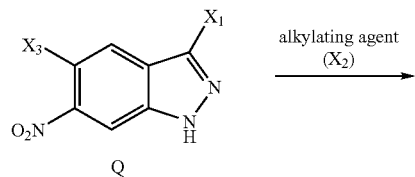

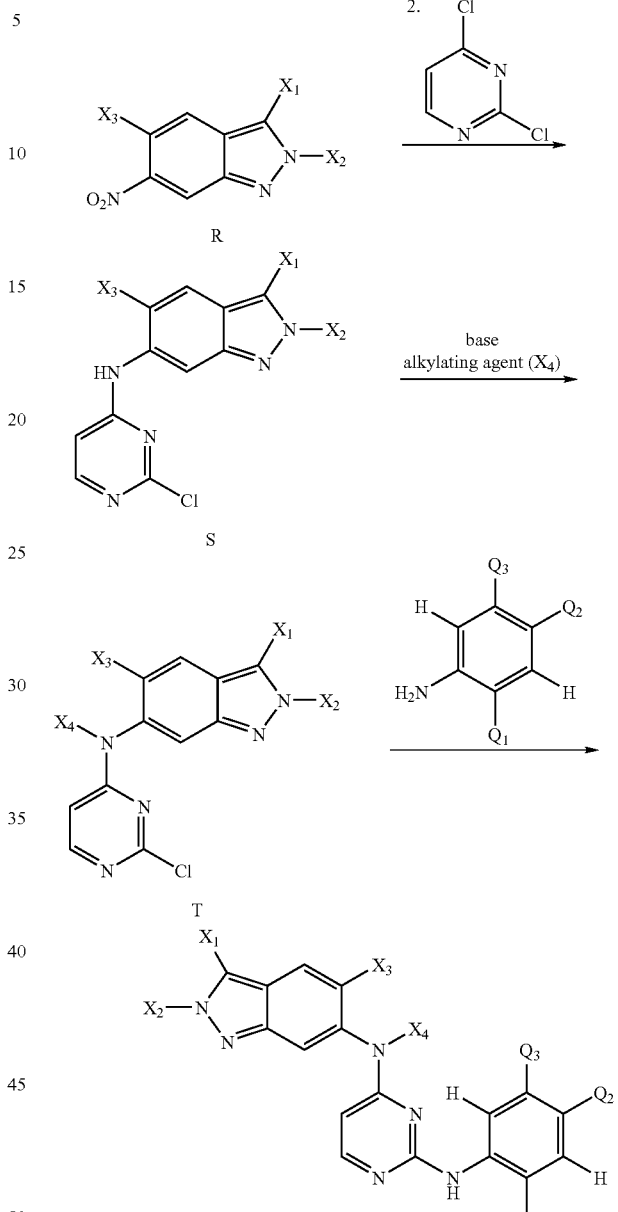

Formula III

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i. v. (intravenous); Hz (Hertz);
MHz (megahertz); mol (moles);
mmol (millimoles); RT (room temperature);
min (minutes); h (hours);
mp (melting point); TLC (thin layer chromatography);
$T_r$ (retention time); RP (reverse phase);
MeOH (methanol); I-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); (CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid; EDC (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); Me (methyl);
OMe (methoxy); Et (ethyl);
HPLC (high pressure liquid chromatography);
BOP (bis(2-oxo-3-oxazolidinyl)phosphinic chloride);
TBAF (tetra-n-butylammonium fluoride);
Et (ethyl); tBu (tert-butyl).

All references to ether are to diethyl ether; brine refers to a saturated aqueous solution of NaCl. Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck). Optical rotations were obtained using a Perkin Elmer Model 241 Polarimeter. Melting points were determined using a Mel-Temp II apparatus and are uncorrected.

The following examples describe the syntheses of intermediates particularly useful in the synthesis of compounds of Formula (I), (II), (III), and (IV):

Intermediate Example 1

Preparation of 3-methyl-1H-indazol-6-amine

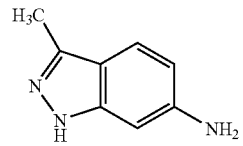

To a solution of 10 g (0.06 mol) of 2-ethyl-5-nitroaniline (prepared by nitration of 2-ethylaniline: Bergman and Sand, *Tetrahedron* 1990, 46, 6085-6112) in 300 ml of glacial acetic acid, at room temperature, was added a solution of 8.98 ml (0.06 mol) of tert-butyl nitrite in 40 ml of acetic acid dropwise over 15 min. After the addition was complete the solution was allowed to stir for 30 min. The acetic acid was removed in vacuo to afford an orange solid. The solid was dissolved in approximately 120 ml of ethyl acetate and washed with 3×100 ml sat. aqueous NaHCO$_3$. The organic layer was dried over MgSO$_4$ and the solvent was removed in vacuo to afford 3-methyl-6-nitroindazole as a yellow solid (10.4 g, 98%).

To a stirred solution of 10 g (0.06 mol) of 3-methyl-6-nitroindazole in 100 ml of 2-methoxyethyl ether, at 0° C., was added a solution of 45 g (0.24 mol) of tin(II)chloride in 86 ml of concentrated HCl dropwise over 15 min, in order to keep the reaction temperature below 100° C. After the addition was complete, the ice bath was removed and the solution was allowed to stir for an additional 20 min. Approximately 70 ml of diethyl ether was added to reaction, resulting in precipitate formation. The resulting precipitate was isolated by filtration and washed with diethyl ether, and afforded a yellow solid (10 g, 92%), the HCl salt of 3-methyl-1H-indazol-6-amine.

Intermediate Example 2

Preparation of N, 3-dimethyl-1H-indazol-6-amine

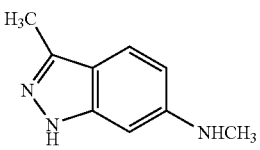

To a 100-mL flask containing 1.88 g (34.8 mmol) sodium methoxide and 60 mL of dry methanol was added 1.27 g (6.96 mmol) of 3-methyl-1H-indazol-6-amine hydrochloride. After stirring the mixture at room temperature for 15 minutes, 0.38 g (12.6 mmol) of paraformaldehyde was added and the flask placed into a 60° C. oil bath for 10 minutes. The flask was then removed from the oil bath and allowed to stir at room temperature for 4.5 hours. To the reaction mixture was added 0.26 g (6.96 mmol) of sodium borohydride and the mixture heated to reflux for 2 hours then allowed to cool to room temperature and stir overnight. To the reaction mixture was added 1M sodium hydroxide (13 mL). After 10 minutes the reaction mixture was concentrated in vacuo to an aqueous suspension. The suspension was diluted with 40 mL of water and pH adjusted to pH 8 with aq. hydrochloric acid. The aqueous suspension was extracted three times with ethyl acetate, and the organic extracts combined and washed with brine, dried with sodium sulfate, and filtered. To the filtrate was added 5 g of silica gel and the resultant suspension concentrated to dryness in vacuo. The solid was loaded on top of a column of 90 g of silica gel and eluted with chloroform/ethyl acetate/methanol (9:0.5:0.5). The proper fractions were combined and concentrated to give 0.43 g (39%) of N, 3-dimethyl-1H-indazol-6-amine as a white solid.

HNMR: δ 11.88 (s, 1H), 7.29 (d, 1H), 6.44 (d, 1H), 6.20 (s, 1H), 5.80 (brs, 1H), 2.67 (s, 3H) 2.32 (s, 3H); MS (ES+, m/z) 162 (M+H).

Intermediate Example 3

Preparation of 2,4-Dichloro-5-fluoropyrimidine

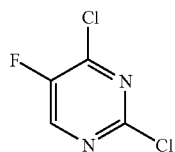

To 5-fluorouracil (5.0 g, 0.04 mol) was added phosphorus oxychloride (25 mL, 0.27 mol) and N,N-diethylaniline (6 mL, 0.06 mol) while stirring at room temperature. After being heated under reflux for 100 min, the mixture was concentrated under reduced pressure. The residue was poured into ice water (100 mL) and extracted with ether. The organic layer was dried with sodium sulfate and evaporated at 0° C. under reduced pressure to give 5.35 g of the desired product (85%). Mp 37-38° C. HNMR: δ 8.95 (s, 1H).

Intermediate Example 4

Preparation of N-(2-chloro-5-fluoro-4-pyrimidinyl)-N-(3-methyl-1H-indazol-6-yl)amine

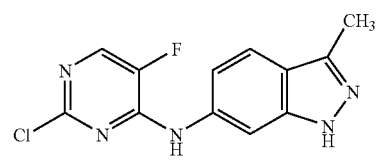

To a stirred solution of 3-methyl-6-aminoindazole (2.71 g, 0.015 mol) and NaHCO₃ (1.26 g, 0.045 mol) in THF (15 mL) and EtOH (60 mL) was added 5-fluoro-2,4-dichloropyrimidine (3.2 g, 0.019 mol) at room temperature. After the reaction was stirred overnight, the brown suspension was filtered and washed thoroughly with EtOH. The filtrate was concentrated under reduced pressure, and the resulting solid was washed with ether to remove excess pyrimidine to yield 3.7 g of the desired product (89%). HNMR: δ 12.57 (s, 1H), 10.01 (s, 1H), 8.28 (d, 1H), 7.93 (s, 1H), 7.60 (d, 1H), 7.27 (dd, 1H) 3.11 (s, 3H).

Intermediate Example 5

Preparation of N-(2-chloro-5-4-pyrimidinyl)-N-(3-methyl-1H-indazol-6-yl)amine

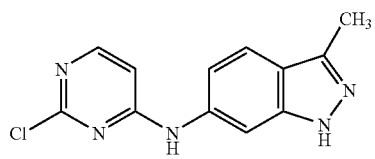

To a stirred solution of 3-methyl-6-aminoindazole (2.71 g, 0.015 mol) and NaHCO₃ (1.26 g, 0.045 mol) in THF (15 mL) and ethanol (60 mL) was added 2,4-dichloropyrimidine (6.66 g, 0.045 mol) at room temperature. After the reaction was stirred for four hours, the suspension was filtered and washed thoroughly with ethanol. The filtrate was concentrated under reduced pressure, and the resulting solid was washed with ether to remove excess pyrimidine to yield 3.5 g (89% yield) of N-(2-chloro-4-pyrimidinyl)-N-(3-methyl-1H-indazol-6-yl)amine.

Intermediate Example 6

Preparation of tert-butyl 6-[(2-chloro-5-fluoro-4-pyrimidinyl)amino]-3-methyl-1H-indazole-1-carboxylate

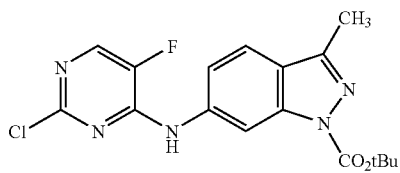

To a stirred suspension of the product of intermediate example 4 (3.0 g, 0.011 mol), triethylamine (1.5 mL, 0.011 mol), 4-dimethylaminopyridine (0.13 g, 0.11 mmol), and acetonitrile (14 mL) was added DMF (50 mL) at room temperature. Once the mixture was in solution, di-tert-butyl dicarbonate (2.36 g, 0.011 mol) was added portion wise over three minutes. After being stirred for 1 hour, the solution was diluted with water and extracted with ether (3×40 mL). The combined extracts were dried over sodium sulfate, filtered, and concentrated under reduced pressure. The resulting residue was purified by silica gel column chromatography (9:1, CH₂Cl₂:EtOAc), giving 3.3 grams of the desired product (85%).

Intermediate Example 7

Preparation of tert-butyl 6-[(2-chloro-4-pyrimidinyl)amino]-3-methyl-1H-indazole-1-carboxylate

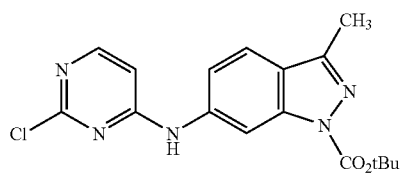

To a stirred suspension of N-(2-chloro-4-pyrimidinyl)-N-(3-methyl-1H-indazol-6-yl)amine (2.8 g, 0.011 mol), triethylamine (1.5 mL, 0.011 mol), 4-dimethylaminopyridine (0.13 g, 0.11 mmol), and acetonitrile (14 mL) was added DMF (50 mL) at room temperature. Once the mixture is in solution, di-tert-butyl dicarbonate (2.36 g, 0.011 mol) was added portionwise over three minutes. After being stirred for 1 hour, the solution was diluted with water and extracted with ether (3×40 mL). The combined extracts were dried over sodium sulfate, filtered, and concentrated under reduced pressure. The resulting residue was purified by column chromatography (silica gel, 9:1 $CH_2Cl_2$-EtOAc), giving 3.3 grams (85% yield) of tert-butyl 6-[(2-chloro-4-pyrimidinyl)amino]-3-methyl-1H-indazole-1-carboxylate.

Intermediate Example 8

Preparation of tert-butyl 6-[(2-chloro-5-fluoro-4-pyrimidinyl)(methyl)amino]-3-methyl-1H-indazole-1-carboxylate

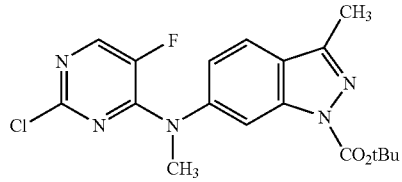

To a stirred solution of the product of Intermediate Example 6 (3.3 g, 8.8 mmol) in 44 mL of DMF was added NaH (0.23 g, 9.6 mmol) portion wise over 3 min at room temperature. After being stirred for 15 min, iodomethane (1.37 g, 9.6 mmol) was added dropwise. After being stirred for 30 min, the reaction was quenched with water and extracted with ether (3×30 mL). The combined extracts were dried over sodium sulfate, filtered, and concentrated under reduced pressure to yield a yellow solid. The resulting solid was purified by silica gel column chromatography ($CH_2Cl_2$), giving 3.26 g of the desired product (95%).

HNMR: δ 8.18 (d, 1H), 7.90 (s, 1H), 7.82 (d, 1H), 7.35 (d, 1H), 3.45 (s, 3H), 2.48 (s, 3H) 1.54 (s, 9H). MS (ES+, m/z) 292 (M+H).

Intermediate Example 9

Preparation of tert-butyl 6-[(2-chloro-4-pyrimidinyl)(methyl)amino]-3-methyl-1H-indazole-1-carboxylate

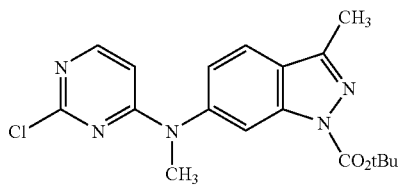

This intermediate wherein W═H was prepared in similar fashion to Intermediate Example 8 described above.

Intermediate Example 10

Preparation of 4-Chloro-N-{3-[(methylsulfonyl)methyl]phenyl}-1,3,5-triazin-2-amine

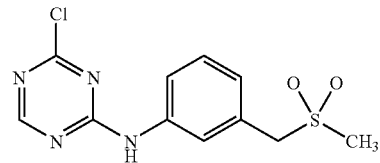

To a dry flask containing a magnetic stir bar and a nitrogen atmosphere was added 0.247 g (1.33 mmol) of 3-[(methylsulfonyl)methyl]aniline, 2 mL dry acetonitrile and 0.23 mL (1.3 mmol) of diisopropylethyl amine and resultant mixture cooled in an ice bath. To the cold solution was added a solution of 0.2 g (1.33 mmol) of 2,4-dichloro-1,3,5-triazine in 2.4 mL of dry acetonitrile over 1 min. The reaction mixture was stirred for ca. 16 hrs and 1 gram of silica gel was added. The mixture was concentrated in vacuo to dryness and applied to the top of column of silica gel and eluted with a 15-50% ethyl acetate/dichloromethane gradient. The proper fractions were combined and concentrated in vacuo to give 0.28 g (70%) of 4-chloro-N-{3-[(methylsulfonyl)methyl]phenyl}-1,3,5-triazin-2-amine as a white solid. HNMR: δ 10.83 (s, 1H), 8.64 (s, 1H), 7.63 (m, 2H), 7.4 (t, 1H), 7.25 (d, 1H), 4.48 (s, 2H), 2.94 (s, 3H); MS (ES+, m/z) 299, 301 (M+H).

Intermediate Example 11

Preparation of 2,3-dimethyl-2H-indazol-6-amine

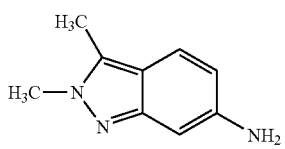

To a stirred solution of 18.5 g (0.11 mol) of 3-methyl-6-nitro-1H-indazole in 350 ml acetone, at room temperature, was added 20 g (0.14 mol) of trimethyloxonium tetraflouroborate. After the solution was allowed to stir under argon for 3 hours, the solvent was removed under reduced pressure. To the resulting solid was added saturated aqueous NaHCO$_3$ (600 ml) and a 4:1 mixture of chloroform-isopropanol (200 ml), and the mixture was agitated and the layers were separated. The aqueous phase was washed with additional chloroform: isopropanol (4×200 ml) and the combined organic phase was dried (Na$_2$SO$_4$). Filtration and removal of solvent gave a tan solid. The solid was washed with ether (200 ml) to afford 2,3-dimethyl-6-nitro-2H-indazole as a yellow solid (15.85 g, 73%). $^1$H NMR (300 MHz, d$_6$DMSO) δ 8.51 (s, 1H), 7.94 (d, J=9.1 Hz, 1H), 7.73 (d, J=8.9 Hz, 1H), 4.14 (s, 3H), 2.67 (s, 3H). MS (ES+, m/z) 192 (M+H).

To a stirred solution of 2,3-dimethyl-6-nitro-2H-indazole (1.13 g) in 2-methoxyethyl ether (12 ml), at 0° C., was added a solution of 4.48 g of tin(II)chloride in 8.9 ml of concentrated HCl dropwise over 5 min. After the addition was complete, the ice bath was removed and the solution was allowed to stir for an additional 30 min. Approximately 40 ml of diethyl ether was added to reaction, resulting in precipitate formation. The resulting precipitate was isolated by filtration and washed with diethyl ether, and afforded a yellow solid (1.1 g, 95%), the HCl salt 2,3-dimethyl-2H-indazol-6-amine. $^1$H NMR (300 MHz, d$_6$DMSO) δ 7.77 (d, J=8.9 Hz, 1H), 7.18 (s, 1H), 7.88 (m, 1H), 4.04 (s, 3H), 2.61 (s, 3H). MS (ES+, m/z) 162 (M+H).

Intermediate Example 12

Preparation of N-(2-chloropyrimidin-4-yl)-2,3-dimethyl-2H-indazol-6-amine

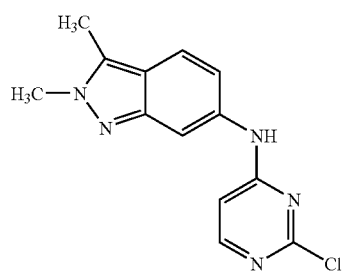

To a stirred solution of Intermediate Example 11 (2.97 g, 0.015 mol) and NaHCO$_3$ (5.05 g, 0.06 mol) in THF (15 mL) and ethanol (60 mL) was added 2,4-dichloropyrimidine (6.70 g, 0.045 mol) at room temperature. After the reaction was stirred for four hours at 85° C., the suspension was cooled to rt., filtered and washed thoroughly with ethyl acetate. The filtrate was concentrated under reduced pressure, and the resulting solid was triturated with ethyl acetate to yield 3.84 g (89% yield) of N-(2-chloropyrimidin-4-yl)-2,3-dimethyl-2H-indazol-6-amine. $^1$H NMR (400 MHz, d$_6$DMSO) δ 7.28 (d, J=9.0 Hz, 1H), 6.42 (d, J=8.8 Hz, 1H), 6.37 (s, 1H), 5.18 (br s, 1H), 3.84 (s, 3H), 2.43 (s, 3H). MS (ES+, m/z) 274 (M+H).

Intermediate Example 13

Preparation of N-(2-chloropyrimidin-4-yl)-N,2,3-trimethyl-2H-indazol-6-amine

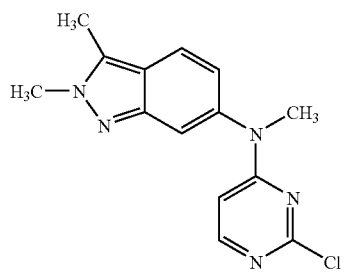

To a stirred solution of the Intermediate 12 (7.37 g) in DMF (50 ml) was added Cs$_2$CO$_3$ (7.44 g, 2 eqv.) and MeI (1.84 ml, 1.1 eqv.) at room temperature. Mixture was stirred at rt for overnight. The reaction mixture was poured into ice-water bath, and the precipitate was collected via filtration and washed with water. The precipitate was air-dried to afford N-(2-chloropyrimidin-4-yl)-N,2,3-trimethyl-2H-indazol-6-amine as an off-white solid (6.43 g, 83%). $^1$H NMR (400 MHz, d$_6$DMSO) δ 7.94 (d, J=6.0 Hz, 1H), 7.80 (d, J=1H), 7.50 (d, J=1.0 Hz, 1H), 6.88 (m, 1H), 6.24 (d, J=6.2 Hz, 1H), 4.06 (s, 3H), 3.42 (s, 3H), 2.62 (s, 3H). MS (ES+, m/z) 288 (M+H).

Intermediate Example 14

Preparation of 2-Chloro-5-({4-[(2,3-dimethyl-2H-indazol-6-yl)amino]-1,3,5-triazine

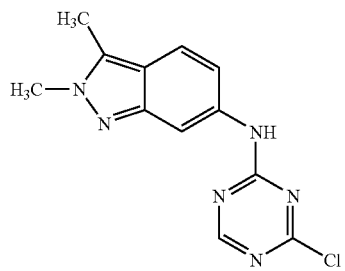

Intermediate Example 11 (free base) (0.080 g, 0.5 mmol), and 2,4-dichloro-1,3,5-triazine (Harris, R. L. N.; Amide-acid chloride adducts in organic synthesis. Part 12. The synthesis of triazines form N-cyanocarbamimidates. SYNTHESIS (1981), 11, 907-8) (0.075 g, 0.5 mmol), were combined in acetonitrile. DIEA was added and the solution was stirred at RT for 18 h. The resulting precipitate was filtered off and washed with acetonitrile to give analytically pure product as a light yellow solid (0.10 g, 0.36 mmol). $^1$H NMR (300 MHz, d$_6$DMSO) δ 10.73 (s, 1H), 8.63 (d, J=15.3 Hz, 1H), 7.94 (d, J=7.7 Hz, 1H), 7.62 (d, J=8.9 Hz, 1H), 7.13 (d, J=7.9 Hz, 1H), 4.01 (s, 3H), 2.57 (s, 3H). MS (ES+, m/z), 275 (M+H).

Intermediate Example 15

Preparation of 2-Chloro-5-({4-[(2,3-dimethyl-2H-indazol-6-yl)(methyl)amino]-1,3,5-triazine

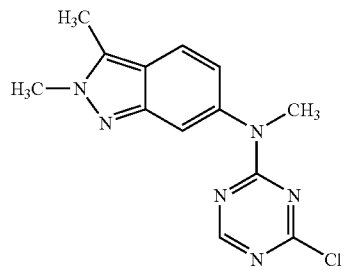

Intermediate Example 14 (0.05 g, 0.18 mmol) was combined with cesium carbonate (0.088 g, 0.27 mmol), and DMF (1 mL). Methyl iodide (0.033 mL, 0.54 mmol) was added and the solution was stirred at RT for 18 h. Water was added and the solution was washed with diethyl ether. The organic layer was dried with magnesium sulfate, filtered, and concentrated, to give a light yellow glass (0.035 g, 0.12 mmol) which was >90 pure by HPLC. This material was used directly in the next step. $^1$H NMR (300 MHz, d$_6$DMSO) δ 8.6 (br s, 1H), 7.70 (d, J=8.2 Hz, 1H), 7.48 (s, 1H), 6.90 (d, J=8.0 Hz, 1H), 4.04 (s, 3H), 3.48 (s, 3H), 2.60 (s, 3H). MS (ES+, m/z) 289 (M+H).

Intermediate Example 16

Preparation of N$^1$-methyl-4-nitrobenzene-1,2-diamine

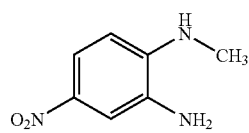

In a 350 mL pressure flask, 2-fluoro-5-nitroaniline (10 g, 0.064 mol), methylamine as a 2M solution in THF (65 mL, 0.13 mol) and potassium carbonate (18 g, 0.13 mol) in 1-Methyl-2-pyrrolidinone (80 mL) were combined. The flask was sealed and heated to 120 degrees C. overnight. The reaction was monitored by TLC. When reaction was judged to be complete based upon consumption of 2-fluoro-5-nitroaniline, it was cooled to room temperature and poured into 2-3 times the total reaction volume of water. When a precipitate was formed, it was filtered and dried. The product was carried on without purification. 1H NMR (300 MHz, d$_6$DMSO) δ 7.54 (dd, J=8.79, 2.64 Hz, 1H), 7.39 (d, J=2.64 Hz, 1H), 6.41 (d, J=8.79 Hz, 1H), 6.11 (d, J=4.39 Hz, 1H), 5.07 (s, 2H), 2.83 (d, J=4.83 Hz, 3H).

Intermediate Example 17

Preparation of 1,2-dimethyl-5-nitro-1H-benzimidazole

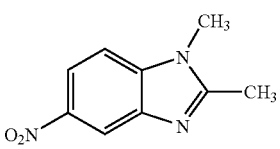

Intermediate Example 16 (7 g, 0.042 mol) and trimethoxy orthoacetate (5.86 mL, 0.046 mol) were combined in 4N HCl (70 mL). The reaction was heated to reflux and followed by TLC. When reaction was judged to be complete based upon consumption of diamine, it was slowly poured into 6N NaOH (65 mL) and ice and allowed to stir until the pH was greater than 7.0. The product was extracted with EtOAc, dried over sodium sulfate, filtered and concentrated. The resulting material was carried on without purification. 1H NMR (300 MHz, d$_6$DMSO) δ 8.39 (d, J=2.20 Hz, 1H), 8.12 (dd, J=8.94, 2.20 Hz, 1H), 7.71 (d, J=8.94 Hz, 1H), 2.58 (s, 3H), 3.80 (s, 3H).

Intermediate Example 18

Preparation of Preparation of 2-benzyl-1-methyl-5-nitro-1H-benzimidazole

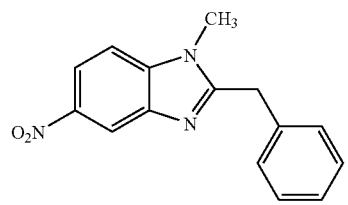

Intermediate Example 16 (2.3 g, 0.014 mol) and phenylacetic acid (2.8 g, 0.021 mol) were combined in 4N HCl (30 mL). The reaction was heated to reflux and followed by TLC. When reaction was judged to be complete based upon consumption of diamine, it was slowly poured into 6N NaOH (27 mL) and ice and allowed to stir until the pH was greater than 7.0. The product was extracted with EtOAc, dried over sodium sulfate, filtered and concentrated. The resulting material was generally carried on without purification. 1H NMR (300 MHz, d$_6$DMSO) δ8.46 (d, J=2.20 Hz, 1H), 8.14 (dd, J=8.94, 2.20 Hz, 1H,) 7.72 (d, J=8.94 Hz, 1H) 7.30 (m, 5H), 4.37 (s, 2H), 3.79 (s, 3H).

Intermediate Example 19

Preparation of 1,2-dimethyl-1H-benzimidazol-5-amine

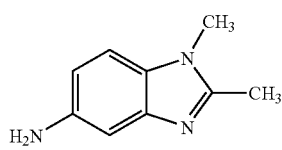

Intermediate Example 17 (7 g, 0.037 mol) and 10% Pd/C (0.7 g) in a concentrated methanol solution were shaken under approximately 40 psi of $H_2$ in appropriate pressure vessel using a Parr Hydrogenator. When the reaction was judged to be complete based upon the consumption of the nitrobenzimidazole, it was diluted with EtOAc and filtered through Celite and silica gel, which was washed with a mixture of EtOAc and MeOH and concentrated. The product was carried on without purification. 1H NMR (300 MHz, $d_6$DMSO) δ 7.11 (d, J=8.38 Hz, 1H), 6.69 (d, J=1.51 Hz, 1H), 6.53 (dd, J=8.38, 1.51 Hz, 1H), 4.65 (s, 2H), 3.62 (s, 3H), 2.43 (s, 3H).

Intermediate Example 20

Preparation of N-(2-chloropyrimidin-4-yl)-1,2-dimethyl-1H-benzimidazol-5-amine

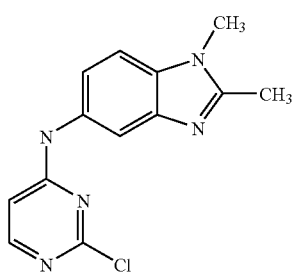

Intermediate Example 19 (4.5 g, 0.028 mol) and sodium bicarbonate (4.69 g, 0.056 mol) were combined in a 2:1 mixture of EtOH:THF (180 mL). 2,4-dichloropyrimidine (8.32 g, 0.056 mol) was added and the reaction was heat to 80 degrees C. The reaction was monitored by TLC. When reaction was judged to be complete based upon the consumption of aminobenzimidazole, the reaction was filtered while hot and the filtrate was concentrated. The resulting solid was washed with ether and EtOAc to remove excess 2,4-dichloropyrimidine and the resulting solid was carried on without purification. 1H NMR (300 MHz, $d_6$DMSO) δ 9.97 (s, 1H) 8.11 (d, J=5.91 Hz, 1H) 7.80 (s, 1H) 7.48 (d, J=8.52 Hz, 1H) 7.27 (d, J=7.83 Hz, 1H) 6.68 (d, J=5.91 Hz, 1H) 3.74 (s, 3H) 2.54 (s, 3H).

Intermediate Example 21

Preparation of N-(2-chloropyrimidin-4-yl)-N,1,2-trimethyl-1H-benzimidazol-5-amine

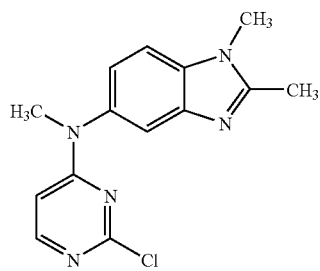

Intermediate Example 20 (6.5 g, 0.024 mol) was dissolved in DMF (70 mL). Sodium hydride (1.06 g of 60% dispersion in mineral oil, 0.026 mol) was slowly added in portions and the reaction was allowed to stir for 20 minutes under nitrogen. Methyl iodide (1.65 mL, 0.026 mol) was added and the reaction stirred for an additional 30 minutes. The reaction was monitored by TLC. When the reaction was judged to be complete based upon consumption of the anilinopyrimidine, water was slowly added to quench excess sodium hydride and product was extracted with EtOAc. The combined organic layers were washed with water to remove DMF, dried over sodium sulfate, filtered and concentrated. The reaction was chromatographed on silica gel using $CH_2Cl_2$ and MeOH as eluent to purify. 1H NMR (300 MHz, $d_6$DMSO) δ 7.89 (d, J=6.15 Hz, 1H) 7.59 (d, J=8.50 Hz, 1H) 7.50 (d, J=1.76 Hz, 1H) 7.13 (dd, J=8.50, 1.90 Hz, 1H) 6.10 (d, J=5.27 Hz, 1H) 3.75 (s, 3H) 3.41 (s, 3H) 2.53 (s, 3H).

Example 1 recites the general procedure for the synthesis of compounds of formula (I) and (II) wherein W=C—F:

Example 1

$N^2$-[5-(ethylsulfonyl)-2-methoxyphenyl]-5-fluoro-$N^4$-methyl-$N^4$-(3-methyl-1H-indazol-6-yl)-2,4-pyrimidinediamine

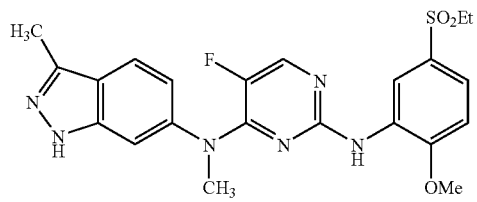

To a stirred suspension of the product of Intermediate Example 8 (2.0 g, 5.1 mmol) and 3-amino-4-methoxyphenyl ethyl sulfone (1.2 g, 5.6 mmol), in 10 mL of isopropanol, was added a drop of concentrated HCl at 80° C. After being stirred for 15 hr, the suspension was concentrated under reduced pressure. The resulting residue was diluted with 5 mL $CH_2Cl_2$ and 5 mL trifluoroacetic acid and stirred for 30 min at room temperature, then was diluted with $CH_2Cl_2$ (3×40 mL), and washed with saturated $NaHCO_3$. The extracts were dried over sodium sulfate, filtered, and concentrated under reduced pressure. The crude product was purified by silica gel column chromatography (4:1, $CH_2Cl_2$:EtOAc), giving 1.0 g (42%) of $N^2$-[5-(ethylsulfonyl)-2-methoxyphenyl]-5-fluoro-$N^4$-methyl-$N^4$-(3-methyl-1H-indazol-6-yl)-2,4-pyrimidinediamine as a white solid. HNMR (400 MHz, $d_6$-DMSO): δ 12.60 (bs, 1H), 8.91 (bs, 1H), 7.96 (d, 1H, J=5.5), 7.92 (s, 1H), 7.64 (d, 1H, J=8.6), 7.42 (d, 1H, J=8.4), 7.31 (s, 1H), 7.22 (d, 1H, J=8.6), 6.99 (d, 1H, J=8.4), 3.94 (s, 3H), 3.48 (s, 3H), 3.14 (q, 2H, J=7.3), 2.44 (s, 3H), 1.04 (t, 3H, J=7.4).

The compounds of Examples 2-15 were prepared according to the general procedure set forth in Example 1.

Example 2

3-({5-fluoro-4-[methyl(3-methyl-1H-indazol-6-yl)amino]-2-pyrimidinyl}amino)-4-methoxy-N-methyl-benzenesulfonamide

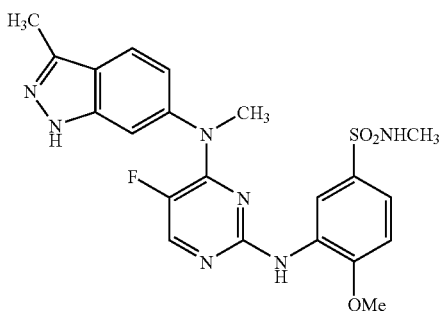

HNMR (400 MHz, $d_6$-DMSO): δ 12.60 (s, 1H), 8.89 (s, 1H), 7.95 (d, 1H), 7.91 (s, 1H), 7.64 (d, 1H), 7.31 (3H, m), 7.00 (d, 1H), 4.04 (m, 1H), 3.94 (s, 3H), 3.48 (s, 3H), 3.11 (s, 3H), 1.10 (d, 6H); MS (ES+, m/z)=442 (M+H).

Example 3

5-fluoro-$N^4$-methyl-$N^4$-(3-methyl-1H-indazol-6-yl)-$N^2$-{3-[(methylsulfonyl)methyl]phenyl}-2,4-pyrimidinediamine

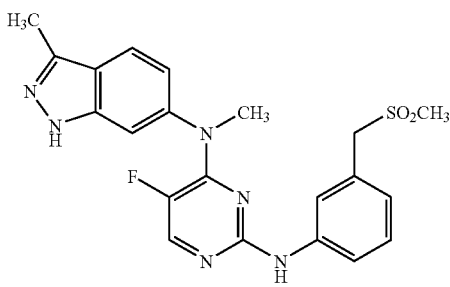

HNMR (400 MHz, $d_6$-DMSO): δ 12.65 (br s, 1H), 10.05 (s, 1H), 8.06 (d, 1H), 7.70 (d, 1H), 7.64 (s, 1H), 7.54 (d, 1H), 7.40 (m, 1H), 7.22 (m, 1H), 7.02 (m, 2H), 4.52 (s, 2H), 4.36 (s, 3H), 3.43 (s, 3H), 2.87 (s, 3H); MS (ES+, m/z)=441 (M+H).

Example 4

3-({5-fluoro-4-[methyl(3-methyl-1H-indazol-6-yl)amino]-2-pyrimidinyl}amino)-N-isopropyl-4-methoxybenzenesulfonamide

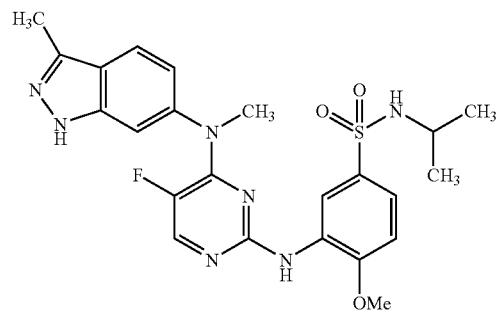

HNMR (400 MHz, $d_6$-DMSO): δ 12.59 (s, 1H), 8.83 (s, 1H), 7.93 (d, 1H), 7.85 (s, 1H), 7.65 (d, 1H), 7.43 (s, 1H), 7.36 (d, 1H), 7.30 (s, 1H), 7.28 (d, 1H), 7.16 (d, 1H), 6.99 (d, 1H), 3.91 (s, 3H), 3.47 (s, 3H), 3.16 (m, 1H), 0.89 (d, 6H); MS (ES+, m/z)=470 (M+H).

Example 5

5-fluoro-$N^2$-[5-(isopropylsulfonyl)-2-methoxyphenyl]-$N^4$-methyl-$N^4$-(3-methyl-1H-indazol-6-yl)-2,4-pyrimidinediamine

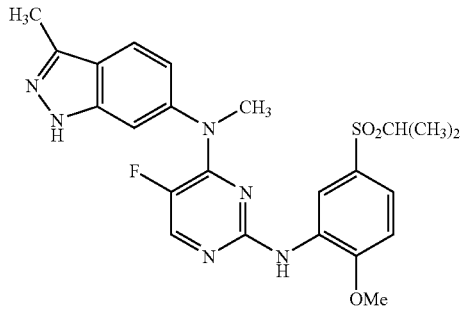

HNMR (400 MHz, $d_6$-DMSO): δ 12.60 (s, 1H), 8.89 (s, 1H), 7.98 (d, 1H), 7.91 (s, 1H), 3.11 (s, 3H), (d, 1H), 7.31 (m, 3H), 7.00 (d, 1H), 4.04 (m, 1H), 3.94 (s, 3H), 3.48 (s, 1H), 3.11 (s, 3H), 1.10 (d, 6H); MS (ES+, m/z)=485 (M+H).

Example 6

N-[5-({5-fluoro-4-[methyl(3-methyl-1H-indazol-6-yl)amino]-2-pyrimidinyl}amino)-2-methylphenyl]methanesulfonamide

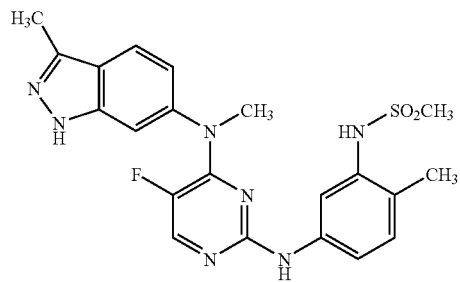

HNMR (400 MHz, d$_6$-DMSO): δ 12.66 (br s, 1H), 9.56 (s, 1H), 8.98 (s, 1H), 7.95 (d, 1H), 7.66 (d, 1H), 7.57 (s, 1H), 7.41 (d, 1H), 7.33 (s, 1H), 7.03 (d, 1H), 7.00 (d, 1H), 3.48 (s, 3H), 2.93 (s, 3H), 2.44 (s, 3H), 2.18 (s, 3H); MS (ES+, m/z)=456 (M+H).

Example 7

5-fluoro-N$^4$-methyl-N$^4$-(3-methyl-1H-indazol-6-yl)-N$^2$-[4-(methylsulfonyl)phenyl]-2,4-pyrimidinediamine

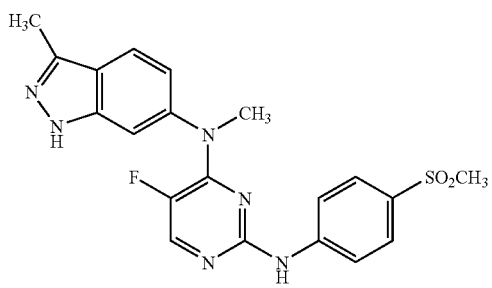

HNMR (400 MHz, d$_6$-DMSO): δ 12.68 (s, 1H), 9.80 (s, 1H), 8.01 (d, 1H), 7.76 (d, 1H), 7.66 (d, 1H), 7.58 (d, 1H), 7.36 (s, 1H), 7.01 (d, 1H), 3.48 (s, 3H), 3.05 (s, 3H); MS (ES+, m/z)=427 (M+H).

Example 8

N$^4$-(3-ethyl-1H-indazol-6-yl)-5-fluoro-N$^4$-methyl-N$^2$-{3-[(methylsulfonyl)methyl]phenyl}-2,4-pyrimidinediamine

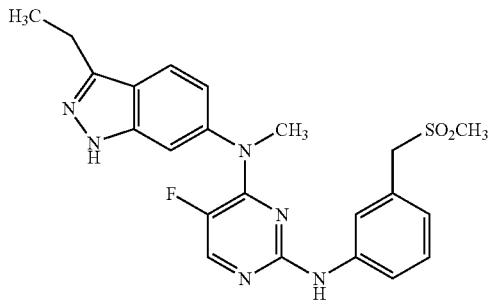

HNMR (400 MHz, d$_6$-DMSO): δ 12.57 (br s, 1H), 9.35 (s, 1H), 7.92 (d, 1H, J=5.7), 7.75 (br s, 1H), 7.67 (d, 1H, J=8.6), 7.60 (d, 1H, J=8.5), 7.28 (s, 1H), 7.14 (dd, 1H, J=7.89, 7.9), 6.97 (d, 1H, J=8.4), 6.87 (d, 1H, J=7.5), 4.31 (s, 2H), 3.47 (s, 3H), 2.88 (m, 2H), 2.85 (s, 3H), 1.26 (t, 3H, J=7.6); MS (AP+, m/z)=455 (M+H).

Example 9

4-({5-fluoro-4-[methyl(3-methyl-1H-indazol-6-yl)amino]-2-pyrimidinyl}amino)benzenesulfonamide

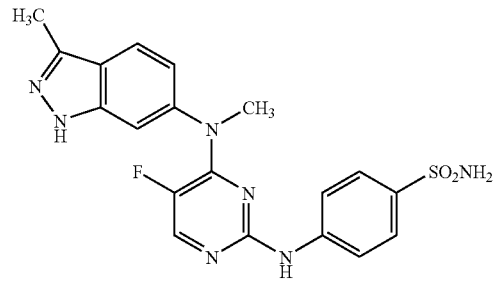

HNMR (400 MHz, d$_6$-DMSO): δ 12.65 (br s, 1H), 9.81 (s, 1H), 8.01 (d, 1H), 7.75 (d, 1H), 7.67 (d, 1H), 7.59 (d, 2H), 7.33 (s, 1H), 7.10 (br s, 1H), 7.00 (d, 1H), 3.80 (s, 1H), 3.49 (s, 3H), 2.40 (s, 3H); MS (ES+, m/z)=428 (M+H).

Example 10

N$^4$-ethyl-5-fluoro-N$^2$-[2-methoxy-5-(methylsulfonyl)phenyl]-N$^4$-(3-methyl-1H-indazol-6-yl)-2,4-pyrimidinediamine

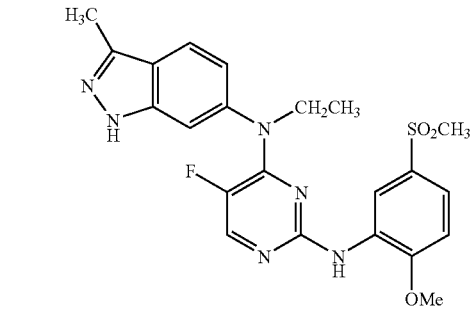

HNMR (400 MHz, d$_6$-DMSO): δ12.57 (s, 1H), 9.32 (s, 1H), 7.89 (s, 1H), 7.72 (s, 1H), 7.64 (d, 1H), 7.59 (d, 1H), 7.25 (s, 1H), 6.95 (d, 1H), 6.87 (d, 1H), 4.29 (s, 3H), 3.98 (q, 2H), 2.86 (s, 3H), 2.43 (s, 3H), 1.15 (t, 3H); MS (ES+, m/z)=471 (M+H).

Example 11

[4-({5-fluoro-4-[methyl(3-methyl-1H-indazol-6-yl)amino]-2-pyrimidinyl}amino)phenyl]-N-methyl-methanesulfonamide

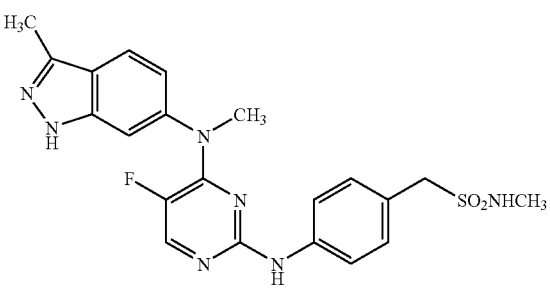

HNMR (400 MHz, d$_6$-DMSO): δ 12.57 (s, 1H), 9.35 (s, 1H), 7.92 (d, 1H), 7.66 (d, 1H), 7.64 (s, 1H), 7.63 (d, 1H), 7.28 (s, 1H), 7.16 (d, 1H), 7.13 (d, 1H), 6.87 (d, 1H), 4.29 (s, 2H), 3.47 (s, 3H), 4.14 (s, 1H), 2.80 (s, 3H), 2.48 (s, 3H); MS (ES+, m/z)=456 (M+H).

Example 12

5-fluoro-N$^2$-{3-[(isopropylsulfonyl)methyl]phenyl}-N$^4$-methyl-N$^4$-(3-methyl-1H-indazol-6-yl)-2,4-pyrimidinediamine

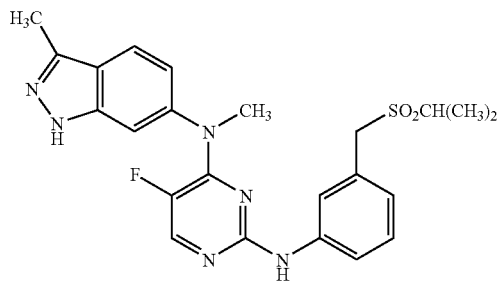

HNMR (400 MHz, d$_6$-DMSO): δ 12.70 (br s, 1H), 9.73 (s, 1H), 7.99 (d, 1H), 7.72 (s, 1H), 7.67 (d, 1H), 7.56 (d, 1H), 7.35 (s, 1H), 7.18 (dd, 1H), 7.01 (d, 1H), 6.95 (d, 1H), 4.32 (s, 2H), 3.50 (s, 3H), 3.13 (m, 1H), 2.43 (s, 3H), 1.21 (d, 6H); MS (ES+, m/z)=469 (M+H).

Example 13

3-({5-fluoro-4-[methyl(3-methyl-1H-indazol-6-yl)amino]-2-pyrimidinyl}amino)-4-methoxybenzamide

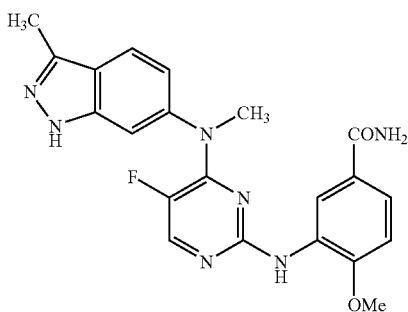

HNMR (400 MHz, d$_6$-DMSO): δ 12.62 (s, 1H), 8.80 (d, 1H), 7.95 (d, 1H), 7.79 (s, 1H), 7.78 (brs, 1H), 7.68 (d, 1H), 7.53 (dd, 1H), 7.32 (s, 1H), 7.11 (brs, 1H), 7.05 (d, 1H), 7.02 (d, 1H), 3.92 (s, 3H), 3.49 (s, 3H), 2.47 (s, 3H); MS (ES+, m/z)=422 (M+H).

Example 14

4-({5-fluoro-4-[methyl(3-methyl-1H-indazol-6-yl)amino]-2-pyrimidinyl}amino)-3-methoxybenzenesulfonamide

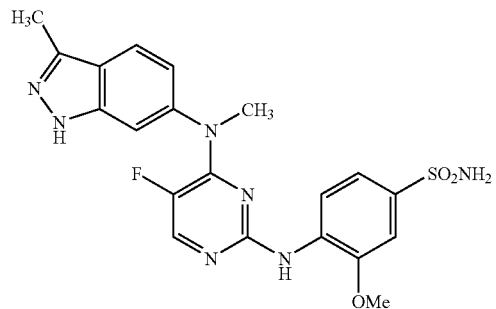

HNMR (400 MHz, d$_6$-DMSO): δ 12.30 (br s, 1H), 8.77 (s, 1H), 8.10 (d, 1H), 7.73 (d, 1H), 7.54 (d, 1H), 7.44 (s, 1H), 7.24 (d, 1H), 7.22 (s, 1H), 7.20 (brs, 2H), 7.08 (d, 1H), 3.96 (s, 3H), 3.55 (s, 3H), 2.47 (s, 3H); MS (ES+, m/z)=457 (M+H).

Examples 15 and 16 recite the general procedure for the synthesis of compounds of formula (I) and (II) wherein W=N:

Example 15

N$^2$-(3-methyl-1H-indazol-6-yl)-N$^4$-{3-[(methylsulfonyl)methyl]phenyl}-1,3,5-triazine-2,4-diamine trifluoroacetate

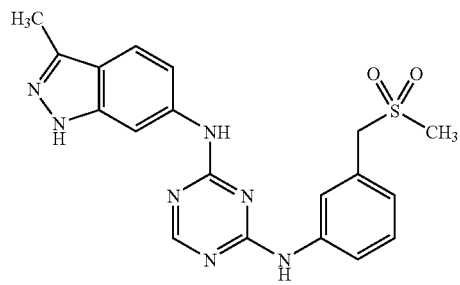

To a flask containing a magnetic stir bar was added 0.03 g (0.20 mmol) of 3-methyl-1H-indazol-6-amine and 0.060 g (0.20 mmol) of 4-chloro-N-{3-[(methylsulfonyl)methyl]phenyl}-1,3,5-triazin-2-amine and 2 mL of isopropanol and the resultant mixture was heated at reflux for ca. 16 hours. Upon cooling the reaction mixture a solid precipitated. The solid was filtered and washed with ethyl acetate (2×4 mL), acetonitrile (4 mL), and ethyl ether (4 mL) and dried under vacuum to give N$^2$-(3-methyl-1H-indazol-6-yl)-N$^4$-{3-[(methylsulfonyl)methyl]phenyl}-1,3,5-triazine-2,4-diamine hydrochloride as a solid. The solid was purified by C-18 RP-HPLC using an acetonitrile/water gradient containing 0.5% trifluoroacetic acid buffer. Concentrating the proper fractions gave 0.015 g (10%) of N$^2$-(3-methyl-1H-indazol-6-yl)-N$^4$-{3-[(methylsulfonyl)methyl]phenyl}-1,3,5-triazine-2,4-diamine trifluoroacetate as a white solid. HNMR: δ12.4 (br s, 1H), 9.9 (br s, 1H), 8.34 (s, 1H), 7.8 (br s, 1H), 7.67 (br s, 1H), 7.56 (d, 1H), 7.29 (m, 2H), 7.02 (br s, 2H), 2.83 (br s, 3H), 2.40 (s, 3H). MS (ES+, m/z)=409 (M+H).

Example 16

N²-methyl-N²-(3-methyl-1H-indazol-6-yl)-N⁴-{3-[(methylsulfonyl)methyl]phenyl}-1,3,5-triazine-2,4-diamine hydrochloride

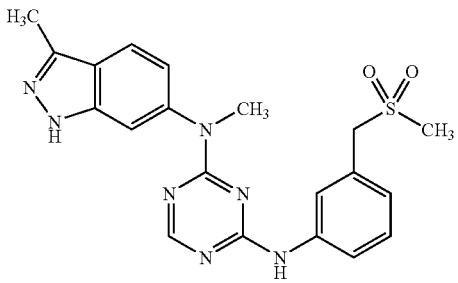

To a flask containing a magnetic stir bar was added 0.027 g (0.17 mmol) of N,3-dimethyl-1H-indazol-6-amine and 0.058 g (0.19 mmol) of 4-chloro-N-{3-[(methylsulfonyl)methyl]phenyl}-1,3,5-triazin-2-amine and 2 mL of isopropanol and the resultant mixture heated at reflux for ca. 16 hours. Upon cooling the reaction mixture a solid precipitated. The solid was filtered and washed with ethyl acetate (2×4 mL), acetonitrile (4 mL), and ethyl ether (4 mL) and dried under vacuum to give 0.03 g (42%) of N²-methyl-N²-(3-methyl-1H-indazol-6-yl)-N⁴-{3-[(methylsulfonyl)methyl]phenyl}-1,3,5-triazine-2,4-diamine hydrochloride as a light pink solid. Some of the peaks in the NMR spectrum are broad at room temperature. Heating to 90° C. produces peaks that are well resolved. HNMR: δ 12.5 (br s, 1H), 9.9 (br s, 1H), 8.24 (m, 1H) 7.72 (d, 1H) 7.5 (m), 7.38 (s, 1H), 7.01 (d, 1H) 6.9 (br s, 1H) 3.47 (s, 3H), 2.75 (br s, 3H), 2.47 (S, 3H). HNMR (at 90° C.): δ 9.62 (s, 1H), 8.29 (s, 1H), 7.76 (d, 1H), 7.66 (s, 1H), 7.54 (d, 1H), 7.43 (s, 1H) 7.1 (m, 3H), 4.13 (s, 2H), 3.56 (s, 3H), 2.93 (s, 3H), 2.55 (s, 3H); MS (ES+, m/z)=424 (M+H).

In most cases the hydrochloride salts are obtained in sufficient purity. When this is not the case, the amine hydrochloride salts are purified either by Reverse Phase High Pressure Liquid Chromatography (RPHPLC), or by normal phase chromatography by loading the solids on 1 gram of silica gel. The silica gel mixture is then loaded on top of a column of silica gel and eluted with a chloroform/ethyl acetate to methanol/ethyl acetate gradient. As stated above, some of the peaks in the NMR spectrum are broad at room temperature. Heating to 90° C. produces peaks that are well resolved.

The compounds of Examples 17-20 were prepared according to the general procedures set forth above in Examples 15 and 16.

Example 17

N²-[5-(ethylsulfonyl)-2-methoxyphenyl]-N⁴-methyl-N⁴-(3-methyl-1H-indazol-6-yl)-1,3,5-triazine-2,4-diamine hydrochloride

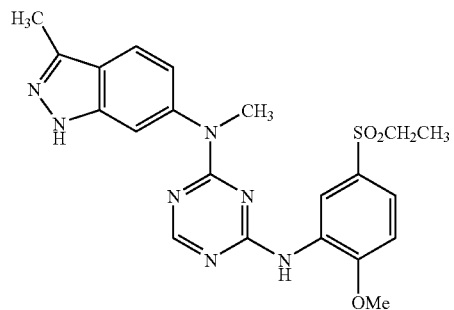

HNMR (d₆DMSO, 300 MHz): δ 8.89 (br s, 1H), 8.56 (br s, 1H), 8.26 (s, 1H), 7.72 (d, 1H), 7.62 (d, 1H), 7.41 (s, 1H), 7.31 (d, 1H), 7.04 (d, 1H), 3.95 (s, 3H), 3.50 (s, 3H), 3.13 (br s, 2H), 1.08 (t, 3H). At 90 degrees, peaks sharpen and peak at 3.13 resonates as a quartet. MS (AP+, m/z)=454 (M+1).

Example 18

N-[2-methyl-5-({4-[methyl(3-methyl-1H-indazol-6-yl)amino]-1,3,5-triazin-2-yl}amino)phenyl]methanesulfonamide

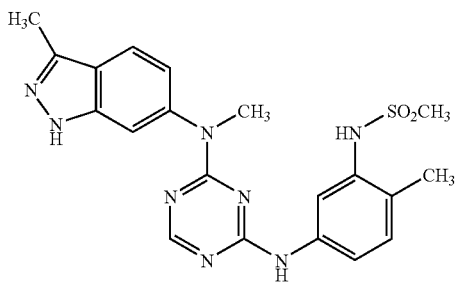

HNMR (d₆DMSO, 300 MHz): δ 12.60 (br s, 1H), 9.6 (br s, 1H), 8.92 (br s, 1H), 8.15 (br s, 1H) 7.67 (d, 1H), 7.52 (br s, 1H), 7.39 (br s, 1H), 7.34 (s, 1H), 6.99 (d, 1H), 3.46 (s, 3H), 2.89 (s, 3H), 2.14 (s, 3H). HNMR (d₆DMSO @ 90° C., 300 MHz): δ 12.46 (br s, 1H), 9.39 (s, 1H), 8.73 (s, 1H), 8.23 (s, 1H), 7.73 (d, 1H), 7.59 (s, 1H), 7.47 (d, 1H), 7.40 (s, 1H), 7.06 (d, 1H), 6.93 (d, 1H), 3.55 (s, 3H), 2.99, (s, 3H), 2.24 (s, 3H). MS (AP+, m/z)=439 (M+1).

Example 19

N²-methyl-N²-(3-methyl-1H-indazol-6-yl)-N⁴-[3-(methylsulfonyl)phenyl]-1,3,5-triazine-2,4-diamine

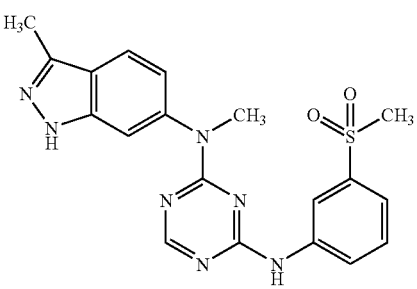

HNMR (d₆DMSO @ 90° C., 300 MHz): δ 12.48 (br s, 1H), 9.82 (s, 1H), 8.36 (s, 1H), 8.30 (s, 1H), 7.91 (d, 1H), 7.75 (d, 1H), 7.50 (d, 1H), 7.43 (s, 1H), 7.33 (t, 1H), 3.57 (s, 3H), 2.54 (s, 3H). Note: at room temperature, the SO2CH3 group resonates at 3.05 as a broad singlet, whereas at 90° C., the SO2CH3 group resonates under the H2O peak. MS (ES+, m/z)=410 (M+1).

Example 20

N-[4-({4-[methyl(3-methyl-1H-indazol-6-yl)amino]-1,3,5-triazin-2-yl}amino)phenyl]acetamide hydrochloride

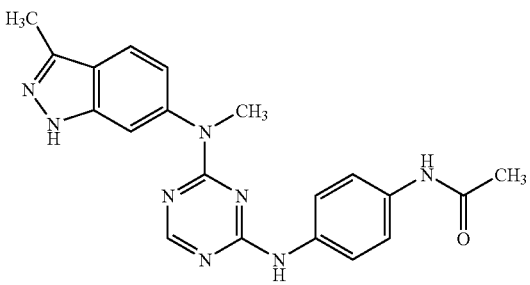

HNMR (d₆DMSO @ 90° C., 300 MHz): δ 9.58 (s, 1H), 9.54 (s, 1H), 8.27 (s, 1H), 7.75 (d, 1H), 7.50 (s, 1H), 7.45 (d, 2H), 7.33 (d, 2H), 7.08 (d, 1H), 3.56 (s, 3H), 2.56 (s, 3H), 2.03 (s, 3H), MS (ES+, m/z)=389 (m+1).

Example 21 recites the general procedure for the synthesis of compounds of formula (I) and (II) wherein W=C—H:

Example 21

3-({4-[methyl(3-methyl-1H-indazol-6-yl)amino]-2-pyrimidinyl}amino)benzenesulfonamide hydrochloride

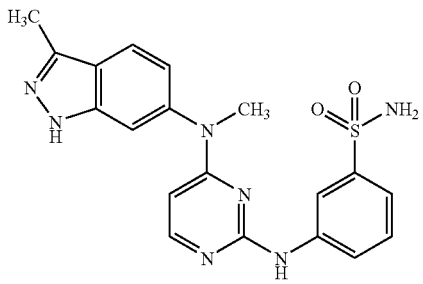

To a solution of Intermediate Example 9 (200 mg, 0.535 mmol) and 3-aminobenzenesulfonamide (92.1 mg, 0.535 mmol) in isopropanol (6 ml) was added 4 drops of conc. HCl. The mixture was heated to reflux overnight. The mixture was cooled to rt and diluted with ether (6 ml). Precipitate was collected via filtration and washed with ether. 3-({4-[methyl(3-methyl-1H-indazol-6-yl)amino]-2-pyrimidinyl}amino)-benzenesulfonamide was isolated as off-white solid (214 mg).

¹H NMR (300 MHz, d₆DMSO) δ 12.73 (br s, 1H), 9.54 (s, 1H), 8.55 (s, 1H), 7.86 (d, J=6.0 Hz, 1H), 7.78-7.81 (m, 2H), 7.40 (s, 1H), 7.33-7.34 (m, 2H), 7.25 (br s, 2H), 7.02 (d, J=8.4 Hz, 1H), 5.82 (d, J=6.0 Hz, 1H), 3.51 (s, 3H), 2.50 (s, 3H). MS (ES+, m/z) 410 (M+H).

Unless otherwise indicated, the compounds of Examples 22-37 and 41-68 were prepared according to the general procedures set forth above in Example 21. In most cases the hydrochloride salts of these examples were readily obtained as described in the experimental above. In certain cases it was more convenient to isolate the final compound as its free base by partitioning with an organic solvent (e.g., ethyl acetate) and an aqueous base (e.g. aqueous sodium bicarbonate). It will be readily apparent to those skilled in the art that the syntheses of these examples will use either of Scheme 1 or Scheme 2 described above, depending on group $X_4$, the nature of which defines the alkylating agent whose use is described in Scheme 2. The NMR data characterizing these examples describe either the salt form or the free base form.

Example 22

$N^2$-[5-(ethylsulfonyl)-2-methoxyphenyl]-$N^4$-methyl-$N^4$-(3-methyl-1H-indazol-6-yl)-2,4-pyrimidinediamine

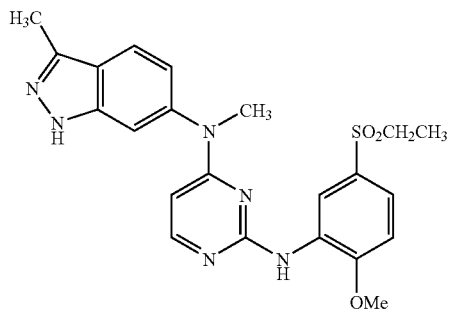

HNMR: δ 12.74 (s, 1H), 9.10 (s, 1H), 7.85 (d, J=6.0 Hz, 1H), 7.81 (s, 1H), 7.79 (d, J=8.2 Hz, 1H), 7.46 (d, J=8.6 Hz, 1H), 7.41 (s, 1H), 7.25 (d, J=8.2 Hz, 1H), 7.05 (d, J=8.6 Hz, 1H), 5.78 (d, J=6.0 Hz, 1H), 3.99 (s, 3H), 3.51 (s, 3H), 3.18 (q, J=7.4 Hz, 2H), 2.50 (s, 3H), 1.09 (t, J=7.4 Hz, 3H); MS (ES+, m/z)=451, 452 (M+H).

Example 23

$N^4$-methyl-$N^4$-(3-methyl-1H-indazol-6-yl)-$N^2$-{3-[(methylsulfonyl)methyl]phenyl}-2,4-pyrimidinediamine

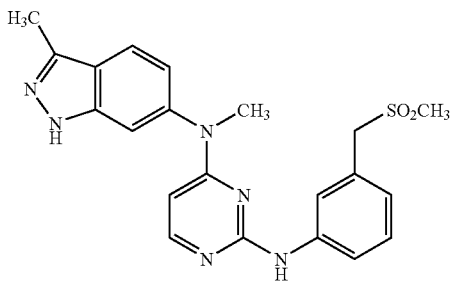

HNMR: δ 12.70 (s, 1H), 9.24 (s, 1H), 7.85 (d, J=6.1 Hz, 1H), 7.81 (s, 1H), 7.78 (d, J=8.5 Hz, 1H), 7.65 (d, J=8.1 Hz,

1H), 7.37 (s, 1H), 7.15 (t, J=7.9 Hz, 1H), 7.00 (d, J=8.5 Hz, 1H), 6.89 (d, J=7.5 Hz, 1H), 5.81 (d, J=6.1 Hz, 1H), 4.27 (s, 1H), 3.49 (s, 3H), 2.86 (s, 3H), 2.51 (s, 3H); MS (ES+, m/z)=423, 424 (M+H).

Example 24

N-isopropyl-3-({4-[methyl(3-methyl-1H-indazol-6-yl)amino]-2-pyrimidinyl}amino)benzenesulfonamide

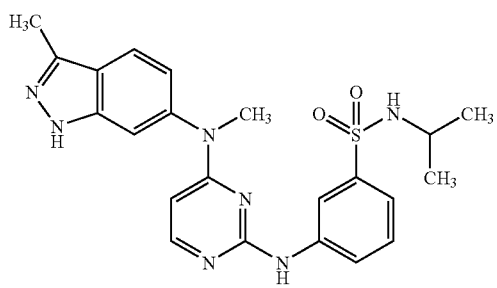

HNMR: δ 12.84 (s, 1H), 10.26 (s, 1H), 8.39 (s, 1H), 7.85 (d, J=6.5 Hz, 1H), 7.83 (d, J=5.0 Hz, 1H), 7.72 (s, 1H), 7.57 (d, J=7.4 Hz, 1H), 7.48 (s, 1H), 7.47 (s, 1H), 7.05 (d, J=8.4 Hz, 1H), 5.90 (d, J=6.5 Hz, 1H), (s, 1H), 3.54 (s, 3H), 3.25 (septet, J=6.8 Hz, 1H), 2.51 (s, 3H), 0.95 (d, J=6.8 Hz, 6H).

Example 25

N-cyclopropyl-3-({4-[methyl(3-methyl-1H-indazol-6-yl)amino]-2-pyrimidinyl}amino)benzenesulfonamide

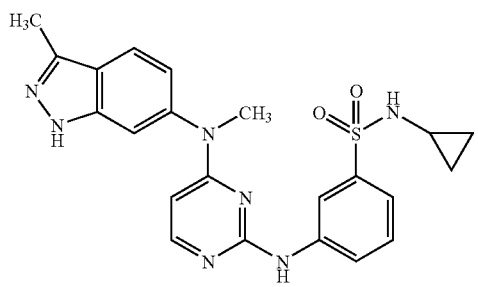

HNMR: δ 12.72 (s, 1H), 9.57 (s, 1H), 8.57 (s, 1H), 7.85 (d, J=6.1 Hz, 1H), 7.80 (s, 1H), 7.78 (d, J=5.2 Hz, 1H), 7.39 (s, 1H), 7.37 (t, J=8.1 Hz, 1H), 7.29 (d, J=7.7 Hz 1H), 7.00 (d, J=8.5 Hz, 1H), 5.79 (d, J=6.1 Hz, 1H), 3.51 (s, 3H), 2.51 (s, 3H), 2.18-2.10 (m, 1H), 0.51-0.30 (m, 4H).

Example 26

N$^4$-ethyl-N$^2$-[5-(ethylsulfonyl)-2-methoxyphenyl]-N$^4$-(3-methyl-1H-indazol-6-yl)-2,4-pyrimidinediamine

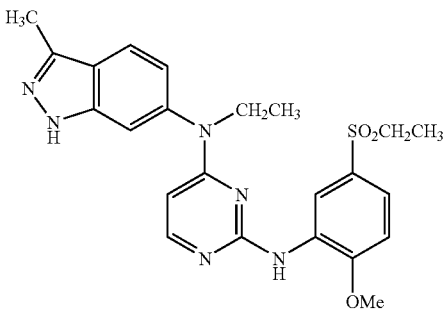

HNMR: δ 12.70 (s, 1H), 9.00 (s, 1H), 7.78 (s, 1H), 7.76 (d, 1H), 7.74 (d, 1H), 7.42 (d, 1H), 7.33 (s, 1H), 7.22 (d, 1H), 6.92 (d, 1H), 5.57 (d, 1H), 4.05 (q, 2H), 3.95 (s, 3H), 3.43 (s, 3H), 3.12 (q, 2H), 1.14 (t, 3H), 1.06 (t, 3H); MS (ES+, m/z)=485 (M+H).

Example 27

N-[3-({4-[methyl(3-methyl-1H-indazol-6-yl)amino]-2-pyrimidinyl}amino)phenyl]methanesulfonamide

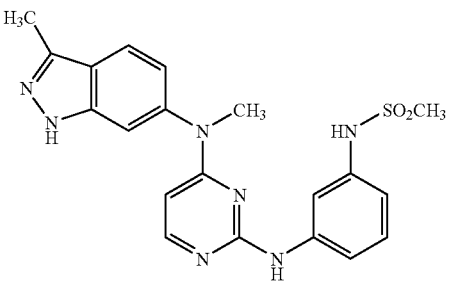

HNMR: δ 12.66 (s, 1H), 9.24 (s, 1H), 9.16 (s, 1H), 7.78 (d, J=5.9 Hz, 1H), 7.74 (d, J=8.3 Hz, 1H), 7.65 (s, 1H), 7.42 (d, J=8.3 Hz, 1H), 7.33 (s, 1H), 7.04 (t, J=8.0 Hz, 1H), 6.95 (d, J=8.3 Hz, 1H), 6.67 (d, J=7.9 Hz, 1H), 5.71 (d, J=5.9 Hz, 1H), 3.44 (s, 3H), 2.92 (s, 3H), 2.46 (s, 3H); MS (ES+, m/z)=424, 426 (M+H).

Example 28

N$^2$-{3-[(isopropylsulfonyl)methyl]phenyl}-N$^4$-methyl-N$^4$-(3-methyl-1H-indazol-6-yl)-2,4-pyrimidinediamine

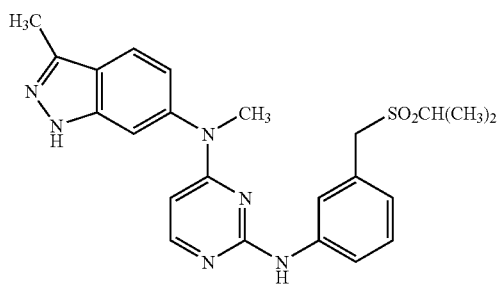

HNMR: δ 12.88 (s, 1H), 10.37 (s, 1H), 7.86 (d, J=6.5 Hz, 1H), 7.82 (d, J=8.6 Hz, 1H), 7.67 (s, 1H), 7.56 (d, J=7.9 Hz, 1H), 7.29 (s, 1H), 7.12 (d, J=7.3 Hz, 1H), 7.05 (d, J=8.6 Hz, 1H), 5.95 (d, J=6.5 Hz, 1H), 4.38 (s, 2H), 3.55 (s, 3H), 3.16 (septet, J=6.8 Hz, 1H), 2.51 (s, 3H), 1.26 (d, J=6.8 Hz, 6H); MS (ES+, m/z)=451, 452 (M+H).

Example 29

$N^2$-{4-[(isopropylsulfonyl)methyl]phenyl}-$N^4$-methyl-$N^4$-(3-methyl-1H-indazol-6-yl)-2,4-pyrimidinediamine

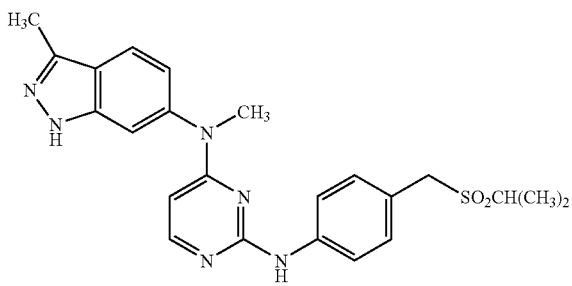

HNMR: δ 12.87 (s, 1H), 10.21 (s, 1H), 7.85 (d, J=6.2 Hz, 1H), 7.83 (d, J=8.5 Hz, 1H), 7.57 (d, J=8.1 Hz, 2H), 7.49 (s, 1H), 7.30 (d, J=8.5 Hz, 1H), 7.05 (d, J=8.1 Hz, 2H), 5.98 (d, J=6.2 Hz, 1H), 4.39 (s, 2H), 3.54 (s, 3H), 3.14 (septet, J=6.3 Hz, 1H), 2.51 (s, 3H), 1.26 (d, J=6.3 Hz, 6H), MS (ES+, m/z)=451, 452 (M+H).

Example 30

$N^2$-[5-(isobutylsulfonyl)-2-methoxyphenyl]-$N^4$-(3-methyl-1H-indazol-6-yl)-2,4-pyrimidinediamine

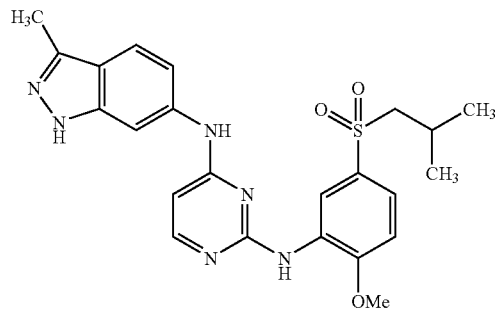

HNMR (400 MHz, $d_6$-DMSO) δ 12.29 (s, 1H), 9.57 (s, 1H), 8.75 (dd, 1H, J=2.14 Hz and J=6.42 Hz), 8.05 (d, 1H, J=5.89 Hz), 7.87 (br s, 1H), 7.77 (d, 1H, J=2.85 Hz), 7.54 (d, 1H, J=8.74 Hz), 7.47 (dd, 1H, J=2.14 Hz and J=8.56 Hz), 7.23 (d, 1H, J=8.65 Hz), 7.16 (d, 1H, J=8.56 Hz), 6.33 (d, 1H, J=5.71 Hz), 3.94 (s, 1H, 3H), 3.00 (d, 1H, J=6.42 Hz), 2.39 (s, 3H), 1.97-1.90 (m, 1H), 0.87 (d, 6H, J=6.78 Hz), MS (ES+, M/Z) 467 (M+H), (ES−, m/z) 465 (M−H).

Example 31

N-[3-({4-[methyl(3-methyl-1H-indazol-6-yl)amino]-2-pyrimidinyl}amino)phenyl]acetamide

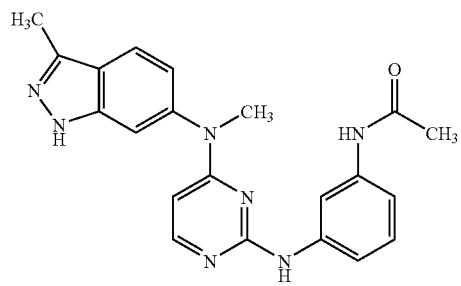

HNMR: δ 12.70 (s, 1H), 9.79 (s, 1H), 9.15 (s, 1H), 7.99 (s, 3H), 7.95 (s, 1H), 7.82 (d, 1H), 7.78 (d, 1H), 7.41 (s, 1H), 7.40 (s, 1H), 7.04 (dd, 1H), 7.01 (dd, 1H), 5.76 (d, 1H), 3.48 (s, 3H), 3.33 (s, 3H), 2.01 (s, 3H); MS (ES+, m/z)=388 (M+H).

Example 32

N-[3-({4-[ethyl(3-methyl-1H-indazol-6-yl)amino]-2-pyrimidinyl}amino)phenyl]acetamide

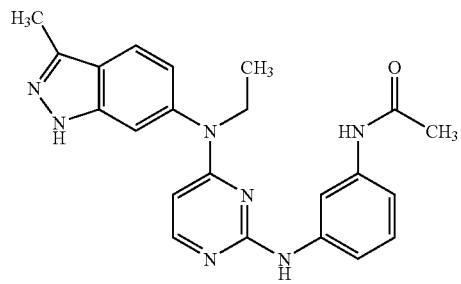

HNMR: δ 12.67 (s, 1H), 9.73 (s, 1H), 9.09 (s, 1H), 7.76 (s, 1H), 7.83 (d, 1H), 7.74 (d, 1H), 7.34 (s, 1H), 7.32 (d, 1H), 6.45 (dd, 1H), 6.41 (dd, 2H), 5.76 (d, 1H), 3.97 (q, 1H), 3.47 (s, 3H), 3.33 (s, 3H), 2.13 (s, 3H); MS (ES+, m/z)=402 (M+H).

Example 33

$N^2$-(2-methoxy-5-{[(5-methyl-3-isoxazolyl)methyl]sulfonyl}phenyl)-$N^4$-(3-methyl-1H-indazol-6-yl)-2,4-pyrimidinediamine

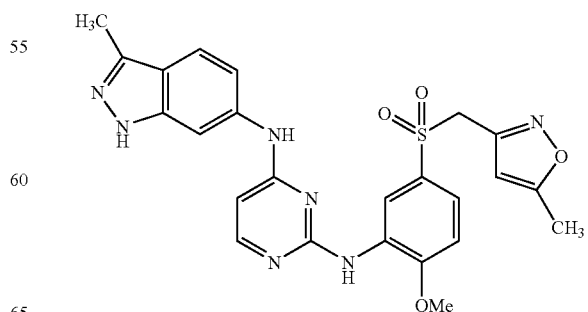

HNMR (400 MHz, d$_6$-DMSO) δ 12.34 (br s, 1H), 9.63 (br s, 1H), 8.77-8.75 (m, 1H), 8.08 (d, 1H, J=5.79 Hz), 7.90 (br s, 1H), 7.78 (brs, 1H), 7.41 (dd, 1H, J=2.12 Hz and J=8.61 Hz), 7.24 (d, 1H, J=8.75 Hz), 7.19 (br s, 1H), 6.38 (d, 1H, J=5.93 Hz), 6.14 (s, 1H), 4.64 (s, 2H), 3.98 (s, 3H), 2.42 (s, 3H), 2.34 (s, 3H), MS (ES+, m/z) 506 (M+H).

Example 34

4-methoxy-3-({4-[(3-methyl-1H-indazol-6-yl)amino]-2-pyrimidinyl}amino)benzenesulfonamide

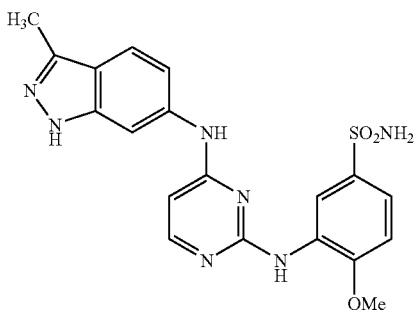

HNMR (400 MHz, d$_6$-DMSO) δ 12.28 (br s, 1H), 9.56 (br s, 1H), 8.72 (br s, 1H), 8.02 (d, 1H, J=5.71 Hz), 7.87 (br s, 1H), 7.74 (br s, 1H), 7.55 (d, 1H, J=8.74 Hz), 7.43 (d, 1H, J=8.03 Hz), 7.17-7.13 (m, 4H), 6.32 (d, 1H, J=5.89 Hz), 3.91 (s, 3H), 2.39 (s, 3H), MS (ES, m/z) 424 (M–H).

Example 35

N$^2$-[5-(isopropylsulfonyl)-2-methoxyphenyl]-N$^4$-methyl-N$^4$-(3-methyl-1H-indazol-6-yl)-2,4-pyrimidinediamine

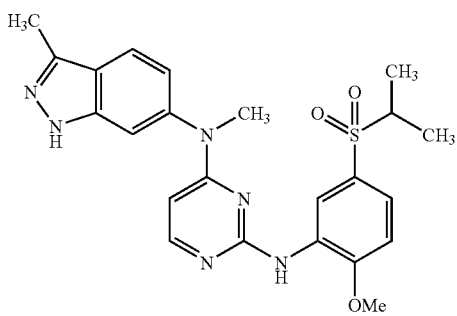

$^1$H NMR (400 MHz, d$_6$-DMSO) □ 12.71 (br s, 1H), 9.03 (s, 1H), 7.83-7.79 (m, 2H), 7.78 (d, J=8.4 Hz, 1H), 7.40-7.38 (m, 2H), 7.22 (d, J=8.6 Hz, 1H), 6.97 (d, J=8.4 Hz, 1). 5.74 (d, J=6.1 Hz, 1H), 3.95 (s, 3H), 3.47 (s, 3H), 3.24 (m, 1H), 2.45 (s, 3H), 1.11 (d, J=6.7 Hz, 6H). MS (ES+, m/z) 467 (M+H).

Example 36

N$^2$-[5-(ethylsulfonyl)-2-methoxyphenyl]-N$^4$-isopropyl-N$^4$-(3-methyl-1H-indazol-6-yl)-2,4-pyrimidinediamine

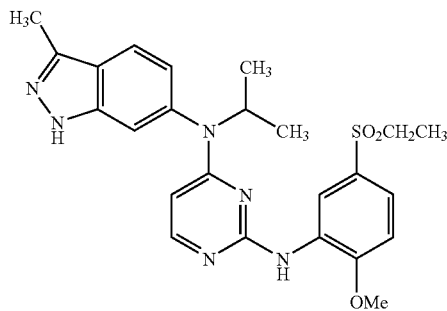

HNMR: δ 12.69 (s, 1H), 9.18 (s, 1H), 7.78 (s, 1H), 7.76 (d, 1H), 7.69 (d, 1H), 7.57 (d, 1H), 7.22 (s, 1H), 6.86 (d, 1H), 6.82 (d, 1H), 5.26 (d, 1H), 5.24 (m, 1H), 4.28 (q, 2H), 2.87 (s, 3H), 2.44 (s, 3H), 1.31 (t, 3H), 1.08 (d, 6H); MS (ES+, m/z)=481 (M+H).

Example 37

N$^4$-(1H-indazol-6-yl)-N$^4$-methyl-N$^2$-{3-[(methylsulfonyl)methyl]phenyl}-2,4-pyrimidinediamine

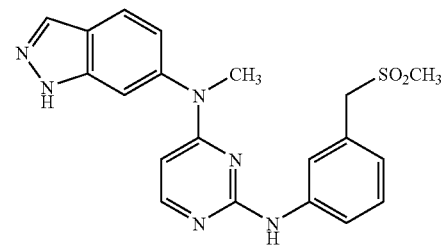

HNMR (400 MHz, d$_6$-DMSO) δ 13.15 (br s, 1H), 9.25 (br s, 1H), 8.10 (br s, 1H), 7.87-7.80 (m, 3H), 7.66 (d. 1H, J=9.74 Hz), 7.47 (s, 1H), 7.13 (t, 1H, J=7.90 Hz), 7.04 (d, 1H, J=8.33 Hz), 6.89 (d, 1H, J=7.34 Hz), 5.82 (d, 1H, J=5.93 Hz), 4.29 (s, 2H), 3.49 (s, 3H), 2.88 (s, 3H), MS (AP+, m/z) 409 (M+H).

Example 38

N$^4$-(1,3-dimethyl-1H-indazol-6-yl)-N$^4$-methyl-N$^2$-{3-[(methylsulfonyl)methyl]phenyl}-2,4-pyrimidinediamine

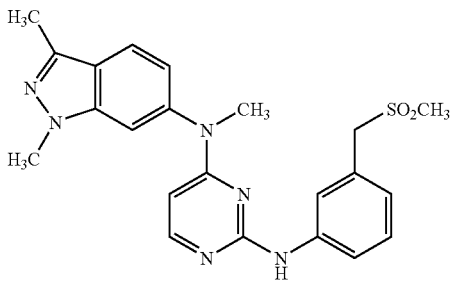

To a solution of N⁴-methyl-N⁴-(3-methyl-1H-indazol-6-yl)-N²-{3-[(methylsulfonyl)methyl]phenyl}-2,4-pyrimidinediamine (Example 23) (389 mg, 0.92 mmol) in DMF (4 ml) was added Cs$_2$CO$_3$ (600 mg, 1.84 mmol) followed by iodomethane (64 ul, 1.02 mmol). The mixture was stirred at rt overnight. The mixture was diluted with water and extracted with EtOAc. The organic layer was washed with brine, dried over MgSO$_4$, filtered and evaporated. Purification of crude product by prep TLC provided 260 mg of N⁴-(1,3-dimethyl-1H-indazol-6-yl)-N⁴-methyl-N²-{3-[(methylsulfonyl)methyl]-phenyl}-2,4-pyrimidinediamine. ¹H NMR (300 MHz, d$_6$DMSO) δ 9.25 (s, 1H), 7.86 (d, J=6.0 Hz, 1H), 7.82 (s, 1H), 7.77 (d, J=8.5 Hz, 1H), 7.65 (d, J=7.8 Hz, 1H), 7.58 (s, 1H), 7.15 (t, J=7.8 Hz, 1H), 7.02 (d, J=8.5 Hz, 1H), 6.89 (d, J=7.8 Hz, 1H), 5.83 (d, J=6.0 Hz, 1H), 4.28 (s, 2H), 3.92 (s, 3H), 3.49 (s, 3H), 2.87 (s, 3H), 2.48 (s, 3H). MS (ES+, m/z) 437 (M+H).

Example 39

N⁴-(2,3-dimethyl-2H-indazol-6-yl)-N⁴-methyl-N²-{3-[(methylsulfonyl)methyl]phenyl}-2,4-pyrimidinediamine

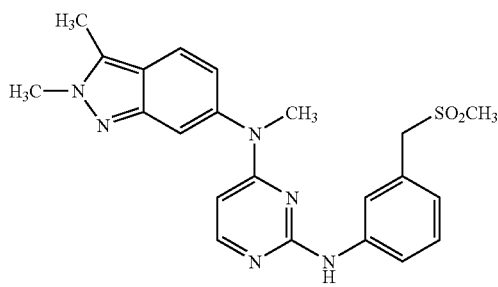

To a solution of N⁴-methyl-N⁴-(3-methyl-1H-indazol-6-yl)-N²-{3-[(methylsulfonyl)methyl]phenyl}-2,4-pyrimidinediamine (Example 23) (389 mg, 0.92 mmol) in DMF (4 ml) was added Cs$_2$CO$_3$ (600 mg, 1.84 mmol) followed by iodomethane (64 ul, 1.02 mmol). The mixture was stirred at rt overnight. The mixture was diluted with water and extracted with EtOAc. The organic layer was washed with brine, dried over MgSO$_4$, filtered and evaporated. Purification of crude product by prep TLC provided 120 mg N⁴-(2,3-dimethyl-2H-indazol-6-yl)-N⁴-methyl-N²-{3-[(methylsulfonyl)methyl]-phenyl}-2,4-pyrimidinediamine. ¹H NMR (300 MHz, d$_6$DMSO) δ 9.23 (s, 1H), 7.84-7.86 (m, 2H), 7.74 (d, J=8.8 Hz, 1H), 7.64 (d, J=7.9 Hz, 1H), 7.42 (s, 1H), 7.18 (t, J=7.8 Hz, 1H), 6.85-6.90 (m, 2H), 5.81 (d, J=5.8 Hz, 1H), 4.23 (s, 2H), 4.04 (s, 3H), 3.45 (s, 3H), 2.83 (s, 3H), 2.61 (s, 3H). MS (ES+, m/z) 437 (M+H).

Example 40

N⁴-(2,3-dimethyl-2H-indazol-6-yl)-N²-[5-(ethylsulfonyl)-2-methoxyphenyl]-N⁴-methyl-2,4-pyrimidinediamine

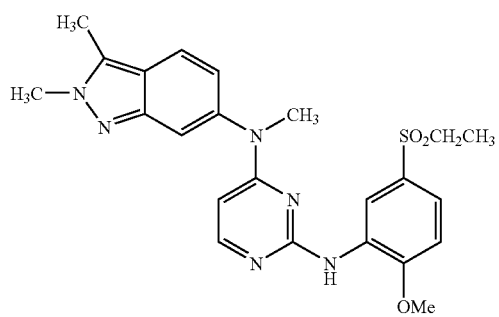

This example was prepared using procedures similar to those of Example 39. ¹H NMR (300 MHz, d$_6$DMSO) δ 9.15 (d, J=1.9 Hz, 1H), 7.88 (d, J=6.1 Hz, 1H), 7.79-7.81 (m, 2H), 7.47-7.50 (m, 2H), 7.28 (d, J=8.6 Hz, 1H), 6.95 (d, J=8.7 Hz, 1H), 5.81 (d, J=6.1 Hz, 1H), 4.08 (s, 3H), 4.03 (s, 3H), 3.53 (s, 3H), 3.22 (q, J=7.4 Hz, 2H), 2.65 (s, 3H), 1.13 (t, J=7.4 H, 3H). MS (ES+, m/z) 467 (M+H).

Example 41

1-[4-methoxy-3-({4-[(3-methyl-1H-indazol-6-yl)amino]-2-pyrimidinyl}amino)phenyl]-1-propanone

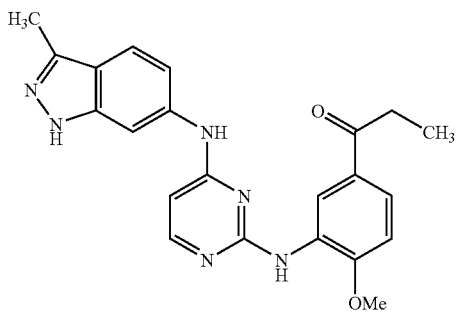

HNMR (400 MHz, d$_6$-DMSO) δ 12.45 (br s, 1H), 11.01 (br s, 1H), 9.90 (br s, 1H), 8.23 (s, 1H), 7.99 (d, 1H, J=6.78 Hz), 7.89 (d, 1H, J=7.33 Hz), 7.59 (br s, 1H), 7.51 (d, J=6.78 Hz), 7.30-7.27 (m, 2H), 6.52 (s, 1H), 3.93 (s, 3H), 2.66 (br s, 2H), 2.43 (s, 3H), MS (ES+, m/z) 403 (M+H).

Example 42

4-methoxy-N-[3-({4-[methyl(3-methyl-1H-indazol-6-yl)amino]-2-pyrimidinyl}amino)phenyl]benzenesulfonamide

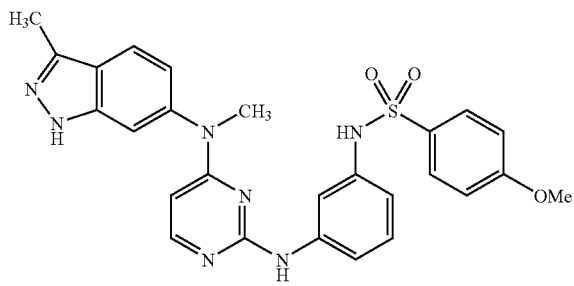

HNMR: δ 12.87 (s, 1H), 10.22 (s, 1H), 7.85 (d, J=8.5 Hz, 1H), 7.78 (d, J=7.2 Hz, 1H), 7.69 (d, J=8.8 Hz, 2H), 7.48 (s, 1H), 7.42 (s, 1H), 7.25 (d, J=7.7 Hz, 1H), 7.04 (d, J=8.8 Hz, 2H), 7.02 (d, J=8.5 Hz, 1H), 6.80 (d, J=8.1 Hz, 1H), 5.89 (d, J=7.2 Hz, 1H), 3.77 (s, 3H), 3.50 (s, 3H), 2.51 (s, 3H); MS (ES+, m/z)=516, 517 (M+H).

Example 43

4-methoxy-N-methyl-3-({4-[(3-methyl-1H-indazol-6-yl)amino]-2-pyrimidinyl}amino)benzenesulfonamide

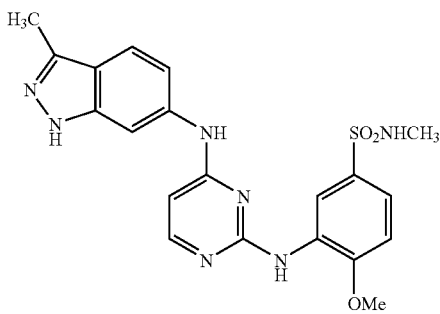

HNMR (400 MHz, d$_6$-DMSO) δ 12.31 (s, 1H), 9.59 (s, 1H), 8.72 (s, 1H), 8.03 (d, 1H, J=5.71 Hz), 7.89 (br s, 1H), 7.72 (s, 1H), 7.54 (d, 1H, J=8.56 Hz), 7.36 (d, 1H, J=8.38 Hz), 7.28-7.22 (m, 1H), 7.19-7.15 (m, 2H), 6.33 (d, 1H, J=5.89 Hz), 3.92 (s, 3H), 2.39 (s, 3H), 2.34 (d, 3H, J=4.99 Hz), MS (AP+, m/z) 440 (M+H).

Example 44

[(3-methyl-1H-indazol-6-yl)(2-{4-[(methylsulfonyl)methyl]anilino}-4-pyrimidinyl)amino]acetonitrile

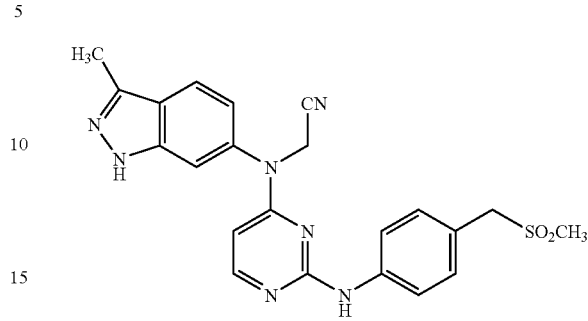

$^1$H NMR (300 MHz, d$_6$-DMSO) δ 12.83 (br s, 1H), 9.52 (s, 1H), 7.97 (d, J=5.9 Hz, 1H), 7.86 (d, J=8.3 Hz, 1H), 7.78 (d, J=8.5 Hz, 2H), 7.47 (s, 1H), 7.27 (d, J=8.5 Hz, 2H), 7.03 (dd, J=8.5 & 1.5 Hz, 1H), 5.78 (d, J=5.9 Hz, 1H), 5.02 (s, 2H), 4.37 (s, 2H), 2.86 (s, 3H), 2.51 (s, 3H). MS (ES+, m/z) 448 (M+H).

Example 45

[{2-[5-(ethylsulfonyl)-2-methoxyanilino]-4-pyrimidinyl}(3-methyl-1H-indazol-6-yl)amino]acetonitrile

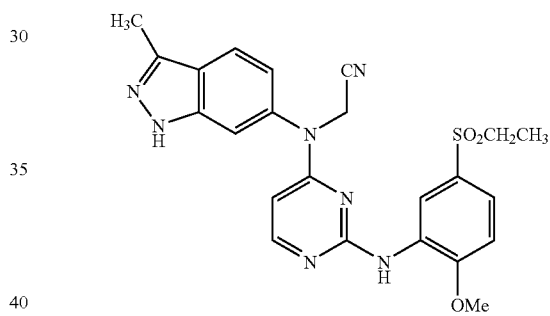

$^1$H NMR (300 MHz, d$_6$-DMSO) δ 12.85 (br s, 1H), 8.98 (d, J=2.2 Hz, 1H), 8.08 (s, 1H), 8.00 (d, J=5.9 Hz, 1H), 7.87 (d, J=8.5 Hz, 1H), 7.52-7.49 (m, 2H), 7.29 (d, J=8.8 Hz, 1H), 7.03 (dd, J=8.5 & 1.4 Hz, 1H), 5.80 (d, J=5.9 Hz, 1H), 5.08 (s, 2H), 4.00 (s, 3H), 3.22 (q, J=7.3 Hz, 2H), 2.51 (s, 3H), 1.12 (t, J=7.4 Hz, 3H). MS (ES+, m/z) 478 (M+H).

Example 46

[(3-methyl-1H-indazol-6-yl)(2-{3-[(methylsulfonyl)methyl]anilino}-4-pyrimidinyl)amino]acetonitrile

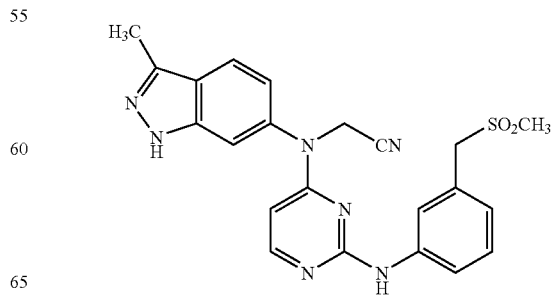

¹H NMR (300 MHz, d₆-DMSO) δ 12.83 (br s, 1H), 9.53 (s, 1H), 7.96 (m, 2H), 7.86 (d, j=8.4 Hz, 1H), 7.62 (d, J=8.4 Hz, 1H), 7.47 (s, 1H), 7.26 (t, J=7.8 Hz, 1H), 7.04-6.96 (m, 2H), 5.76 (d, J=5.8 Hz, 1H), 5.02 (s, 2H), 4.39 (s, 2H), 2.90 (s, 3H), 2.51 (s, 3H). MS (ES+, m/z) 448 (M+H).

Example 47

4-methoxy-N-methyl-3-({4-[methyl(3-methyl-1H-indazol-6-yl)amino]-2-pyrimidinyl}amino)benzene-sulfonamide

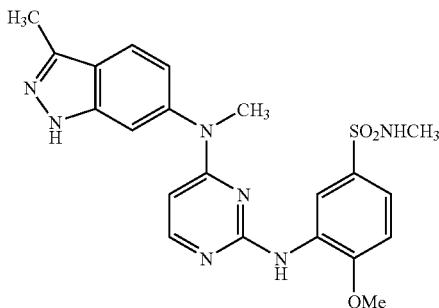

¹H NMR (400 MHz, d₆DMSO) δ 12.70 (br s, 1H), 8.99 (d, J=2.2 Hz, 1H), 7.74-7.80 (m, 3H), 7.32-7.36 (m, 2H), 7.15-7.18 (m, 2H), 6.97 (d, J=8.4 Hz, 1H), 5.73 (d, J=6.0 Hz), 3.92 (s, 3H), 3.47 (s, 3H), 2.45 (s, 3H), 2.36 (d, J=5.0 Hz, 3H). MS (ES+, m/z) 454 (M+H).

Example 48

4-({4-[methyl(3-methyl-1H-indazol-6-yl)amino]-2-pyrimidinyl}amino)benzamide

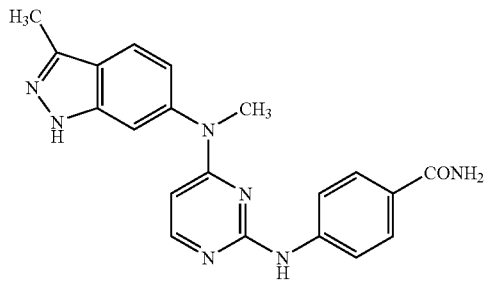

¹H NMR (300 MHz, d₆-DMSO) δ 12.72 (br s, 1H), 9.45 (s, 1H), 7.89 (d, J=6.0 Hz, 1H), 7.78-7.81 (m, 2H), 7.69-7.72 (m, 2H), 7.41 (s, 1H), 7.09 (br s, 1H), 7.03 (d, J=8.5 Hz, 1H), 5.85 (d, J=6.0 Hz, 1H), 3.50 (s, 3H), 2.50 (s, 3H). MS (ES+, m/z) 374 (M+H).

Example 49

3-methoxy-4-({4-[methyl(3-methyl-1H-indazol-6-yl)amino]-2-pyrimidinyl}amino)benzenesulfonamide

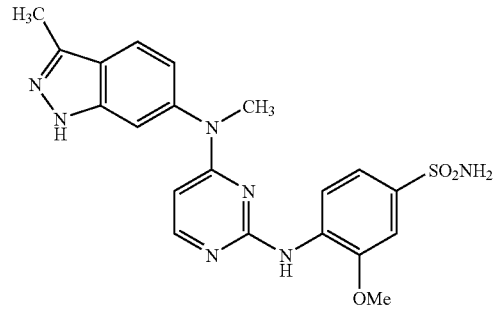

¹H NMR (300 MHz, d₆DMSO) δ 12.92 (br s, 1H), 9.53 (d, J=2.2 Hz, 1H), 7.97-8.04 (m, 2H), 7.91 (s, 1H), 7.59-7.64 (m, 2H), 7.34-7.38 (m, 3H), 7.20 (dd, J=8.6 & 1.5 Hz, 1H), 5.96 (d, J=6.0 Hz, 1H), 4.14 (s, 3H), 3.69 (s, 3H), 2.68 (s, 3H). MS (ES+, m/z) 440 (M+H).

Example 50

N⁴-ethynyl-N⁴-(3-methyl-1H-indazol-6-yl)-N²-{3-[(methylsulfonyl)methyl]phenyl}-2,4-pyrimidinediamine

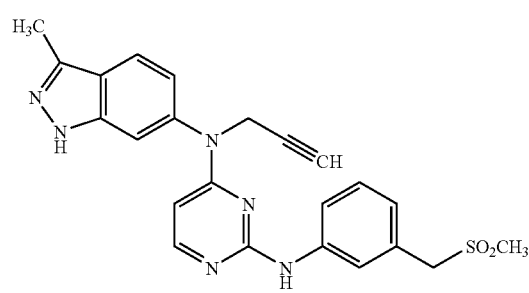

¹H NMR (300 MHz, d₆-DMSO) δ 12.99 (br s, 1H), 9.57 (s, 1H), 8.08-8.10 (m, 2H), 7.99 (d, J=8.4 Hz, 1H), 7.86 (d, J=8.4 Hz, 1H), 7.63 (s, 1H), 7.38 (t, J=7.8 Hz, 1H), 7.19-7.23 (m, 1H), 7.12 (d, J=7.5 Hz, 1H), 5.94 (d, J=4.7 Hz, 1H), 5.94 (s, 2H), 4.95 (s, 2H), 3.08 (s, 3H), 2.68 (s, 3H). MS (ES+, m/z) 447 (M+H).

Example 51

3-({4-[(3-methyl-1H-indazol-6-yl)(2-propynyl)amino]-2-pyrimidinyl}amino)benzenesulfonamide

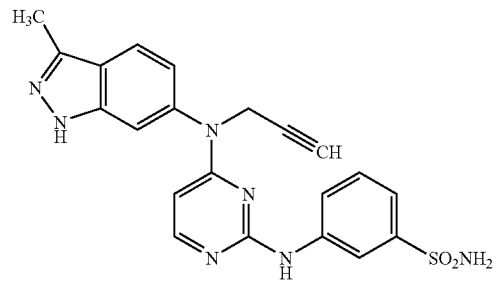

HNMR (400 MHz, d$_6$-DMSO): δ 12.76 (br s, 1H), 9.62 (s, 1H), 8.29 (br s, 1H), 7.97 (br s, 1H), 7.92 (d, 1H, J=5.8), 7.81 (d, 1H, J=8.6), 7.45 (s, 1H), 7.34 (d, 1H, J=4.2), 7.26 (s, 2H), 7.03 (d, 1H, J=8.4), 5.76 (d, 1H, J=5.9), 4.80 (s, 2H), 3.18 (s, 1H), 2.88 (m, 2H), 2.49 (s, 3H); MS (ES+, m/z)=455 (M+H).

Example 52

4-({4-[methyl(3-methyl-1H-indazol-6-yl)amino]-2-pyrimidinyl}amino)benzenesulfonamide

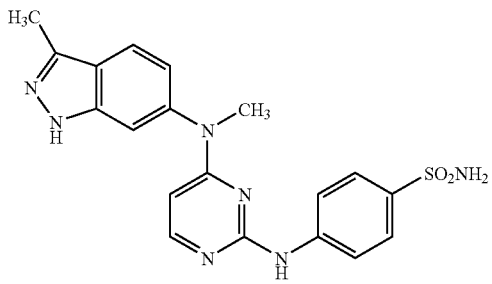

$^1$H NMR (300 MHz, d$_6$DMSO) δ 12.91 (br s, 1H), 9.77 (s, 1H), 8.10 (d, J=6.1 Hz, 1H), 8.04 (d, J=8.8 Hz, 2H), 7.98 (d, J=8.5 Hz, 1H), 7.78 (d, J=8.8 Hz, 2H), 7.59 (s, 1H), 7.29 (br s, 2H), 7.20 (dd, J=8.5 & 1.5 Hz, 1H), 6.08 (d, J=6.1 Hz, 1H), 3.68 (s, 3H), 2.69 (s, 3H). MS (ES+, m/z) 410 (M+H).

Example 53

N$^4$-methyl-N$^4$-(3-methyl-1H-indazol-6-yl)-N$^2$-[3-(methylsulfonyl)phenyl]-2,4-pyrimidinediamine

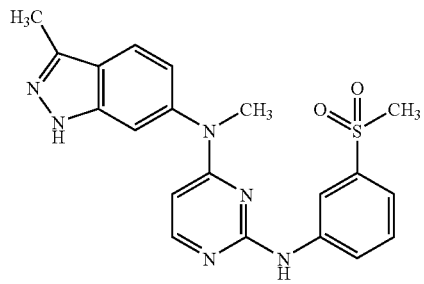

$^1$H NMR (300 MHz, d$_6$DMSO) δ 12.75 (br s, 1H), 9.65 (s, 1H), 8.69 (s, 1H), 7.87-7.89 (m, 2H), 7.80 (d, J=8.4 Hz, 1H), 7.41 (m, 3H), 7.03 (d, J=8.2 Hz, 1H), 5.82 (d, J=5.8 Hz, 1H), 3.52 (s, 3H), 3.16 (s, 3H), 2.51 (s, 3H). MS (ES+, m/z) 409 (M+H).

Example 54

4-methoxy-3-({4-[methyl(3-methyl-1H-indazol-6-yl)amino]-2-pyrimidinyl}amino)benzenesulfonamide

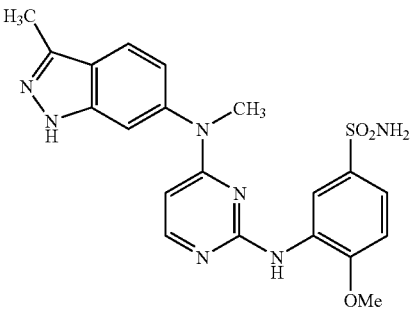

$^1$H NMR (300 MHz, d$_6$DMSO) δ 9.95 (br s, 1H), 8.73 (br s, 1H), 7.86-7.91 (m, 2H), 7.68 (d, J=8.8 Hz, 1H), 7.55 (s, 1H), 7.30-7.34 (m, 3H), 7.08 (d, J=8.5 Hz, 1H), 5.88 (d, J=7.4 Hz, 1H), 3.97 (s, 3H), 3.58 (s, 3H), 2.52 (s, 3H). MS (ES+, m/z) 440 (M+H).

Example 55

N$^2$-[5-(ethylsulfonyl)-2-methoxyphenyl]-N$^4$-(3-methyl-1H-indazol-6-yl)-2,4-pyrimidinediamine

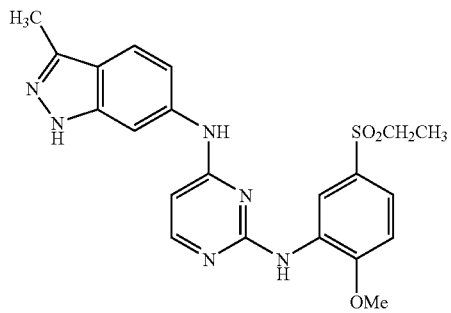

HNMR (400 MHz, d$_6$-DMSO) δ 11.42 (br s, 1H), 10.19 (br s 1H), 7.96 (d, 2H, J=7.14 Hz), 7.74 (dd, 1H, J=1.92 Hz and J=8.7 Hz), 7.53 (br s, 1H), 7.39 (d, 1H, J=8.79 Hz), 7.32 (br, s, 1H), 6.64 (br s, 1H), 3.88 (s, 3H), 2.96 (br s, 2H), 2.39 (s, 3H), 0.90 (br s, 3H), MS (ES−, m/z) 437 (M−H).

Example 56

3-({4-[methyl(3-methyl-1H-indazol-6-yl)amino]-2-pyrimidinyl}amino)benzamide

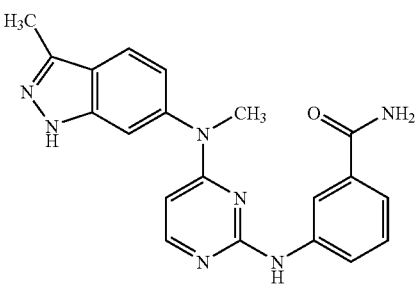

<sup>1</sup>H NMR (300 MHz, d<sub>6</sub>DMSO) δ 12.83 (s, 1H), 9.84 (br s, 1H), 8.29 (s, 1H), 7.92-7.84 (m, 3H), 7.78 (d, J=7.7 Hz, 1H), 7.51-7.48 (m, 2H), 7.34-7.26 (m, 2H), 7.07 (d, J=8.5 Hz, 1H), 5.89 (d, J=6.4 Hz, 1H), 3.55 (s, 3H), 2.54 (s, 3H). MS (ES+, m/z) 374 (M+H).

Example 57

N$^2$-[4-(ethylsulfonyl)phenyl]-N$^4$-methyl-N$^4$-(3-methyl-1H-indazol-6-yl)-2,4-pyrimidinediamine

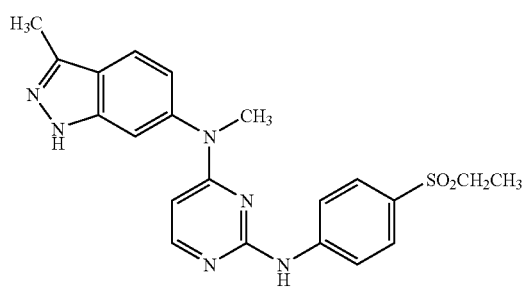

<sup>1</sup>H NMR (300 MHz, d<sub>6</sub>-DMSO) δ 12.73 (s, 1H), 9.75 (s, 1H), 7.89-7.95 (m, 3H), 7.81 (d, J=8.5 Hz, 1H), 7.58 (d, J=8.8 Hz, 2H), 7.41 (s, 1H), 7.03 (dd, J=8.5 & 1.5 Hz, 1H), 5.96 (d, J=6.0 Hz, 1H), 3.50 (s, 3H), 3.16 (q, J=7.3 Hz, 2H), 2.52 (s, 3H), 1.07 (t, J=7.3 Hz, 3H). MS (ES+, m/z) 423 (M+H).

Example 58

N-[4-({4-[methyl(3-methyl-1H-indazol-6-yl)amino]-2-pyrimidinyl}amino)benzyl]ethanesulfonamide

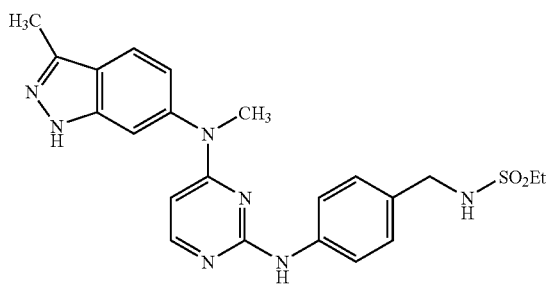

<sup>1</sup>H NMR (400 MHz, d<sub>6</sub>-DMSO) δ 12.7 (s, 1H), 9.17 (s, 1H), 7.85 (d, J=6.0 Hz, 1H), 7.78 (d, J=8.4 Hz, 1H), 7.67 (d, J=8.6 Hz, 2H), 7.47 (t, J=6.4 Hz, 1H), 7.38 (s, 1H), 7.12 (d, J=8.4 Hz, 2H), 7.0 (dd, J=1.6 Hz, J=8.4 Hz, 1H), 5.79 (d, J=6.0 Hz, 1H), 4.02 (d, J=6.2 Hz, 2H), 3.47 (s, 3H), 2.87 (q, J=7.3 Hz, 2H), 2.51 (s, 3H), 1.13 (t, J=7.3 Hz, 3H).

Example 59

N-[3-({4-[methyl (3-methyl-1H-indazol-6-yl)amino]-2-pyrimidinlyl}amino)benzyl]methanesulfonamide

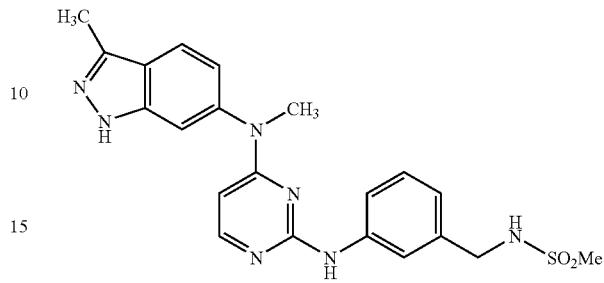

<sup>1</sup>H NMR (400 MHz, d<sub>6</sub>-DMSO) δ 12.7 (s, 1H), 9.21 (s, 1H), 7.84 (d, J=5.8 Hz, 1H), 7.78 (d, J=8.4 Hz, 1H), 7.78 (d, J=8.4 Hz, 1H), 7.57 (d, J=7.8 Hz, 1H), 7.48 (t, J=6.3 Hz, 1H), 7.38 (s, 1H), 7.12 (t, J=7.8 Hz, 1H), 7.0 (dd, J=1.6 Hz, J=8.4 Hz, 1H), 6.85 (d, J=7.5 Hz, 1H), 5.79 (d, J=5.8 Hz, 1H), 4.02 (d, J=6.2 Hz, 2H), 3.49 (s, 3H), 2.84 (2, 3H), 2.51 (s, 3H).

Example 60

2-chloro-5-({4-[methyl(3-methyl-1H-indazol-6-yl)amino]-2-pyrimidinyl}amino)benzenesulfonamide

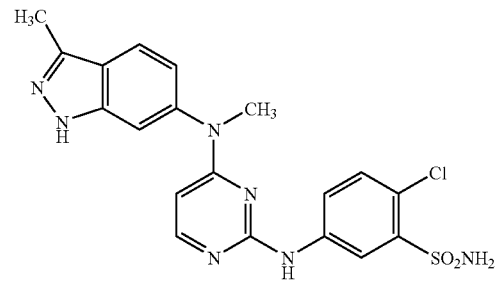

<sup>1</sup>H NMR (300 MHz, d<sub>6</sub>-DMSO) δ 12.73 (s, 1H), 9.65 (s, 1H), 8.73 (d, J=2.1 Hz, 1H), 7.79-7.87 (m, 2H), 7.34-7.46 (m, 3H), 7.02 (d, J=8.2 Hz, 1H), 5.81 (d, J=6.0 Hz, 1H), 3.51 (s, 3H), 2.51 (s, 3H). MS (ES+, m/z) 444 (M+H).

Example 61

2-chloro-4-({4-[methyl(3-methyl-1H-indazol-6-yl)amino]-2-pyrimidinyl}amino)benzenesulfonamide

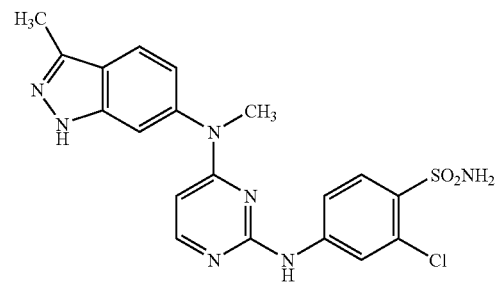

¹H NMR (300 MHz, d₆-DMSO) δ 12.73 (s, 1H), 9.76 (s, 1H), 8.11 (s, 1H), 7.95 (d, J=6.0 Hz, 1H), 7.80 (d, J=8.6 Hz, 1H), 7.64-7.73 (m, 2H), 7.41 (s, 1H), 7.33 (s, 2H), 7.03 (d, J=8.3 Hz, 1H), 5.95 (d, J=6.0 Hz, 1H), 3.49 (s, 3H), 2.51 (s, 3H). MS (ES+, m/z) 444 M+H).

Example 62

4-chloro-3-({4-[methyl(3-methyl-1H-indazol-6-yl)amino]-2-pyrimidinyl}amino)benzenesulfonamide

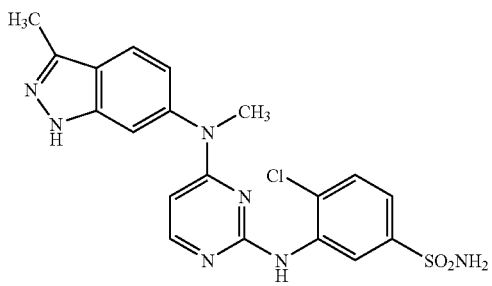

¹H NMR (300 MHz, d₆-DMSO) δ 12.73 (s, 1H), 8.85 (d, J=2.1 Hz, 1H), 8.28 (s, 1H), 7.78-7.85 (m, 2H), 7.69 (d, J=8.4 Hz, 1H), 7.40-7.48 (m, 4H), 7.01 (d, J=8.5 Hz. 1H), 5.80 (d, J=7.4 Hz, 1H), 3.46 (s, 3H), 2.50 (s, 3H). MS (ES+, m/z) 444 (M+H).

Example 63

3-methyl-4-({4-[methyl(3-methyl-1H-indazol-6-yl)amino]-2-pyrimidinyl}amino)benzenesulfonamide

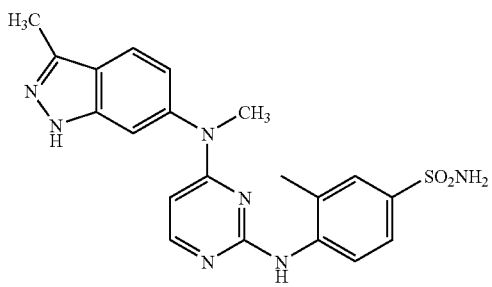

¹H NMR (300 MHz, d₆-DMSO) δ 12.84 (br s, 1H), 9.33 (br s, 1H), 7.82-7.92 (m, 3H), 7.69 (s, 1H), 7.59 (m, 1H), 7.46 (s, 1H), 7.27 (s, 2H), 7.04 (dd, J=8.5 & 1.3 Hz, 5.90 (d, J=5.1 Hz, 1H), 3.46 (s, 3H), 2.51 (s, 3H), 2.36 (s, 3H). MS (ES+, m/z) 424 (M+H).

Example 64

2-methyl-5-({4-[methyl(3-methyl-1H-indazol-6-yl)amino]-2-pyrimidinyl}amino)benzenesulfonamide

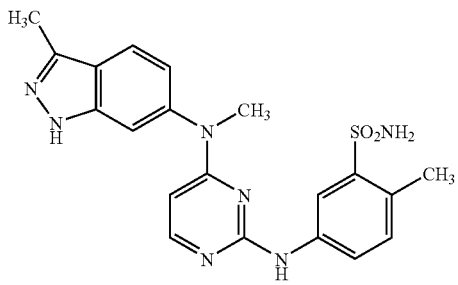

¹H NMR (300 MHz, d₆-DMSO) δ 12.71 (br s, 1H), 9.38 (s, 1H), 8.55 (s, 1H), 7.67-7.87 (m, 3H), 7.37 (s, 1H), 7.21 (s, 1H), 7.11 (d, J=8.4 Hz, 1H), 6.99 (d, J=8.5 Hz, 1H), 5.74 (d, J=5.8 Hz, 1H), 3.48 (s, 3H), 2.49 (s, 3H), 2.47 (s, 3H). MS (ES+, m/z) 424 (M+H).

Example 65

4-methyl-3-({4-[methyl(3-methyl-1H-indazol-6-yl)amino]-2-pyrimidinyl}amino)benzenesulfonamide

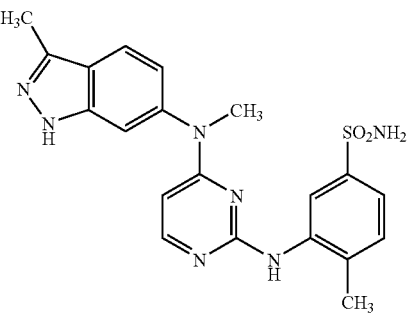

¹H NMR (300 MHz, d₆-DMSO) δ 12.71 (br s, 1H), 10.25 (s, 1H), 8.30 (s, 1H), 7.82-7.89 (m, 2H), 7.62 (d, J=7.9 Hz, 1H), 7.50-7.52 (m, 2H), 7.38 (s, 2H), 7.05 (d, J=9.5 Hz, 1H), 5.84 (d, J=7.2 Hz, 1H), 3.46 (s, 3H), 2.51 (s, 3H), 2.39 (s, 3H). MS (ES+, m/z) 424 (M+H).

Example 66

N⁴-methyl-N⁴-(3-methyl-1H-indazol-6-yl)-N²-[3-(methylsulfinyl)phenyl]-2,4-pyrimidinediamine

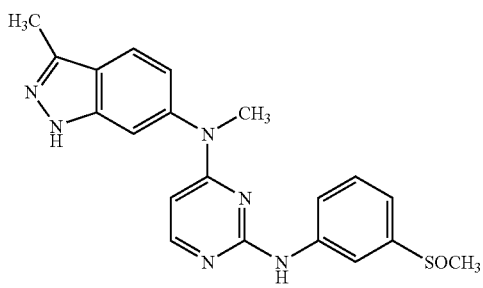

$^1$H NMR (300 MHz, d$_6$-DMSO) δ 12.72 (s, 1H), 9.50 (s, 1H), 8.29 (s, 1H), 7.89 (d, J=5.9 Hz, 1H), 7.79 (d, J=8.5 Hz, 1H), 7.70 (d, J=7.9 Hz, 1H), 7.40 (s, 1H), 7.33 (m, 1H), 7.12 (d, J=7.7 Hz, 1H), 7.07 (d, J=8.5 Hz, 1H), 5.84 (d, J=6.0 Hz, 1H), 3.50 (s, 3H), 2.51 (s, 3H). MS (ES+, m/z) 393 (M+H).

Example 67

N$^2$-[2-fluoro-5-(methylsulfonyl)phenyl]-N$^4$-methyl-N$^4$-(3-methyl-1H-indazol-6-yl)-2,4-pyrimidinediamine

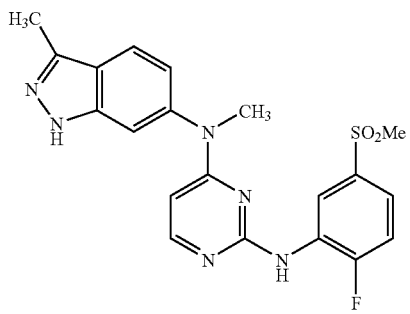

$^1$H NMR (300 MHz, d$_6$-DMSO) δ 12.76 (br s, 1H), 9.07 (s, 1H), 8.89 (s, 1H), 7.79-7.85 (m, 2H), 7.42-7.59 (m, 3H), 7.02 (m, 1H), 5.82 (m, 1H), 3.48 (s, 3H), 3.20 (s, 3H), 2.50 (s, 3H). MS (ES+, m/z) 427 (M+H).

Example 68

N$^2$-[2-methoxy-5-(methylsulfonyl)phenyl]-N$^4$-methyl-N$^4$-(3-methyl-1H-indazol-6-yl)-2,4-pyrimidinediamine

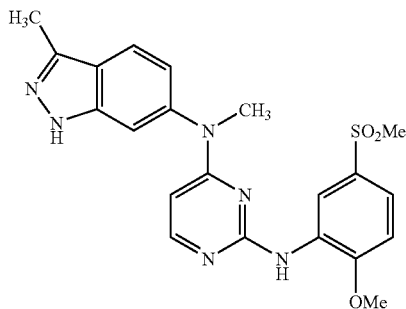

HNMR: δ 12.74 (s, 1H), 9.13 (s, 1H), 7.85 (d, J=6.0 Hz, 1H), 7.80 (s, 1H), 7.79 (d, J=10.3 Hz, 1H), 7.46 (dd, J=2.2, 8.6 Hz, 1H), 7.40 (s, 1H), 7.24 (d, J=8.6 Hz, 1H), 7.00 (d, J=8.4 Hz, 1H), 5.78 (d, J=6.1 Hz, 1H), 3.97 (s, 3H), 3.50 (s, 3H), 3.11 (s, 3H), 2.48 (s, 3H); MS (ES+, m/z)=439 (M+H).

Example 69

5-({4-[(2,3-dimethyl-2H-indazol-6-yl)(methyl)amino]pyrimidin-2-yl}amino)-2-methylbenzenesulfonamide

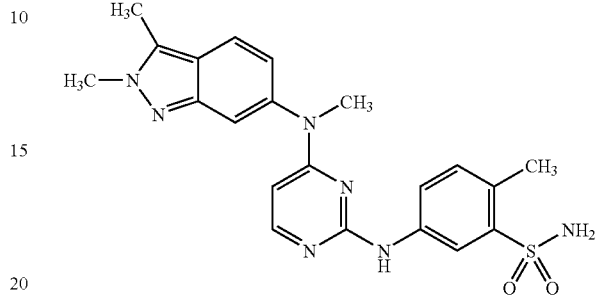

To a solution of Intermediate Example 13 (200 mg, 0.695 mmol) and 5-amino-2-methylbenzenesulfonamide (129.4 mg, 0.695 mmol) in isopropanol (6 ml) was added 4 drops of conc. HCl. The mixture was heated to reflux overnight. The mixture was cooled to rt and diluted with ether (6 ml). Precipitate was collected via filtration and washed with ether. HCl salt of 5-({4-[(2,3-dimethyl-2H-indazol-6-yl)(methyl)amino]-pyrimidin-2-yl}amino)-2-methylbenzenesulfonamide was isolated as an off-white solid. $^1$H NMR (400 MHz, d$_6$DMSO+NaHCO$_3$) δ 9.50 (br s, 1H), 8.55 (br s, 1H), 7.81 (d, J=6.2 Hz, 1H), 7.75 (d, J=8.7 Hz, 1H), 7.69 (m, 1H), 7.43 (s, 1H), 7.23 (s, 2H), 7.15 (d, J=8.4 Hz, 1H), 6.86 (m, 1H), 5.74 (d, J=6.1 Hz, 1H), 4.04 (s, 3H), 3.48 (s, 3H), 2.61 (s, 3H), 2.48 (s, 3H). MS (ES+, m/z) 438 (M+H).

Examples 70-72 were prepared according to the general procedures set forth above in Example 69.

Example 70

3-({4-[(2,3-dimethyl-2H-indazol-6-yl)(methyl)amino]pyrimidin-2-yl}amino)benzenesulfonamide

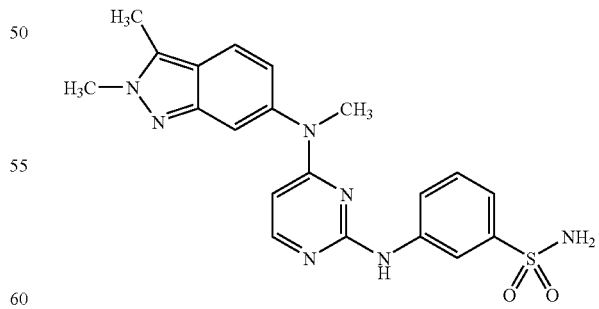

$^1$H NMR (400 MHz, d$_6$DMSO+NaHCO$_3$) δ 9.58 (br s, 1H), 8.55 (br s, 1H), 7.83 (d, J=6.2 Hz, 1H), 7.74-7.79 (m, 2H), 7.43 (s, 1H), 7.34-7.37 (m, 2H), 7.24 (s, 2H), 6.86 (m, 1H), 5.77 (d, J=6.1 Hz, 1H), 4.04 (s, 3H), 3.48 (s, 3H), 2.61 (s, 3H). MS (ES+, m/z) 424 (M+H).

Example 71

2-[4-({4-[(2,3-dimethyl-2H-indazol-6-yl)(methyl)amino]pyrimidin-2-yl}amino)phenyl]ethanesulfonamide

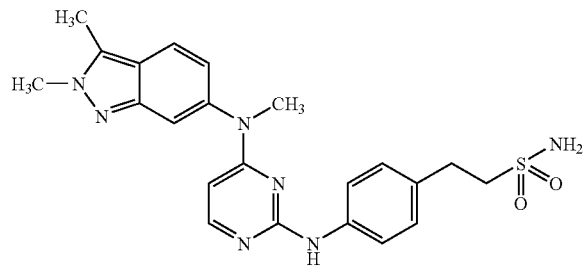

$^1$H NMR (300 MHz, d$_6$DMSO+NaHCO$_3$) δ 9.10 (br s, 1H), 7.83 (d, J=6.0 Hz, 1H), 7.75 (d, J=8.7 Hz, 1H), 7.67 (d, J=8.5 Hz, 2H), 7.43 (d, J=1.1 Hz, 1H), 7.06 (d, J=8.5 Hz, 2H), 6.86-6.89 (m, 3H), 5.76 (d, J=6.0 Hz, 1H), 4.06 (s, 3H), 3.46 (s, 3H), 3.21 (m, 2H), 2.91 (m, 2H), 2.62 (s, 3H). MS (ES+, m/z) 452 (M+H).

Example 72

N$^4$-(2,3-dimethyl-2H-indazol-6-yl)-N$^4$-methyl-N$^2$-{4-[(methylsulfonyl)methyl]phenyl}pyrimidine-2,4-diamine

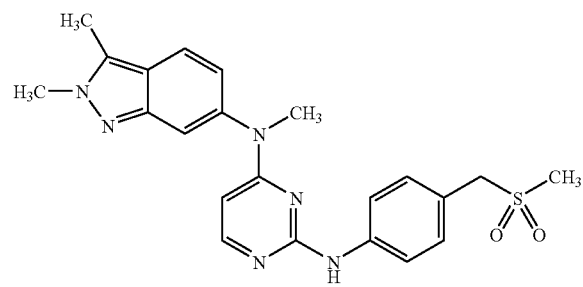

$^1$H NMR (300 MHz, d$_6$DMSO+NaHCO$_3$) δ 9.37 (bs, 1H), 7.88 (d, J=6.1 Hz, 1H), 7.78 (m, 3H), 7.47 (s, 1H), 7.22 (d, J=8.5 Hz, 2H), 6.91 (dd, J=8.8, 1.5 Hz, 1H), 5.84 (d, J=6.1 Hz, 1H), 4.37 (s, 2H), 4.09 (s, 3H), 3.51 (s, 3H), 2.88 (s, 3H), 2.65 (s, 3H). MS (ES+, m/z) 437 (M+H), 435 (M–H).

Example 73

3-({4-[[3-(hydroxymethyl)-2-methyl-2H-indazol-6-yl](methyl)amino]pyrimidin-2-yl}amino)benzenesulfonamide

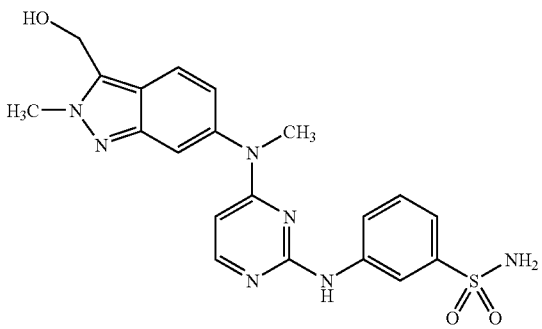

To a solution of 2,3-dimethyl-6-nitro-2H-indazole (3.00 g, 15.69 mmol) in CCl$_4$ (500 mL) was added AIBN (0.51 g, 3.14 mmol) and NBS (3.06 g, 17.26 mmol). The mixture was heated to 80° C. for 5 hours then stirred at rt overnight. Approximately half of the solvent was removed in vacuo, and the mixture was filtered. The filtrate was conc. in vacuo, and the crude product was purified by silica gel column chromatography eluting with ethyl acetate and hexane to afford 3-(bromomethyl)-2-methyl-6-nitro-2H-indazole with some succinimide present (4.41 g, 104% TY). $^1$H NMR (300 MHz, CDCl$_3$) δ 8.68 (d, J=2.1 HZ, 1H), 7.98 (dd, J=9.3, 2.1 Hz, 1H), 7.74 (d, J=9.3 Hz, 1H), 4.87 (s, 2H), 4.28 (s, 3H). MS (ES+, m/z) 270, 272 (M+H).

3-(Bromomethyl)-2-methyl-6-nitro-2H-indazole (4.20 g, ~14.9 mmol) in CH$_3$CN (500 ml) and water (200 ml) was treated with NaOH to give pH~11. The solution was stirred at rt for 2 days then conc. in vacuo and repeatedly extracted with dichloromethane and chloroform. The combined organic extracts were evaporated, and the crude product was purified by silica gel column chromatography to give (2-methyl-6-nitro-2H-indazol-3-yl)methanol (1.03 g, 33% TY). MS (ES+, m/z) 208.

Under anhydrous conditions and nitrogen atmosphere, give (2-methyl-6-nitro-2H-indazol-3-yl)methanol (1.03 g, 4.97 mmol) in CH$_2$Cl$_2$ (50 ml) was treated with triethylamine (0.58 g, 5.47 mmol) and DMAP (64 mg, 0.50 mmol) followed by chlorotriphenylmethane (1.42 g, 5.07 mmol). The resulting solution was stirred under nitrogen at rt for 20 hours then diluted with CH$_2$Cl$_2$ and washed with water. Concentration in vacuo followed by silica gel chromatography eluting with CH$_2$Cl$_2$ provided 2-methyl-6-nitro-3-[(trityloxy)methyl]-2H-indazole (1.09 g, 49% TY). $^1$H NMR (300 MHz, CDCl$_3$) δ 8.66 (d, J=2.1 HZ, 1H), 7.88 (dd, J=9.3, 2.1 Hz, 1H), 7.55 (d, J=9.3 Hz, 1H), 7.50 (m, 6H), 7.1-7-4 (m, 9H), 4.52 (s, 2H), 4.13 (s, 3H). MS (ES+, m/z) 450 (M+H).

To a solution of 2-methyl-6-nitro-3-[(trityloxy)methyl]-2H-indazole (0.50 g, 1.11 mmol) in anhydrous THF under nitrogen atmosphere at 0° C. was added LiAlH$_4$ (2.7 ml, 1.0 M in THF, 2.7 mmol). The solution was stirred at 0° C. for ~3 h then cooled to –78° C. and quenched with wet THF. The resulting mixture was conc. in vacuo then repeatedly triturated with CH$_3$CN. The combined CH$_3$CN was conc. in vacuo to give crude 2-methyl-3-[(trityloxy)methyl]-2H-indazol-6-amine (0.593 g, 108% TY). MS (ES+, m/z) 420 (M+H).

2-Methyl-3-[(trityloxy)methyl]-2H-indazol-6-amine was utilized in the manner described above for Intermediate Example 12 and 13 and according to the general procedures set forth above for Example 69. Purification by preparative HPLC and isolation by lyophilization provided the trifluoroacetate salt of 3-({4-[[3-(hydroxymethyl)-2-methyl-2H-indazol-6-yl](methyl)amino]pyrimidin-2-yl}amino)-benzenesulfonamide as a tan solid. $^1$H NMR (300 MHz, d$_6$DMSO+ NaHCO$_3$) δ 9.53 (s, 1H), 8.57 (s, 1H), 7.85 (m, 2H), 7.79 (d, J=7.2 Hz, 1H), 7.51 (s, 1H), 7.36 (m, 2H), 7.25 (s, 1H), 6.95 (d, J=8.9 Hz, 1H), 5.78 (d, J=6.0 Hz, 1H), 5.47 (t, J=5.4 Hz, 1H), 4.92 (d, J=5.4 Hz, 2H), 4.14 (s, 3H), 3.50 (s, 3H). MS (ES+, m/z) 440 (M+H), 438 (M−H).

Example 74

3-({4-[(1,2-dimethyl-1H-benzimidazol-5-yl)(methyl) amino]pyrimidin-2-yl}amino)benzenesulfonamide

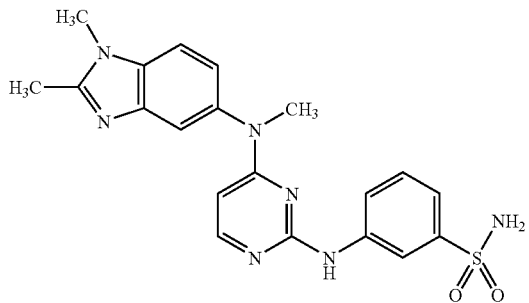

Intermediate Example 21 (200 mg) was combined with 100 mg of 3-aminobenenesulfonamide in 5.0 mL of isopropanol with 3 drops of aqueous HCl. The reaction was heated to 80° C. and followed by TLC. When the reaction was judged to be complete based upon consumption the Intermediate Example 21, the reaction was quenched with solid sodium bicarbonate while warm, then allowed to cool to room temperature. The complete reaction mixture was then coated onto silica gel and chromatographed on silica gel using CH$_2$Cl$_2$ and MeOH as eluent affording 223 mg of product. 1H NMR (400 MHz, d$_6$DMSO) δ 9.50 (s, 1H), 8.59 (s, 1H), 7.80 (d, J=6.06 Hz, 1H), 7.77 (s, 1H), 7.57 (d, J=8.56 Hz, 1H), 7.46 (d, J=1.78 Hz, 1H), 7.35 (m, 2H), 7.25 (s, 2H), 7.12 (dd, J=8.38, 1.96 Hz, 1H), 5.62 (d, J=5.71 Hz, 1H), 3.76 (s, 3H), 3.48 (s, 3H), 2.54 (s, 3H). MS (ESI) (M+H)$^+$ 424.

Example 75

3-({4-[(2-benzyl-1-methyl-1H-benzimidazol-5-yl) (methyl)amino]pyrimidin-2-yl}amino)benzenesulfonamide

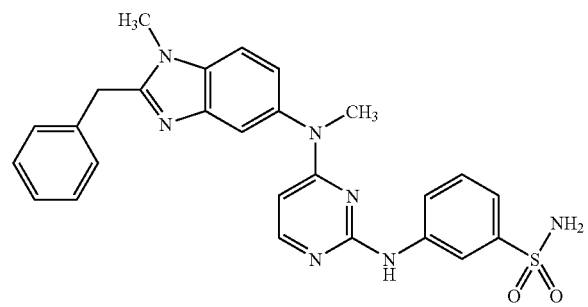

Example 75 was prepared by the similar procedure set forth at the Example 74 wherein Intermediate Example 18 was used instead of Intermediate Example 17 for the synthesis of Intermediate Example 21. 1H NMR (400 MHz, d$_6$DMSO) δ 9.49 (s, 1H) 8.57 (s, 1H) 7.79 (d, J=6.06 Hz, 1H) 7.76 (m, 1H) 7.57 (d, J=8.56 Hz, 1H) 7.52 (d, J=1.78 Hz, 1H) 7.30 (m, 5H) 7.22 (m, 4H) 7.14 (dd, J=8.38, 1.96 Hz, 1H) 5.64 (d, J=5.71 Hz, 1H) 4.31 (s, 2H) 3.72 (s, 3H) 3.47 (s, 3H).

Example 76

3-({4-[(2-ethyl-3-methyl-2H-indazol-6-yl)(methyl) amino]pyrimidin-2-yl}amino)benzenesulfonamide

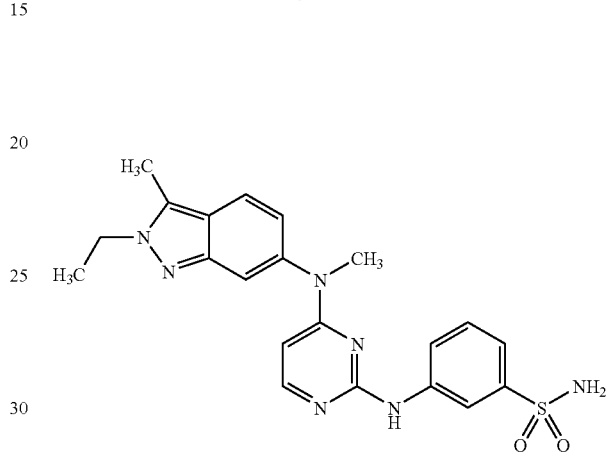

Example 76 was prepared according to the general procedure outlined in Example 69 wherein triethyloxonium hexafluorophosphate was used instead of trimethyloxonium tetrafluoroborate in the synthesis of Intermediate Example 11. $^1$H NMR (400 MHz, d$_6$DMSO) δ 8.39 (br s, 1H), 7.83 (m, 2H), 7.73 (m, 1H), 7.49-7.55 (m, 3H), 7.36 (s, 2H), 6.90 (d, J=8.6 Hz, 1H), 5.90 (m, 1H), 4.38 (q, J=7.1 Hz, 2H), 3.52 (s, 3H), 2.64 (s, 3H), 1.42 (t, J=7.1 Hz, 3H). MS (ES+, m/z) 438 (M+H).

Example 77

3-({4-[[2-(3-chlorobenzyl)-3-methyl-2H-indazol-6-yl](methyl)amino]pyrimidin-2-yl}amino)benzenesulfonamide

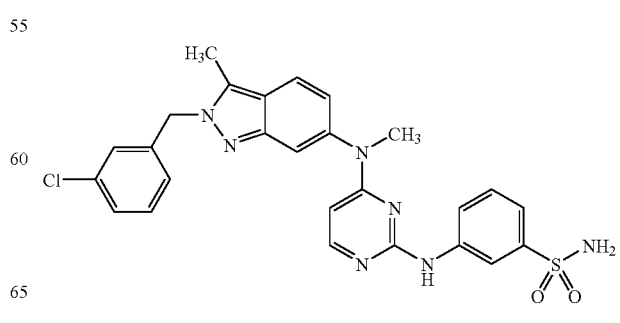

Intermediate Example 9 (10 g, 0.029 mol) was treated with excess trifluoroacetic acid (20 ml) at rt for 30 min. The reaction mixture was quenched with NaHCO₃ and extracted with ethyl acetate. The organic layer was separated, and the aqueous layer was thoroughly extracted with EtOAc. The combined organic layer was dried over anhydrous MgSO₄, filtered and evaporated to give N-(2-chloropyrimidin-4-yl)-N,3-dimethyl-1H-indazol-6-amine as an off-white solid (7.3 g, 100%). ¹H NMR (300 MHz, d₆DMSO) δ 12.80 (br s, 1H), 7.94 (d, J=6.0 Hz, 1H), 7.82 (d, J=8.5 Hz, 1H), 7.44 (s, 1H), 7.01 (m, 1H), 6.25 (d, J=6.0 Hz, 1H), 3.42 (s, 3H), 2.50 (s, 3H). MS (ES+, m/z) 274 (M+H).

N-(2-chloropyrimidin-4-yl)-N,3-dimethyl-1H-indazol-6-amine (2 g, 7.31 mmol) was dissolved in DMF (15 ml), and Cs₂CO₃ (2 g, 14.6 mmol) and 3-chlorobenzyl bromide (1.25 ml, 9.5 mmol) were added at room temperature. Mixture was stirred at rt for overnight. The reaction mixture was diluted with ethyl acetate and washed with water. The organic layer was separated. The aqueous layer was thoroughly extracted with EtOAc. The combined organic layers were dried over anhydrous MgSO₄, filtered and evaporated to give 2-(3-chlorobenzyl)-N-(2-chloropyrimidin-4-yl)-N,3-dimethyl-2H-indazol-6-amine as an off-white solid. ¹H NMR (300 MHz, d₆DMSO) δ 7.94 (d, J=6.0 Hz, 1H), 7.83 (d, J=8.8 Hz, 1H), 7.56 (d, J=1.3 Hz, 1H), 7.36-7.38 (m, 2H), 7.32 (br s, 1H), 7.16 (m, 1H), 6.91 (m, 1H), 6.28 (d, J=6.1 Hz, 1H), 5.65 (s, 2H), 3.42 (s, 3H), 2.63 (s, 3H). MS (ES+, m/z) 398 (M+H).

To a solution of 2-(3-chlorobenzyl)-N-(2-chloropyrimidin-4-yl)-N,3-dimethyl-2H-indazol-6-amine (40 mg, 0.1 mmol) and 3-aminobenzenesulfonamide (17.3 mg, 0.1 mmol) in isopropanol (2 ml) was added 2 drops of conc. HCl. The mixture was heated to reflux overnight. The mixture was cooled to rt. Precipitate was collected via filtration and washed with EtOH. HCl salt of 3-({4-[[2-(3-chlorobenzyl)-3-methyl-2H-indazol-6-yl](methyl)amino]-pyrimidin-2-yl}amino)benzenesulfonamide was isolated as off-white solid. ¹H NMR (400 MHz, d₆DMSO+NaHCO₃) δ 9.52 (br s, 1H), 8.54 (br s, 1H), 7.85 (d, J=5.9 Hz, 1H), 7.77-7.79 (m, 2H), 7.49 (s, 1H), 7.30-7.36 (m, 5H), 7.22 (br s, 2H), 7.14 (br s, 1H), 6.90 (d, J=8.7 Hz, 1H), 5.80 (d, J=5.8 Hz, 1H), 5.64 (s, 2H), 3.48 (s, 3H), 2.62 (s, 3H). MS (ES+, m/z) 534 (M+H).

Example 78

3-({4-[(2,3-dimethyl-2H-indazol-6-yl)(methyl)amino]-1,3,5-triazin-2-yl}amino)benzenesulfonamide

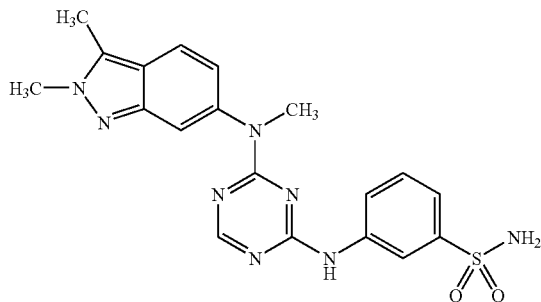

Intermediate Example 15 (0.017 g, 0.06 mmol), and 3-aminobenzenesulfonamide (0.01 g, 0.06 mmol) were combined in EtOH. A 1N solution of HCl in diethylether was added (0.06 mL, 0.06 mmol), and the solution was warmed to reflux for 18 h. The solution was cooled to RT, and the precipitate was filtered off, washed with EtOH, and dried, to give analytically pure product as a white solid (0.025 g). ¹H NMR (300 MHz, d₆DMSO) δ 9.99 (br s, 1H), 8.24 (br s, 1H), 7.80 (d, J=6.4 Hz, 1H), 7.68 (d, J=8.0 Hz, 1H), 7.40-7.46 (m, 2H), 7.27-7.33 (m, 2H), 6.93 (d, J=7.7 Hz, 1H), 4.05 (s, 3H), 3.51 (s, 3H), 2.62 (s, 3H). MS (ES+, m/z) 425 (M+H).

Example 79

5-({4-[(2,3-dimethyl-2H-indazol-6-yl)(methyl)amino]-1,3,5-triazin-2-yl}amino)-2-methylbenzenesulfonamide

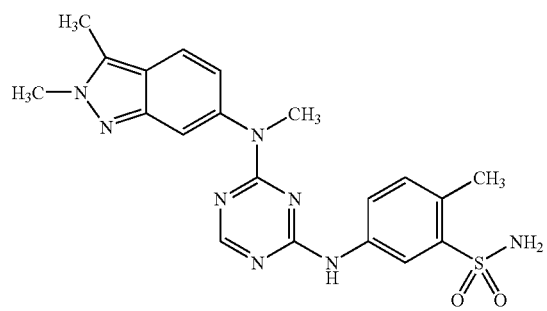

Intermediate Example 15 (0.032 g, 0.11 mmol), and 3-amino-4-methylbenzenesulfonamide (0.021 g, 0.11 mmol) where combined in EtOH. A 1N solution of HCl in diethylether was added (0.06 mL, 0.06 mmol), and the solution was warmed to reflux for 18 h. The solution was cooled to RT, and the precipitate was filtered off, washed with EtOH, and dried, to give analytically pure product as a tan solid (0.033 g). ¹H NMR (300 MHz, d₆DMSO) δ 9.88 (br s, 1H), 8.19 (br s, 1H), 7.70-7.65 (m, 2H), 7.41 (s, 1H), 7.28 brs, 2H), 6.90 (d, J=8.8 Hz, 1H), 4.04 (s, 3H), 3.50 (s, 3H), 2.61 (s, 3H), 2.49 (s, 3H), MS (ES+, m/z) 439 (M+H).

Biological Data

The compounds of the present invention elicit important and measurable pharmacological responses. Each of the compounds described in the Examples section bind with high affinity (IC₅₀<1 μM) to the kinase domain of VEGFR2 receptor, as described by the VEGFR2 HTRF assay below. In addition to binding to the kinase domain of VEGFR2, the exemplified compounds of the present invention also measurably and significantly inhibit the proliferation of endothelial cells that are stimulated for growth by activation with VEGF. Data for inhibition of cell proliferation are provided in Table 1 below.

VEGFR2 HTRF Assay

The assays were performed in 96-well black plates. 10 nM hVEGFR2 was used to phosphorylate 0.36 μM peptide (Biotin-Ahx-EEEEYFELVAKKKK) in the presence of 75 μM ATP, 5 mM MgCl₂, 0.3 mM DTT, 0.1 mg/ml BSA, and 0.1 M HEPES (pH 7.5). 10 μl 0.5 M EDTA was added to reactions as negative controls. The 50 μl kinase reaction with or without inhibitors in 5% DMSO was carried out at room temperature for 45 minutes, then stopped by 40 μl of 125 mM EDTA. 2.4 μg/ml Streptavidin-APC and 0.15 μg/ml Eu-α-pY, in the presence of 0.1 mg/ml BSA, 0.1 M HEPES (pH7.5), were added to a final volume of 140 μl. The plate was incubated for 10 min at room temperature (22° C.) and read on the Victor with the time resolved fluorescence mode by exciting at 340 nm and reading the emission at 665 nm.

Reagent Resources:

Peptide from Synpep (Dublin, Calif.)

ATP, $MgCl_2$, DTT, BSA, HEPES, EDTA, DMSO from Sigma

Streptavidin-APC from Molecular Probes (Eugene, Oreg.)

Eu-α-pY from EG&G Wallac (Gaithersburg, Md.)

Abbreviations:

| | |
|---|---|
| ATP | Adenosine Triphosphate |
| Streptavidin-APC | Streptavidin, allophycocyanine, crosslinked conjugate |
| DMSO | Dimethyl Sulfoxide |
| DTT | Dithiothreitol |
| BSA | Bovine Serum Albumin |
| HTRF | Homogenous Time Resolved Fluorescence |
| EDTA | Ethylenedinitrilo Tetraacetic Acid |
| HEPES | N-2-Hydroxyethyl Piperazine N-Ethane Sulfonic Acid |
| Eu-α-pY | Europium labeled anti-phosphotyrosine antibody |

Human Umbilical Vein Endothelial Cell (HUVEC) Proliferation Assay (BrdU Incorporation)

Materials

HUVEC cells and EGM-MV (Endothelial cell growth medium-microvascular) were purchased from Clonetics (San Diego, Calif.). VEGF and bFGF were purchased from R&D Systems (Minneapolis, Minn.). Anti-BrdU antibody was obtained from Chemicon International (Temecula, Calif.).

Methods

HUVECs were routinely maintained in EGM-MV medium and were used within passage 7. HUVECs were plated at a density of 2500 cells/well in M199 medium containing 5% FBS (Hyclone) in type I collagen coated plate (Becton Dickinson). The plate was incubated at 37° C. overnight. The medium was removed by aspiration, and test compounds were added to each well in a volume of 0.1 ml/well in serum-free M199 medium. Compound concentrations ranged from 1.5 nM to 30 micromolar. The plate was incubated for 30 min at 37° C. Another 0.1 ml of serum-free M199 medium containing BSA and VEGF (or bFGF) was added to give a final concentration of 0.1% BSA and 10 ng/ml VEGF (0.3 ng/ml bFGF). The plate was incubated at 37° C. for 72 hrs. BrdU was added to each well after the first 48 hrs to give a concentration of 10 micromolar. The colorimetric ELISA assay was performed according to manufacturer's (Roche Molecular Sciences) instructions, with detection by absorbance reading at 450 nm. Results were plotted as concentration of test compound vs. absorbance to give an $IC_{50}$ value for inhibition of BrdU incorporation.

Table 1=Inhibition of HUVEC proliferation ($IC_{50}$ in nM; 1-200 nM=++++; 201-500 nM=+++; 501-1000 nM=++; >1,000=+)

TABLE 1

| Example No. | $IC_{50}$ |
|---|---|
| 1 | +++ |
| 2 | ++++ |
| 3 | ++++ |
| 4 | +++ |
| 5 | +++ |
| 6 | +++ |
| 7 | +++ |
| 8 | +++ |
| 9 | +++ |
| 10 | + |
| 11 | +++ |
| 12 | ++++ |
| 13 | +++ |
| 14 | ++++ |
| 15 | ++ |
| 16 | +++ |
| 17 | ++ |
| 18 | ++ |
| 19 | +++ |
| 20 | + |
| 21 | ++++ |
| 22 | ++++ |
| 23 | ++++ |
| 24 | ++++ |
| 25 | ++++ |
| 26 | +++ |
| 27 | ++++ |
| 28 | ++++ |
| 29 | ++++ |
| 30 | ++ |
| 31 | ++++ |
| 32 | ++++ |
| 33 | + |
| 34 | +++ |
| 35 | ++++ |
| 36 | + |
| 37 | +++ |
| 38 | +++ |
| 39 | ++++ |
| 40 | ++++ |
| 41 | ++ |
| 42 | +++ |
| 43 | +++ |
| 44 | +++ |
| 45 | ++ |
| 46 | ++++ |
| 47 | +++ |
| 48 | ++++ |
| 49 | ++++ |
| 50 | +++ |
| 51 | +++ |
| 52 | ++++ |
| 53 | ++++ |
| 54 | ++++ |
| 55 | ++++ |
| 56 | ++++ |
| 57 | +++ |
| 58 | ++++ |
| 59 | ++++ |
| 60 | ++++ |
| 61 | +++ |
| 62 | ++++ |
| 63 | +++ |
| 64 | ++++ |
| 65 | ++++ |
| 66 | ++++ |
| 67 | +++ |
| 68 | ++++ |
| 69 | ++++ |
| 70 | ++++ |
| 71 | ++++ |
| 72 | ++++ |
| 73 | ++++ |
| 74 | ++++ |
| 75 | ++++ |
| 76 | ++++ |
| 77 | ++++ |
| 78 | ++++ |
| 79 | +++ |

The application of which this description and claim(s) forms part may be used as a basis for priority in respect of any subsequent application. The claims of such subsequent application may be directed to any feature or combination of features described herein. They may take the form of product, composition, process or use claims and may include, by way of example and without limitation, one or more of the following claim(s):

We claim:

1. A compound of formula (II):

(II)

or a salt thereof,
wherein:
$X_1$ is methyl or ethyl;
$X_2$ is hydrogen or methyl;
$X_3$ is hydrogen;
$X_4$ is hydrogen, methyl, or ethyl;
W is N;
$Q_1$ is hydrogen, chlorine, or methoxy;
$Q_2$ is $A^1$ or $A^2$;
$Q_3$ is $A^1$ when $Q_2$ is $A^2$ and $Q_3$ is $A^2$ when $Q_2$ is $A^1$;
wherein
$A^1$ is hydrogen, methyl, or chlorine, and
$A^2$ is the group defined by $-(Z)_m-(Z^1)-(Z^2)$, wherein
Z is $CH_2$ and m is 0, 1, 2, or 3, or
Z is $NR^2$ and m is 0 or 1, or
Z is $CH_2NR^2$ and m is 0 or 1;
$Z^1$ is $S(O)_2$, and
$Z^2$ is $C_1$-$C_4$ alkyl or $NR^3R^4$; and
$R^2$, $R^3$, and $R^4$ are each independently selected from hydrogen and $C_1$-$C_4$ alkyl.

2. A compound as claimed in claim 1 wherein $X_1$ is methyl.

3. A compound as claimed in claim 1 wherein $X_2$ is hydrogen.

4. A compound as claimed in claim 1 wherein $X_2$ is methyl.

5. A compound as claimed in claim 1 wherein $X_4$ is methyl.

6. A compound as claimed in claim 1 wherein $X_1$ is methyl, $X_2$ is hydrogen, $X_3$ is hydrogen, and $X_4$ is methyl.

7. A compound as claimed in claim 1 wherein $X_1$ is methyl, $X_2$ is methyl, $X_3$ is hydrogen, and $X_4$ is methyl.

8. A compound as claimed in claim 1 wherein $Q_1$ is hydrogen.

9. A compound as claimed in claim 1 wherein $Q_1$ is chlorine.

10. A compound as claimed in claim 1 wherein $Q_1$ is methoxy.

11. A compound as claimed in claim 1 wherein $Q_2$ is $A^1$ and $Q_3$ is $A^2$.

12. A compound as claimed in claim 1 wherein $Q_2$ is $A^2$ and $Q_3$ is $A^1$.

13. A compound as claimed in claim 1 wherein $Q_2$ is $A^2$ and $Q_3$ is $A^1$, wherein $A^1$ is hydrogen or chlorine and $A^2$ is the group defined by $-(Z)_m-(Z^1)-(Z^2)$, wherein Z is $CH_2$ and m is 0, 1, 2, or 3; $Z^1$ is $S(O)_2$; and $Z^2$ is $C_1$-$C_4$ alkyl.

14. A compound as claimed in claim 1 wherein $Q_2$ is $A^1$ and $Q_3$ is $A^2$, wherein $A^1$ is hydrogen, methyl, or chlorine and $A^2$ is the group defined by $-(Z)_m-Z^1)_4Z^2)$, wherein Z is $CH_2$ and m is 0, 1, 2, or 3; $Z^1$ is $S(O)_2$; and Z is $C_1$-$C_4$ alkyl or $NR^3R^4$, wherein $R^3$ and $R^4$ are each independently selected from hydrogen or $C_1$-$C_4$ alkyl.

15. A compound as claimed in claim 1 selected from the group consisting of:
$N^2$-(3-methyl-1H-indazol-6-yl)-$N^4$-{3-[(methylsulfonyl)methyl]phenyl}-1,3,5-triazine-2,4-diamine trifluoroacetate;
$N^2$-methyl-$N^2$-(3-methyl-1H-indazol-6-yl)-$N^4$-4-{3-[(methylsulfonyl)methyl]phenyl}-1,3,5-triazine-2,4-diamine;
$N^2$-[5-(ethylsulfonyl)-2-methoxyphenyl]-$N^4$-methyl-$N^4$-(3-methyl-1H-indazol-6-yl)-1,3,5-triazine-2,4-diamine;
N-[2-methyl-5-({4-[methyl(3-methyl-1H-indazol-6-yl)amino]-1,3,5-triazin-2-yl}amino)phenyl]methanesulfonamide;
$N^2$-methyl-$N^2$-(3-methyl-1H-indazol-6-yl)-$N^4$-[3-(methylsulfonyl)phenyl]-1,3,5-triazine-2,4-diamine;
3-({4-[(2,3-dimethyl-2H-indazol-6-yl)(methyl)amino]-1,3,5-triazin-2-yl}amino)benzenesulfonamide; and
5-({4-[(2,3-dimethyl-2H-indazol-6-yl)(methyl)amino]-1,3,5-triazin-2-yl}amino)-2-methylbenzenesulfonamide;
or a salt thereof.

16. A pharmaceutical composition, comprising: a therapeutically effective amount of a compound as claimed in claim 1 or a pharmaceutically acceptable salt thereof and one or more of pharmaceutically acceptable carriers, diluents and excipients.

17. The pharmaceutical composition of claim 16, further comprising at least one additional agent that is an anti-neoplastic agent.

18. The pharmaceutical composition of claim 16, further comprising an additional agent that inhibits angiogenesis.

19. A method of treating a disorder in a mammal, said disorder being characterized by inappropriate angiogenesis, wherein said disorder is selected from the group consisting of colon cancer and breast cancer, comprising administering to said mammal a therapeutically effective amount of a compound as claimed in claim 1.

20. A compound as claimed in claim 1, wherein $X_1$ is methyl, $X_2$ is hydrogen, $X_3$ is hydrogen, $X_4$ is methyl, and $Q_1$ is hydrogen.

* * * * *